(12) United States Patent
Bruckschwaiger et al.

(10) Patent No.: US 9,782,477 B2
(45) Date of Patent: Oct. 10, 2017

(54) FRACTION I-IV-1 PRECIPITATION OF IMMUNOGLOBINS FROM PLASMA

(71) Applicants: Baxalta Incorporated, Bannockburn, IL (US); Baxalta GmbH, Glattpark (Opfikon) (CH)

(72) Inventors: Leopold Bruckschwaiger, Vienna (AT); Thomas Gundinger, Vienna (AT); Julia Nuernberger, Vienna (AT); Wolfgang Teschner, Vienna (AT); Hans-Peter Schwarz, Vienna (AT)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 257 days.

(21) Appl. No.: 13/776,448

(22) Filed: Feb. 25, 2013

(65) Prior Publication Data
US 2013/0224183 A1 Aug. 29, 2013

Related U.S. Application Data

(60) Provisional application No. 61/602,488, filed on Feb. 23, 2012.

(51) Int. Cl.
| | |
|---|---|
| *A61K 39/39* | (2006.01) |
| *A61K 35/16* | (2015.01) |
| *C07K 16/30* | (2006.01) |
| *C07K 1/14* | (2006.01) |
| *A61K 39/395* | (2006.01) |
| *C07K 16/06* | (2006.01) |
| *C07K 1/30* | (2006.01) |

(52) U.S. Cl.
CPC ............ *A61K 39/395* (2013.01); *A61K 35/16* (2013.01); *A61K 39/39591* (2013.01); *C07K 1/30* (2013.01); *C07K 16/065* (2013.01); *C07K 1/145* (2013.01)

(58) Field of Classification Search
None
See application file for complete search history.

(56) References Cited

U.S. PATENT DOCUMENTS

| | | | |
|---|---|---|---|
| 3,998,946 A | | 12/1976 | Condie et al. |
| 4,136,094 A | | 1/1979 | Condie |
| 4,476,109 A | * | 10/1984 | Kimura et al. ............ 424/177.1 |
| 4,499,073 A | | 2/1985 | Tenold |
| 5,122,373 A | | 6/1992 | Eibl et al. |
| 5,177,194 A | | 1/1993 | Sarno et al. |
| 5,886,154 A | | 3/1999 | Lebing et al. |
| 6,069,236 A | | 5/2000 | Burnouf-Radosevich et al. |
| 6,093,324 A | | 7/2000 | Bertolini et al. |
| 6,124,437 A | | 9/2000 | Hirao et al. |
| 6,159,471 A | | 12/2000 | Hirao et al. |
| 6,485,932 B1 | * | 11/2002 | McIntosh ......... A61K 39/39591 424/130.1 |
| 6,835,379 B2 | | 12/2004 | Andersson et al. |
| 7,186,410 B2 | | 3/2007 | Chtourou et al. |
| 7,553,938 B2 | | 6/2009 | Buchacher et al. |
| 2010/0330071 A1 | | 12/2010 | Teschner et al. |
| 2011/0021432 A1 | * | 1/2011 | Bairstow et al. ............ 514/15.3 |

FOREIGN PATENT DOCUMENTS

| | | |
|---|---|---|
| GB | 1 344 340 | 9/1972 |
| SE | 348 942 | 9/1972 |
| WO | WO 03034982 A2 * | 5/2003 |
| WO | WO 2005/073252 A1 | 8/2005 |
| WO | WO 2008/113589 A1 | 9/2008 |
| WO | WO 2011/011753 A1 | 1/2011 |
| WO | WO 2011/149472 A1 | 12/2011 |
| WO | WO 2011/150284 A2 | 12/2011 |
| WO | WO 2011150284 A2 * | 12/2011 |
| WO | WO 2012/012773 A1 | 1/2012 |

OTHER PUBLICATIONS

Lever et al. "chemical, clinical and immunological studies on the products of human plasma fractionation XL. Quantiative separation and determination of the protein components in small amounts of normal human plasma" J Clin Invest Jan. 1951; 30(1): 99-111.*
Piszkiewieza, "Inactivation of HTLV-III/LAV during plasma fractionation" 326(8465), 1985, pp. 1188-1189.*
Hink et al. "preparation and properties of a heat-treated human plasma protein fraction" Vox Sanguinis 2, 174, 1957.*
Buchacher, et al., "Purification of intravenous immunoglobulin G from human plasma—aspects of yield and virus safety," *Biotechnol. J*, 2006, 1, pp. 148-163.
Cammarata, P.S. et al., "Fractionation and Properties of Glutamic-Oxalacetic Transaminase," *The Journal of Biological Chemistry*, Nov. 1951, vol. 193, No. 1, pp. 53-62.
Cohn, E.J. et al., "Preparation and Properties of Serum and Plasma Proteins. IV. A System for the Separation into Fractions of the Protein and Lipoprotein Components of Biological Tissues and Fluids," *J. Am. Chem. Soc.*, Mar. 1946, pp. 459-475, vol. 68, No. 3.
Curling, J.M. ed., *Methods of Plasma Protein Factionation*, 1980, Academic Press, pp. 12-13. 248-249, Table 1.
Gun'Ko, V.M. et al., "Aqueous Suspensions of Fumed Silica and Adsorption of Proteins," Journal of Colloid and Interface Science, 1997, vol. 192, pp. 166-178.
International Search Report for International Patent Application No. PCT/US2013/027681 filed on Feb. 25, 2013, 4 pages.
Kistler, P. et al., "Large Scale Production of Human Plasma Fractions," *Vox Sang.*, 1962, vol. 7, pp. 414-424.
Kreil, T.R. et al., "Development of a New 10% Liquid, Triple Virus Reduced Intra-venous Immune-Globulin Product, New Generation IGIV," *J. Allergy Immunol.*, Feb. 2004, p. S128 Abstracts, Abstract No. 410.

(Continued)

*Primary Examiner* — Daniel E Kolker
*Assistant Examiner* — James Rogers
(74) *Attorney, Agent, or Firm* — Morgan, Lewis & Bockius LLP

(57) ABSTRACT

Among other aspects, the present invention provides methods for the manufacture of blood protein compositions from pooled plasma. In one embodiment, the invention provides an alcohol fractionation scheme that allows for significant increases in the yield of blood proteins purified from the starting plasma sample. In a specific embodiment, a method for fractionating pooled plasma is provided, the method comprising an initial low pH, high alcohol precipitation step. The present invention also provides pharmaceutical compositions of therapeutic blood proteins.

61 Claims, 1 Drawing Sheet

(56) References Cited

OTHER PUBLICATIONS

Kreil, T.R. et al., "Pathogen Safety Profile of a New 10% Liquid, Triple Virus Reduced Intravenous Immune Globulin Product, New Generation IGIV (NG IGIV)—Further Studies," *J. Allergy Clin. Immunol.*, Feb. 2005, p. S156 Abstracts, Abstract No. 623.

Kreil, T.R. et al., "Removal of small nonenveloped viruses by antibody-enhanced nanofiltration during the manufacture of plasma derivatives," *Transfusion*, Jul. 2006, pp. 1143-1151, vol. 46.

Oncley, J.L. et al., "The Separation of the Antibodies, Isoagglutinins, Prothrombin, Plasminogen and $\beta_1$-Lipoprotein into Subfractions of Human Plasma," *J. Am. Chem. Soc.*, Feb. 1949, pp. 541-550, vol. 71.

Poelsler, G. et al., "A new liquid intravenous immunoglobulin with three dedicated virus reduction steps: virus and prion reduction capacity," *Vox Sanguinis*, 2007, pp. 1-9.

Radosevich, M. et al., "Intravenous immunoglobulin G; trends in production methods, quality control and quality assurance," *Vox Sanguinis*. 2010, vol. 96. pp. 12-28.

Schultze, H.E. et al., *Molecular Biology of Human Proteins, vol. 1: Nature and Metabolism of Extracellular Proteins*, 1996, Elsevier Publishing Company, pp. 236-317.

Teschner, IV, W. et al., "Preclinical Characterization of a New Liquid 'Immune Globulin Intravenous (Human), 10% Triple Virally Reduced Solution' (IGIV, 10%TVR)," *J. Allergy Clin. Immunol.*, Feb. 2004, 2 pages, (p. Abstracts S45), Abstract No. 79, vol. 113, No. 2, Suppl 1.

Teschner, W. et al., "A new liquid, intravenous immunoglobulin product (IGIV 10%) highly purified by a state-of-the-art process," *Vox Sanguinis*, 2007, pp. 42-55, vol. 92.

\* cited by examiner

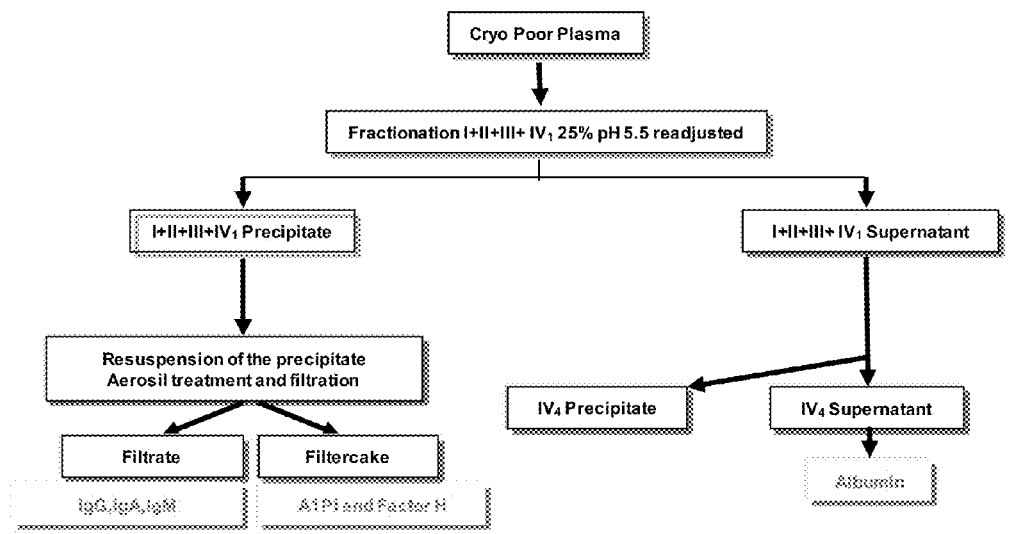

FRACTION I-IV-1 PRECIPITATION OF IMMUNOGLOBINS FROM PLASMA

CROSS REFERENCES TO APPLICATIONS

This application claims priority to U.S. Provisional Patent Application Ser. No. 61/602,488 filed Feb. 23, 2012, the disclosure of which is hereby incorporated herein by reference in its entirety for all purposes.

BACKGROUND OF THE INVENTION

Immune globulin products from human plasma were first used in 1952 to treat immune deficiency. Initially, intramuscular or subcutaneous administration of immunoglobulin isotype G (IgG) isolated from plasma were the methods of choice. However, these methods did not allow for the administration of larger amounts of IgG necessary for effective treatment of various diseases. Accordingly, IgG products that could be administered intravenously were developed. Usually, intravenous immunoglobulin (IVIG) contains the pooled immunoglobulin G (IgG) immunoglobulins from the plasma of more than a thousand blood donors. The preparations usually contain more than 95% unmodified IgG, which has intact Fc-dependent effector functions and only trace amounts of immunoglobulin A (IgA) and immunoglobulin M (IgM). Typically, IVIGs are sterile filtered and the manufacturing process contains steps to inactivate and/or remove viruses. These purified IgG products are primarily used in treating three main categories of medical conditions: (1) immune deficiencies: X-linked agammaglobulinemia, hypogammaglobulinemia (primary immune deficiencies), and acquired compromised immunity conditions (secondary immune deficiencies), featuring low antibody levels; (2) inflammatory and autoimmune diseases; and (3) acute infections.

Specifically, many people with primary immunodeficiency disorders lack antibodies needed to resist infection. In certain cases these deficiencies can be supplemented by the infusion of purified IgG, commonly through intravenous administration (i.e., IVIG therapy). Several primary immunodeficiency disorders are commonly treated in the fashion, including X-linked Agammaglobulinemia (XLA), Common Variable Immunodeficiency (CVID), Hyper-IgM Syndrome (HIM), Severe Combined Immunodeficiency (SCID), and some IgG subclass deficiencies (Blaese and Winkelstein, *J. Patient & Family Handbook for Primary Immunodeficiency Diseases*. Towson, Md.: Immune Deficiency Foundation; 2007).

While IgG treatment can be very effective for managing primary immunodeficiency disorders, this therapy is only a temporary replacement for antibodies that are not being produced in the body, rather than a cure for the disease. Accordingly, patients depend upon repeated doses of IgG therapy, typically about once a month for life. This therapy places a great demand on the continued production of IgG compositions. However, unlike other biologics that are produced via in vitro expression of recombinant DNA vectors, IgG is fractionated from human blood and plasma donations. Thus, the level of commercially available IgG is limited by the available supply of blood and plasma donations.

Several factors drive the demand for IgG, including the acceptance of IgG treatments, the identification of additional indications for which IgG therapy is effective, and increasing patient diagnosis and IgG prescription. Notably, the global demand for IgG more than quadrupled between 1990 and 2009, and continues to increase at an annual rate between about 7% and 10% (Robert P., Pharmaceutical Policy and Law, 11 (2009) 359-367). For example, the Australian National Blood Authority reported that the demand for IgG in Australia grew by 10.6% for the 2008-2009 fiscal year (National Blood Authority Australia Annual Report 2008-2009).

Due in part to the increasing global demand and fluctuations in the available supply of immunoglobulin products, several countries, including Australia and England, have implemented demand management programs to protect supplies of these products for the highest demand patients during times of product shortages.

It has been reported that in 2007, 26.5 million liters of plasma were fractionated, generating 75.2 metric tons of IgG, with an average production yield of 2.8 grams per liter (Robert P., supra). This same report estimated that global IgG yields are expected to increase to about 3.43 grams per liter by 2012. However, due to the continued growth in global demand for IgG, projected at between about 7% and 13% annually between now and 2015, further improvement of the overall IgG yield will be needed to meet global demand.

A number of IgG preparation methods are used by commercial suppliers of IgG products. A common problem with the current IgG production methods is the substantial loss of IgG during the purification process, estimated to be at least 30% to 35% of the total IgG content of the starting material. One challenge is to maintain the quality of viral inactivation and removal of impurities which can cause adverse reactions, while improving the process efficiency to increase the yield of IgG. At the current production levels of IgG, what may be considered small increases in the yield are in fact highly significant. For example at 2007 production levels, a 2% increase in efficiency, equal to an additional 56 milligrams per liter, would generate 1.5 additional metric tons of IgG.

In the fourth installment of a series of seminal papers published on the preparation and properties of serum and plasma proteins, Cohn et al. (J. Am. Chem. Soc., 1946, 68(3): 459-475) first described a method for the alcohol fractionation of plasma proteins (method 6), which allows for the isolation of a fraction enriched in IgG from human plasma. Several years later, Oncley et al. (J. Am. Chem. Soc., 1949, 71(2): 541-550) expanded upon the Cohn methods by publishing a method (method 9) that resulted in the isolation of a purer IgG preparation.

These methods, while laying the foundation for an entire industry of plasma derived blood proteins, were unable to provide IgG preparations having sufficiently high purity for the treatment of several immune-related diseases, including Kawasaki syndrome, immune thrombocytopenic purpura, and primary immune deficiencies. As such, additional methodologies employing various techniques, such as ion exchange chromatography, were developed to provide higher purity IgG formulations. Hoppe et al. (Munch Med Wochenschr 1967 (34): 1749-1752), Falksveden (Swedish Patent No. 348942), and Falksveden and Lundblad (Methods of Plasma Protein Fractionation 1980) were among the first to employ ion exchange chromatography for this purpose.

Various modern methods for the purification of immunoglobulins from plasma employ a precipitation step, such as caprylate precipitation (Lebing et al., Vox Sang 2003 (84): 193-201) and Cohn Fraction (I+)II+III ethanol precipitation (Tanaka et al., Braz J Med Biol Res 2000 (33)37-30) coupled to column chromatography. Most recently, Teschner et al. (Vox Sang, 2007 (92):42-55) have described a method for production of a 10% IgG product in which cryo-precipitate is first removed from pooled plasma and then a modified Cohn-Oncley cold ethanol fractionation is performed, followed by S/D treatment of the intermediate, ion exchange chromatography, nanofiltration, and optionally ultrafiltration/diafiltration.

Despite the purity, safety, and yield afforded by these IgG isolation methods, the yield of IgG recovered from plasma can still be improved. For example, Teschner et al. report that their method results in an increased IgG yield of 65% (Teschner et al., supra). As reported during various plasma product meetings, the average yields for large-scale preparation of IgG, such as from Baxter, CSL Behring, Upfront Technology, Cangene, Prometric BioTherapeutics, and the Finnish Red Cross, range from about 61% to about 65% in the final container. Although better than methods previously employed, this amount of IgG recovery still represents a loss of at least about a third of the IgG present in the pooled plasma fraction during the isolation process.

Due to the limited supply of plasma available for the manufacture of plasma-derived products, the isolation of several blood proteins from a common starting plasma pool can be achieved by integrating the purifications into a single framework. For example, IgG is commonly enriched through the formation of a Cohn Fraction II+III precipitate or Kistler-Nitschmann precipitate A, the corresponding supernatants of which are then used for the manufacture of alpha-1-antitrypsin (A1PI) and albumin. Similarly, several methods have been described for the manufacture of Factor H from by-products formed during the manufacture of IgG immunoglobulins, including WO 2008/113589 and WO 2011/011753.

As such, a need exists for improved and more efficient methods for manufacturing therapeutic IgG products. Furthermore, these methods should also allow for the manufacture of additional plasma-derived products from a single plasma source. The present invention satisfies these and other needs by providing IgG isolation methods that produce yields that are approximately 20 to 25% higher than currently achievable, as well as IgG compositions provided there from. Advantageously, the methods provided herein allow for the co-isolation of other therapeutically important plasma-derived proteins, including alpha-1-antitrypsin (A1PI), Factor H, inter-alpha-inhibitor proteins (IaIp), Prothrombin complexes, Factor VII (FVII), Factor VIII (FVIII), antithrombin III (ATIII), fibrinogen, butyrylcholinesterase, and others.

BRIEF SUMMARY OF INVENTION

Current methods for the production of IVIG and alpha-1-antitrypsin (A1PI) rely on multiple protein precipitation steps to separate immunoglobulin IgG and A1PI from other components found in human plasma. For example, many manufactures use a variation of the Cohn-Oncley method 6, in which three initial alcohol precipitation steps are employed. The first precipitation step, referred to as Fraction I precipitation, is performed at high pH (7.2) and low ethanol concentration (8-10% v/v) to precipitate protein such as fibrinogen and Factor XIII away from IgG and A1PI, which remain in the supernatant. IgG is then precipitated from the Fraction I supernatant in a second precipitation reaction, referred to as a Fraction II+III precipitation, performed at moderate pH (6.8) and high ethanol concentration (20%-25%). The bulk of the A1PI remains in the supernatant of the Fraction II+III precipitation reaction, as is subsequently separated from albumin in a third initial precipitation reaction, referred to as a Fraction I-IV-1 precipitation, performed at low pH (5.2) and moderate ethanol concentration (18%).

Unfortunately, because the Cohn-Oncley method described above, as well as the comparable Kistler-Nitschmann process that employs four initial precipitations to fractionate IgG and A1PI, separate individual components in an intricate series of precipitation reactions, the fractionation is inefficient. A significant loss in the yield of IgG and A1PI, in these initial precipitation steps, can be attributed to the partial precipitation into non-targeted fractions as well as incomplete precipitation in the targeted fractions. For example, IgG co-precipitates to some extent with fibrinogen and Factor XIII in the Fraction I precipitate and some IgG is not precipitated by Fraction II+III precipitation. After clarification of a dissolved Fraction II+III precipitate, the IgG yield is typically between 75% and 85% of the IgG present in the starting Cohn pool. Accordingly, 15% to 25% of the total IgG content of the starting material is lost after these two fractionation steps.

The present disclosure improves upon the recovery of IgG and A1PI from pooled plasma by removing the need for multiple initial precipitation steps. Rather, the methods described herein rely on a single initial precipitation step that captures all of the proteins normally precipitated in the Fraction I, Fraction II+III, and Fraction IV-1 preciptates combined. This single precipitation step is referred herein as a "Fraction I+II+III+IV-1 precipitation," a "Fraction I-IV-1 precipitation," or an "initial low pH, high alcohol precipitation." Advantageously, it was found that IgG and A1PI could be efficiently extracted from the Fraction I-IV-1 precipitate without the use of subsequent protein precipitations. Furthermore, it was found that the Fraction I-IV-1 precipitate contained nearly all of the IgG and A1PI content of the source plasma, while albumin remains in the supernatant. Taken together, these advantages result in a significant increase in the overall recovery of these important commercial products.

As shown in the Examples, the use of a low pH, high alcohol precipitation step (Fraction I-IV-1 precipitation) as an initial step in the purification of IgG from cryo-poor plasma, allows for the production of pharmaceutical grade IgG compositions with unprecedented yields of 4.3-4.7 g IgG/L source plasma. These yields represent an approximate 20% to 25% increase in yield as compared to state-of-the-art manufacturing processes, such as those used to manufacture GAMMAGARD LIQUID® (Baxter International; Deerfield, Ill.) from the same plasma type.

Accordingly, among other aspects, the present invention provides a new plasma fractionation process which separates plasma or cryo-poor plasma in an initial step into a Fraction I-IV-1 precipitate and a Fraction I-IV-1 supernatant. The Fraction I-IV-1 precipitate contains nearly all immunoglobulins (e.g., IgG, IgA, and IgM) and alpha 1 elastase inhibitor (A1PI), while the supernatant contains mainly albumin.

In one aspect, the present invention provides a method for preparing an enriched immunoglobulin composition from a Cohn pool, the method comprising the steps of: (a) co-precipitating immunoglobulins and alpha-1-antitrypsin (A1PI) from cryo-poor plasma, in a first precipitation step, to form a first precipitate and a first supernatant; (b) solubilizing immunoglobulins in the first precipitate, to form a first suspension having a soluble portion comprising immunoglobulins and an insoluble portion comprising A1PI; (c) separating the soluble portion of the first suspension from the insoluble portion of the first suspension; and (d) recovering the soluble fraction of the first suspension, thereby forming an enriched immunoglobulin composition.

In one embodiment of the methods described above, the first precipitation step is an alcohol precipitation step.

In one embodiment of the methods described above, the alcohol precipitation step comprises adding ethanol to the cryo-poor plasma to achieve a final concentration of from 20% to 30% ethanol (v/v) at a pH of from 5 to 6.

In one embodiment of the methods described above, the final concentration of ethanol in the first precipitation step is 25±4%. In one embodiment of the methods described above, the final concentration of ethanol is 25±3%. In one embodiment of the methods described above, the final concentration of ethanol is 25±2%. In one embodiment of the methods described above, the final concentration of ethanol is 25±1%. In one embodiment of the methods described above, the final concentration of ethanol is 25%.

In one embodiment of the methods described above, the pH of the first precipitation step is 5.5±0.4. In one embodiment of the methods described above, the pH is 5.5±0.3. In one embodiment of the methods described above, the pH is 5.5±0.2. In one embodiment of the methods described above, the pH is 5.5±0.1. In one embodiment of the methods described above, the pH is 5.5.

In one embodiment of the methods described above, the pH is maintained for the duration of the first precipitation step.

In one embodiment of the methods described above, the first alcohol precipitation step comprises addition of the alcohol by spraying.

In one embodiment of the methods described above, the first alcohol precipitation step comprises addition of the alcohol at a site adjacent to an impeller. In another embodiment, alcohol is introduced into the solution at more than one site. In one embodiment, alcohol is introduced into the solution at a plurality of small ports. In a specific embodiment, the multiple sites of alcohol addition ate located at or near an impeller or other dispersive element. In another embodiment, alcohol is introduced into the solution through a diffuser port comprising a plurality of openings. In a specific embodiment, one or more of the respective openings in the plurality of openings in the diffuser port is located at or proximal to an impeller or other dispersive element.

In one embodiment of the methods described above, the first precipitation step is performed at a temperature of from −3° C. to −10° C. In one embodiment of the methods described above, the first precipitation step is performed at a temperature of from −5° C. to −9° C.

In one embodiment of the methods described above, the first precipitate is suspended with from 4 L to 60 L of buffer per kg precipitate. In one embodiment of the methods described above, the first precipitate is suspended with from 8 L to 15 L of buffer per kg precipitate.

In one embodiment of the methods described above, the first suspension has a pH of from 4.0 to 5.4. In one embodiment of the methods described above, the first suspension has a pH of from 4.7 to 5.1.

In one embodiment of the methods described above, the first suspension has a conductivity of from 0 mS/cm to 4 mS/cm. In one embodiment of the methods described above, the first suspension has a conductivity of from 0.5 mS/cm to 2 mS/cm.

In one embodiment of the methods described above, the first precipitate is suspended in a buffer comprising acetate and/or phosphate.

In one embodiment of the methods described above, the soluble portion of the first suspension is separated from the insoluble portion of the first suspension by centrifugation or filtration.

In one embodiment of the methods described above, the step of separating the soluble portion of the first suspension from the insoluble portion of the first suspension comprises: (i) mixing finely divided silicon dioxide ($SiO_2$) with the first suspension; and (ii) separating the SiO2 from the suspension.

In one embodiment of the methods described above, the finely divided silicon dioxide ($SiO_2$) has an average surface area of from 350 $m^2$/g to 410 $m^2$/g.

In one embodiment of the methods described above, the finely divided silicon dioxide ($SiO_2$) is added to the first suspension at a final concentration of from 15 g/kg first precipitate to 80 g/kg first precipitate.

In one embodiment of the methods described above, the method comprises the steps of: (a) precipitating immunoglobulins from cryo-poor plasma, in a first precipitation step, with between 24% and 26% alcohol at a pH of between 5.3 and 5.7 and temperature of between −6° C. and −8° C. to form a first precipitate and a first supernatant; (b) suspending the first precipitate to form a first suspension; (c) treating the first suspension with finely divided silicon dioxide ($SiO_2$); (d) separating the soluble fraction of the first suspension from the insoluble fraction of the first suspension; and (e) recovering the soluble fraction of the first suspension, thereby forming an enriched immunoglobulin composition.

In one embodiment of the methods described above, the enriched immunoglobulin composition contains at least 90% of the immunoglobulin content of IgG present in the Cohn pool used in step (a).

In one embodiment of the methods described above, the enriched immunoglobulin composition contains at least 95% of the immunoglobulin content of IgG present in the Cohn pool used in step (a).

In one embodiment of the methods described above, the method further comprises the steps of (f) precipitating immunoglobulins from the soluble fraction of the first suspension, in a second precipitation step, to obtain a second precipitate and a second supernatant; (g) suspending the second precipitate to form a second suspension; and (h) recovering the soluble fraction of the second suspension, thereby forming a further enriched immunoglobulin composition.

In one embodiment of the methods described above, the second precipitation step is an alcohol precipitation step.

In one embodiment of the methods described above, the second alcohol precipitation step comprises adding ethanol to the soluble fraction of the first suspension to achieve a final concentration of between 22% and 28% ethanol at a pH between 6.5 and 7.5.

In one embodiment of the methods described above, the second alcohol precipitation step comprises addition of the alcohol by spraying.

In one embodiment of the methods described above, the second alcohol precipitation step comprises addition of the alcohol at a site adjacent to an impeller. In another embodiment, alcohol is introduced into the solution at more than one site. In one embodiment, alcohol is introduced into the solution at a plurality of small ports. In a specific embodiment, the multiple sites of alcohol addition ate located at or near an impeller or other dispersive element. In another embodiment, alcohol is introduced into the solution through a diffuser port comprising a plurality of openings. In a specific embodiment, one or more of the respective openings in the plurality of openings in the diffuser port is located at or proximal to an impeller or other dispersive element.

In one embodiment of the methods described above, the second precipitation step is performed at a temperature between −3° C. and −10° C.

In one embodiment of the methods described above, the enriched immunoglobulin composition contains at least 90% of the IgG content present in the cryo-poor plasma used in step (a).

In one embodiment of the methods described above, the enriched immunoglobulin composition contains at least 95% of the IgG content present in the cryo-poor plasma used in step (a).

In one embodiment of the methods described above, the method further comprises an anion exchange chromatography enrichment step.

In one embodiment of the methods described above, the method further comprises a cation exchange chromatography enrichment step.

In one embodiment of the methods described above, the method further comprises a viral inactivation or removal step.

In one embodiment of the methods described above, the method comprises a solvent/detergent (S/D) viral inactivation step.

In one embodiment of the methods described above, the method comprises a nanofiltration step.

In one embodiment of the methods described above, the method comprises a step of incubating the composition at a pH from 4.0 to 5.0 and temperature from 20° C. to 40° C. for at least one week.

In one embodiment of the methods described above, the final enriched IgG composition comprises at least 98% IgG.

In one embodiment of the methods described above, the final enriched IgG composition comprises at least 99% IgG.

In one embodiment of the methods described above, the method yields at least 4 g of IgG per L of cryo-poor plasma used in step (a).

In one embodiment of the methods described above, the method yields at least 4.25 g of IgG per L of cryo-poor plasma used in step (a).

In one embodiment of the methods described above, the method yields at least 4.5 g of IgG per L of cryo-poor plasma used in step (a).

In one embodiment of the methods described above, alpha-1-antitrypsin (A1PI) is further purified from an insoluble fraction of the first suspension.

In one embodiment of the methods described above, fibrinogen is further purified from an insoluble fraction of the first suspension.

In one embodiment of the methods described above, Factor H is further purified from an insoluble fraction of the first suspension.

In one embodiment of the methods described above, an Inter-alpha-Trypsin Inhibitor protein (IαIp) is further purified from an insoluble fraction of the first suspension.

In one embodiment of the methods described above, the insoluble fraction of the first suspension is treated with finely divided silicon dioxide ($SiO_2$).

In one embodiment of the methods described above, albumin is further purified from the first supernatant.

In one aspect, the present invention provides an enriched immunoglobulin composition prepared by a method according to any one of claims 1 to 63.

In one aspect, the present invention provides a method for treating an immune deficiency, an inflammatory disease, an autoimmune disease, or an acute infection in an individual in need thereof, the method comprising administering an enriched immunoglobulin composition of claim 64 to the subject.

BRIEF DESCRIPTION OF DRAWINGS

FIG. 1. Diagram of an plasma fractionation scheme according to one embodiment described herein.

DETAILED DESCRIPTION OF INVENTION

I. Introduction

Among other aspects, the present invention provides a more efficient method for the isolation of therapeutic proteins from pooled plasma. The methods provided herein for the fractionation of pooled plasma provide higher yields of multiple therapeutically important plasma-derived blood proteins, including immunoglobulins and alpha-1-antitrypsin (A1PI). In a particularly important aspect, the present invention provides methods that significantly increase the yield of immunoglobulin G (IgG) isolated from plasma, as compared to state of the art methods used for the manufacture of therapeutic IgG compositions. In one embodiment, these improved yields are achieved by precipitating immunoglobulins and A1P1 from a starting plasma sample (herein referred to as a "Cohn pool") under low pH, high alcohol conditions. The low pH, high alcohol precipitation step results in a mass capture of the immunoglobulin composition of the starting Cohn pool. As compared to state-of-the art immunoglobulin manufacturing processes, the methods provided herein significantly reduce the amount of immunoglobulin lost during the upstream fractionation of plasma.

The inventive methods reduce the number of protein precipitation steps required for the isolation of proteins from human plasma at sufficiently high purities for therapeutic administration, while simultaneously increasing the recovery yield of therapeutically important blood proteins such as immunoglobulin G (IgG). Specifically, the methods eliminate the need for an initial high pH, low alcohol precipitation step, commonly referred to a Fraction I precipitation, used in manufacturing processes derived from Cohn-Oncley, Kistler-Nitschmann, and Deutsch fractionation schemes. Instead, the methods provided herein employ an initial low pH, high alcohol precipitation step (herein referred to as Fraction I-IV-1 precipitation) that partitions the bulk of the IgG, IgA, IgM, and alpha-1-antitrypsin (A1PI) content of the plasma in the precipitate and the bulk of the albumin in the supernatant. IgG is then separated from IgA, IgM, and A1PI through various means, resulting in high yield IgG compositions. As compared to methods that employ a Fraction I precipitation step, the mass capture of IgG in the initial Fraction I-IV-1 precipitation step increases the final yield of the manufacturing process by at least 10 to 25%.

E. J. Cohn first established a method for the fractionation of plasma using ethanol, rather than salts, in 1946. Since this time, ethanol precipitation has become the method of choice for the large-scale manufacture of plasma-derived products, such as IgG and A1PI. Typically, these manufacturing processes employ a series of ethanol fractionation steps, providing crude fractions of various plasma-derived blood proteins, which are further enriched by various different downstream procedures/techniques.

The Cohn procedures were initially developed to obtain albumin at relatively high (95%) purity by fractional precipitation with alcohol. However, it was quickly realized by Oncley et al., Deutsch et al., and Kistler and Nitschmann, that a particular protein precipitate (Fraction II+III) from Cohn method number 6 could be used as a starting material for the purification of highly enriched immunoglobulin compositions. In order to achieve the higher purity and safety required for the intravenous administration of IgG compositions, several purification and polishing steps (e.g. adsorption in general or all different chromatographic techniques, Cross-flow-filtration, etc.) have been added to IgG manufacturing processes after the alcohol fractionation steps.

Typically, IgG manufactures rely on either a Cohn method 6 Fraction II+III precipitate or a Kistler-Nitschmann precipitate A as the starting material for downstream processing. Both fractions are formed by a two step process in which: i.) proteins such as fibrinogen and Factor XIII are removed by an initial precipitation step (Fraction I precipitation) performed at high pH (7.2) with low ethanol concentration (8-10% v/v); and ii.) IgG is precipitated from the Fraction I supernatant at pH 6.8 with 20-25% (v/v) ethanol (Fraction II+III) or at pH 5.85 with 19% ethanol (v/v) ethanol (precipitate A), while albumin and a significant portion of A1PI remain in the supernatant. However, the use of a Fraction II+III precipitate or precipitate A as the starting material for the manufacture of IgG compositions results in the loss IgG at several steps in the process, as described above.

To overcome these issues, the inventors have developed an initial purification step that co-precipitates immunoglobulins and A1PI to provide a starting material containing nearly all of the IgG and A1PI content of the source plasma, while the albumin remains in the supernatant. This fractionation step essentially collapses fractional precipitation steps I, II+III, and IV-1 as described by Oncley et al. (supra) into a single precipitation reaction, referred to herein as Fraction I+II+III+IV-1 (or Fraction I-IV-1) precipitation.

In one aspect, the present invention provides a process for manufacturing a high yield immunoglobulin composition for intravenous, subcutaneous, or intramuscular administration using a Fraction I-IV-1 precipitate as a starting material. In various embodiments, the method further comprises the separation of alpha-1-antitrypsin (A1PI) into an insoluble fraction of a suspension formed during the extraction of immunoglobulin from the Fraction I-IV-1 precipitate. The separated insoluble fraction can then be used as a starting material for the manufacture of a plasma-derived A1PI composition.

In one embodiment, the present invention provides methods for manufacturing a therapeutic composition of a protein isolated from pooled plasma. In some embodiments, these manufacturing methods include an initial low pH, high alcohol (e.g., ethanol) precipitation step that increases the recovery of various blood proteins, as compared to traditional methods. In some embodiments, the methods are useful for manufacturing one or more therapeutic compositions containing an immunoglobulin (e.g., IgG), albumin, alpha-1-antitrypsin (A1PI), butyrylcholinesterase, Factor H, or an inter-alpha-trypsin inhibitor (IαI) protein isolated from human blood, plasma, or a derivative thereof.

II. Definitions

As used herein, the term "IgG treatment" refers generally to a therapeutic method of intravenously, subcutaneously, or intramuscularly administering a composition of IgG immunoglobulins to a patient for treating a number of conditions such as immune deficiencies, inflammatory diseases, and autoimmune diseases. The IgG immunoglobulins are typically pooled and prepared from plasma. Whole antibodies or fragments can be used. IgG immunoglobulins can be formulated in higher concentrations (e.g., greater than 10%) for subcutaneous administration, or formulated for intramuscular administration. This is particularly common for specialty IgG preparations which are prepared with higher than average titres for specific antigens (e.g., Rho D factor, pertussis toxin, tetanus toxin, botulism toxin, rabies, etc.).

As used herein, "cryo-poor plasma" refers to the supernatant created after the removal of cryo-precipitate formed by thawing plasma or pooled plasma at temperatures near freezing, e.g., at temperatures below about 10° C., preferably at a temperature no higher than about 6° C. In the context of the present invention, plasma may refer interchangeably to recovered plasma (i.e., plasma that has been separated from whole blood ex vivo) or source plasma (i.e., plasma collected via plasmapheresis). Cryo-precipitation is commonly performed, for example, by thawing previously frozen pooled plasma, which has already been assayed for safety and quality considerations, although fresh plasma may also be used. After complete thawing of the frozen plasma at low temperature, separation of the solid cryo-precipitates from the liquid supernatant is performed in the cold (e.g., <6° C.) by centrifugation or filtration.

As used herein, a "Cohn pool" refers to the starting material used for the fractionation of a plasma sample or pool of plasma samples. Cohn pools may include one or more of whole plasma, cryo-poor plasma, and cryo-poor plasma that has been subjected to a pre-processing step. In certain embodiments, a Cohn pool is a cryo-poor plasma sample from which one or more blood factor have been removed in a pre-processing step, for example, by adsorption onto a solid phase (e.g., aluminum hydroxide, finely divided silicon dioxide, etc.), or chromatographic step (e.g., ion exchange or heparin affinity chromatography). Various blood proteins, including but not limited to Factor Eight Inhibitor Bypass Activity (FEIBA), Factor IX-complex, Factor VII, Prothrombin complexes, and/or antithrombin III, may be isolated from the cryo-poor plasma sample prior to fractionation.

As used herein, the term "enriched composition" refers to a protein composition isolated from a plasma sample, in which the purity of the protein is higher than the purity of the protein in the starting plasma sample. In one embodiment, a protein in an enriched composition is at least 25% more pure than in the starting plasma sample. In other embodiments, an enriched composition is at least 50%, 75%, 100%, 2-fold, 3-fold, 4-fold, 5-fold, 6-fold, 7-fold, 8-fold, 9-fold, 10-fold, or more pure than the starting plasma sample. For example, an enriched IgG composition in which 70% of the total protein is IgG is 7-fold enriched as compared to a starting plasma sample in which 10% of the total protein is IgG.

As used herein, the term "diffuse addition" refers to a means of adding a substance to a liquid system in a delocalized fashion. Diffuse addition may be achieved, for example, by spraying or misting a liquid (e.g., alcohol, pH modifying agent, solvent, detergent, or other liquid) into an liquid system (e.g., plasma fraction), introducing a liquid into a system at multiple sites, introducing a liquid into a system using a diffuser port, introducing a liquid at or proximal to an impeller or other dispersive element, or distributing a chemical present in a solid-state over an expanded area of a liquid system.

As used herein, the term "spraying" refers to a means of delivering a liquid substance into a system, e.g., during an alcohol precipitation step, such as a Fraction I-IV-1 precipitation step, in the form of fine droplets or mist of the liquid substance. Spraying may be achieved by any pressurized device, such as a container (e.g., a spray bottle), that has a spray head or a nozzle and is operated manually or automatically to generate a fine mist from a liquid. Typically, spraying is performed while the system receiving the liquid substance is continuously stirred or otherwise mixed to ensure rapid and equal distribution of the liquid within the system.

As used herein, the term "solvent" encompasses any liquid substance capable of dissolving or dispersing one or more other substances. A solvent may be inorganic in nature, such as water, or it may be an organic liquid, such as ethanol, acetone, methyl acetate, ethyl acetate, hexane, petrol ether, etc. As used in the term "solvent detergent treatment," solvent denotes an organic solvent (e.g., tri-N-butyl phosphate), which is part of the solvent detergent mixture used to inactivate lipid-enveloped viruses in solution.

As used herein, the term "detergent" is used in this application interchangeably with the term "surfactant" or "surface acting agent." Surfactants are typically organic compounds that are amphiphilic, i.e., containing both hydrophobic groups ("tails") and hydrophilic groups ("heads"), which render surfactants soluble in both organic solvents and water. A surfactant can be classified by the presence of formally charged groups in its head. A non-ionic surfactant has no charge groups in its head, whereas an ionic surfactant carries a net charge in its head. A zwitterionic surfactant contains a head with two oppositely charged groups. Some examples of common surfactants include: Anionic (based on sulfate, sulfonate or carboxylate anions): perfluorooctanoate (PFOA or PFO), perfluorooctanesulfonate (PFOS), sodium dodecyl sulfate (SDS), ammonium lauryl sulfate, and other alkyl sulfate salts, sodium laureth sulfate (also known as sodium lauryl ether sulfate, or SLES), alkyl benzene sulfonate; cationic (based on quaternary ammonium cations): cetyl trimethylammonium bromide (CTAB) a.k.a. hexadecyl trimethyl ammonium bromide, and other alkyltrimethylammonium salts, cetylpyridinium chloride (CPC), polyethoxylated tallow amine (POEA), benzalkonium chloride (BAC), benzethonium chloride (BZT); Long chain fatty acids and their salts: including caprylate, caprylic acid, heptanoat, hexanoic acid, heptanoic acid, nanoic acid, decanoic acid, and the like; Zwitterionic (amphoteric): dodecyl betaine; cocamidopropyl betaine; coco ampho glycinate; nonionic: alkyl poly(ethylene oxide), alkylphenol poly(ethylene oxide), copolymers of poly(ethylene oxide) and poly(propylene oxide) (commercially known as Poloxamers or Poloxamines), alkyl polyglucosides, including octyl glucoside, decyl maltoside, fatty alcohols (e.g., cetyl alcohol and oleyl alcohol), cocamide MEA, cocamide DEA, polysorbates (Tween 20, Tween 80, etc.), Triton detergents, and dodecyl dimethylamine oxide.

By "therapeutically effective amount or dose" or "sufficient/effective amount or dose," it is meant a dose that produces effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

As used herein, the terms "initial low pH, high alcohol precipitation" and "Fraction I-IV-1 precipitation" interchangeably refer to the precipitation of proteins from a Cohn pool at a final alcohol concentration (typically ethanol) of from 20% to 30% (v/v) and pH from 5.0 to 6.0. Generally, the resulting Fraction I-IV-1 precipitate contains at least 90% of the immunoglobulin content of the starting Cohn pool, preferably at least 95%, more preferably at least 98%, most preferably at least 99% of the immunoglobulin content of the starting Cohn pool. In a preferred embodiment, the immunoglobulins comprise IgG immunoglobulins. In another preferred embodiment, alpha-1-antitrypsin (A1PI) is co-precipitated with the immunoglobulins in the Fraction I-IV-1 precipitation.

III. Fractionation of Plasma

In one aspect, the present invention provides methods for fractionating therapeutic proteins from pooled plasma employing an initial precipitation step in which the majority of the immunoglobulin and alpha-1-antitrypsin (A1PI) content of the starting plasma is precipitated and the majority of the albumin content of the starting plasma is retained in the supernatant. Starting from this initial precipitation step, a number of therapeutically important blood proteins can be manufactured at high recovery yields.

In one embodiment, the present invention provides a method for fractionating blood proteins in a plasma sample, the method comprising precipitating immunoglobulins and A1PI from the starting plasma under low pH, high alcohol conditions. This low pH, high alcohol precipitation step results in the formation of a precipitate (referred to herein as a Fraction I-IV-1 precipitate) and a supernatant (referred to herein as a Fraction I-IV-1 supernatant).

The Fraction I-IV-1 supernatant will contain at least 70%, preferably at least 80%, most preferably at least 90% of the albumin content of the starting plasma. Accordingly, this supernatant can be used as a starting material for the manufacture of a pharmaceutical albumin composition.

The Fraction I-IV-1 precipitate will contain at least 90%, preferably at least 95%, more preferably at least 98%, most preferably at least 99% of the immunoglobulin content of the starting plasma. In a specific embodiment, the Fraction I-IV-1 precipitate contains at least 98%, preferably 99% of the IgG content of the starting plasma. Accordingly, this precipitate can be used as a starting material for the manufacture of pharmaceutical immunoglobulin compositions. In one embodiment, the Fraction I-IV-1 precipitate is used as a starting material for the manufacture of a pharmaceutical IgG composition. In yet another embodiment, the Fraction I-IV-1 precipitate is used as a starting material for the manufacture of a pharmaceutical immunoglobulin composition containing more than one immunoglobulin sub-type.

Likewise, the Fraction I-IV-1 precipitate will contain at least 90%, preferably at least 95%, more preferably at least 97%, most preferably at least 98% of the A1PI content of the starting plasma. Accordingly, this precipitate can be used as a starting material for the manufacture of a pharmaceutical A1PI composition.

The Fraction I-IV-1 precipitate will also contain at least 70%, preferably at least 80%, more preferably at least 90%, most preferably at least 95% of the Factor H content of the starting plasma. Accordingly, this precipitate can be used as a starting material for the manufacture of a pharmaceutical Factor H composition.

The Fraction I-IV-1 precipitate will also contain at least 70%, preferably at least 80%, more preferably at least 90%, most preferably at least 95% of the inter-alpha-inhibitor (IaIp) content of the starting plasma. Accordingly, this precipitate can be used as a starting material for the manufacture of a pharmaceutical IaIp composition.

In one aspect, the present invention provides a method for separating immunoglobulins from A1PI found in the Fraction I-IV-1 precipitate. In one embodiment, the method comprises solubilizing immunoglobulins in a suspension of the Fraction I-IV-1 precipitate, while retaining A1PI in the insoluble portion of the suspension and then separating the soluble and insoluble portions, for example by filtration or centrifugation. In one embodiment, the separation is aided by treating the Fraction I-IV-1 suspension with finely divided silicon dioxide prior to separating the soluble and insoluble portions. Without being bound by theory, the silicon dioxide may bind A1PI that is co-solubilized with the immunoglobulins, enhancing the amount of A1PI partitioned into the insoluble portion of the suspension.

Furthermore, it is known that Factor H and IaIp bind particulate silicon dioxide under certain conditions (see, WO/2011/011753, PCT/US2011/45099, and PCT/US2011/038247; the disclosures of which are hereby expressly incorporated by reference in their entireties for all purposes). Accordingly, in one embodiment, the present invention provides a method for separating immunoglobulins from A1PI, Factor H, and IaIp found in a Fraction I-IV-1 precipitate, the method comprising suspending a Fraction I-IV-1 precipitate in water or a low conductivity buffer sufficient to solubilize immunoglobulins; treating the suspension with silicon dioxide; and separating the soluble portion of the suspension from the insoluble portion, wherein soluble portion contains immunoglobulins and the insoluble portion contains A1PI, Factor H, and IaIp.

In one embodiment of the methods provided above, the separated soluble portion of the Fraction I-IV-1 suspension contains at least 80% of the IgG content of the starting plasma sample. In a preferred embodiment, the separated soluble portion of the Fraction I-IV-1 suspension contains at least 90% of the IgG content of the starting plasma sample. In a more preferred embodiment, the separated soluble portion of the Fraction I-IV-1 suspension contains at least 95% of the IgG content of the starting plasma sample. In yet other embodiments, the soluble portion of the Fraction I-IV-1 suspension contains at least 80%, 81%, 82%, 83%, 84%, 85%, 86%, 87%, 88%, 89%, 90%, 91%, 92%, 93%, 94%, 95%, 96%, 97%, 98%, 99%, or more of the IgG content of the starting plasma sample.

In one embodiment of the methods provided above, the separated insoluble portion of the Fraction I-IV-1 suspension contains at least 70% of the A1PI content of the starting plasma sample. In a preferred embodiment, the separated insoluble portion of the Fraction I-IV-1 suspension contains at least 80% of the A1PI content of the starting plasma sample. In a more preferred embodiment, the separated insoluble portion of the Fraction I-IV-1 suspension contains at least 90% of the A1PI content of the starting plasma sample. In a more preferred embodiment, the separated insoluble portion of the Fraction I-IV-1 suspension contains at least 95% of the A1PI content of the starting plasma sample. In yet other embodiments, the separated insoluble portion of the Fraction I-IV-1 suspension contains at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more of the A1PI content of the starting plasma sample.

Blood proteins fractionated using the initial mass precipitation step (e.g., Fraction I-IV-1 precipitation) may be further enriched by suitable procedures, for example, precipitation (e.g., alcohol fractionation or polyethylene glycol fractionation), chromatographic methods (ion exchange chromatography, affinity chromatography, immunoaffinity chromatography, etc.), filtration (ultrafiltration/diafiltration, nanofiltration), ultracentrifugation, electrophoretic preparation, and the like.

A. Preparation of Cryo-Poor Plasma

The starting material used for the preparation of concentrated IgG compositions generally consists of either recovered plasma (i.e., plasma that has been separated from whole blood ex vivo) or source plasma (i.e., plasma collected via plasmapheresis). The purification process typically starts with thawing previously frozen pooled plasma, which has already been assayed for safety and quality considerations. Thawing is typically carried out at a temperature no higher than 6° C. After complete thawing of the frozen plasma at low temperature, centrifugation is performed in the cold (e.g., <6° C.) to separate solid cryo-precipitates from the liquid supernatant. Alternatively, the separation step can be performed by filtration rather than centrifugation. The liquid supernatant (also referred to as "cryo-poor plasma," after cold-insoluble proteins removed by centrifugation from fresh thawed plasma) is then processed in the next step. Various additional steps can be taken at this juncture for the isolation of factor eight inhibitor bypass activity (FEIBA), Factor IX-complex, Factor VII, antithrombin III, Prothrombin complexes, etc.

B. First Precipitation Event—Fraction I-IV-1 Precipitation

In one embodiment, the present invention provides a method for fractionating blood proteins in a plasma sample, the method comprising precipitating immunoglobulins and A1PI from the starting plasma in a first precipitation step under low pH, high alcohol conditions. This low pH, high alcohol precipitation step results in the formation of a precipitate (Fraction I-IV-1 precipitate) and a supernatant (Fraction I-IV-1 supernatant).

In one embodiment, the first precipitation step is performed by admixing ethanol with a starting plasma pool (the Cohn pool) to a final concentration of from 20% to 30% (v/v) at a pH between 5.0 and 6.0. In one embodiment, ethanol is admixed with the Cohn pool to a final concentration of 25±3% (v/v). In another embodiment, ethanol is admixed with the Cohn pool to a final concentration of 25±2% (v/v). In another embodiment, ethanol is admixed with the Cohn pool to a final concentration of 25±1% (v/v). In another embodiment, ethanol is admixed with the Cohn pool to a final concentration of 25% (v/v). Likewise, in one embodiment, the first precipitation step is performed at a pH of 5.5±0.5. In another embodiment, the first precipitation step is performed at a pH of 5.5±0.4. In another embodiment, the first precipitation step is performed at a pH of 5.5±0.3. In another embodiment, the first precipitation step is performed at a pH of 5.5±0.2. In another embodiment, the first precipitation step is performed at a pH of 5.5±0.1. In another embodiment, the first precipitation step is performed at a pH of 5.5. In yet other embodiments, the final ethanol concentration and pH of the first precipitation step is selected from variations 1 to 2166, as listed in Table 1, Table 2, Table 3, Table 4, Table 5, Table 6, and Table 7.

TABLE 1

Combinations of pH and final ethanol concentration useful
for low pH, high alcohol precipitation of a Cohn pool.
Final Ethanol Concentration [% (v/v)]

| pH | 20-30 | 21-30 | 22-30 | 23-30 | 24-30 | 25-30 | 20-29 | 21-29 |
|---|---|---|---|---|---|---|---|---|
| 5.0-6.0 | Var. 1 | Var. 39 | Var. 77 | Var. 115 | Var. 153 | Var. 191 | Var. 229 | Var. 267 |
| 5.1-5.9 | Var. 2 | Var. 40 | Var. 78 | Var. 116 | Var. 154 | Var. 192 | Var. 230 | Var. 268 |
| 5.2-5.8 | Var. 3 | Var. 41 | Var. 79 | Var. 117 | Var. 155 | Var. 193 | Var. 231 | Var. 269 |
| 5.3-5.7 | Var. 4 | Var. 42 | Var. 80 | Var. 118 | Var. 156 | Var. 194 | Var. 232 | Var. 270 |
| 5.4-5.6 | Var. 5 | Var. 43 | Var. 81 | Var. 119 | Var. 157 | Var. 195 | Var. 233 | Var. 271 |
| 5.0 ± 0.2 | Var. 6 | Var. 44 | Var. 82 | Var. 120 | Var. 158 | Var. 196 | Var. 234 | Var. 272 |
| 5.1 ± 0.2 | Var. 7 | Var. 45 | Var. 83 | Var. 121 | Var. 159 | Var. 197 | Var. 235 | Var. 273 |
| 5.2 ± 0.2 | Var. 8 | Var. 46 | Var. 84 | Var. 122 | Var. 160 | Var. 198 | Var. 236 | Var. 274 |
| 5.3 ± 0.2 | Var. 9 | Var. 47 | Var. 85 | Var. 123 | Var. 161 | Var. 199 | Var. 237 | Var. 275 |
| 5.4 ± 0.2 | Var. 10 | Var. 48 | Var. 86 | Var. 124 | Var. 162 | Var. 200 | Var. 238 | Var. 276 |
| 5.5 ± 0.2 | Var. 11 | Var. 49 | Var. 87 | Var. 125 | Var. 163 | Var. 201 | Var. 239 | Var. 277 |
| 5.6 ± 0.2 | Var. 12 | Var. 50 | Var. 88 | Var. 126 | Var. 164 | Var. 202 | Var. 240 | Var. 278 |
| 5.7 ± 0.2 | Var. 13 | Var. 51 | Var. 89 | Var. 127 | Var. 165 | Var. 203 | Var. 241 | Var. 279 |
| 5.8 ± 0.2 | Var. 14 | Var. 52 | Var. 90 | Var. 128 | Var. 166 | Var. 204 | Var. 242 | Var. 280 |
| 5.9 ± 0.2 | Var. 15 | Var. 53 | Var. 91 | Var. 129 | Var. 167 | Var. 205 | Var. 243 | Var. 281 |
| 6.0 ± 0.2 | Var. 16 | Var. 54 | Var. 92 | Var. 130 | Var. 168 | Var. 206 | Var. 244 | Var. 282 |
| 5.0 ± 0.1 | Var. 17 | Var. 55 | Var. 93 | Var. 131 | Var. 169 | Var. 207 | Var. 245 | Var. 283 |
| 5.1 ± 0.1 | Var. 18 | Var. 56 | Var. 94 | Var. 132 | Var. 170 | Var. 208 | Var. 246 | Var. 284 |
| 5.2 ± 0.1 | Var. 19 | Var. 57 | Var. 95 | Var. 133 | Var. 171 | Var. 209 | Var. 247 | Var. 285 |
| 5.3 ± 0.1 | Var. 20 | Var. 58 | Var. 96 | Var. 134 | Var. 172 | Var. 210 | Var. 248 | Var. 286 |
| 5.4 ± 0.1 | Var. 21 | Var. 59 | Var. 97 | Var. 135 | Var. 173 | Var. 211 | Var. 249 | Var. 287 |
| 5.5 ± 0.1 | Var. 22 | Var. 60 | Var. 98 | Var. 136 | Var. 174 | Var. 212 | Var. 250 | Var. 288 |
| 5.6 ± 0.1 | Var. 23 | Var. 61 | Var. 99 | Var. 137 | Var. 175 | Var. 213 | Var. 251 | Var. 289 |
| 5.7 ± 0.1 | Var. 24 | Var. 62 | Var. 100 | Var. 138 | Var. 176 | Var. 214 | Var. 252 | Var. 290 |
| 5.8 ± 0.1 | Var. 25 | Var. 63 | Var. 101 | Var. 139 | Var. 177 | Var. 215 | Var. 253 | Var. 291 |
| 5.9 ± 0.1 | Var. 26 | Var. 64 | Var. 102 | Var. 140 | Var. 178 | Var. 216 | Var. 254 | Var. 292 |
| 6.0 ± 0.1 | Var. 27 | Var. 65 | Var. 103 | Var. 141 | Var. 179 | Var. 217 | Var. 255 | Var. 293 |
| 5 | Var. 28 | Var. 66 | Var. 104 | Var. 142 | Var. 180 | Var. 218 | Var. 256 | Var. 294 |
| 5.1 | Var. 29 | Var. 67 | Var. 105 | Var. 143 | Var. 181 | Var. 219 | Var. 257 | Var. 295 |
| 5.2 | Var. 30 | Var. 68 | Var. 106 | Var. 144 | Var. 182 | Var. 220 | Var. 258 | Var. 296 |
| 5.3 | Var. 31 | Var. 69 | Var. 107 | Var. 145 | Var. 183 | Var. 221 | Var. 259 | Var. 297 |
| 5.4 | Var. 32 | Var. 70 | Var. 108 | Var. 146 | Var. 184 | Var. 222 | Var. 260 | Var. 298 |
| 5.5 | Var. 33 | Var. 71 | Var. 109 | Var. 147 | Var. 185 | Var. 223 | Var. 261 | Var. 299 |
| 5.6 | Var. 34 | Var. 72 | Var. 110 | Var. 148 | Var. 186 | Var. 224 | Var. 262 | Var. 300 |
| 5.7 | Var. 35 | Var. 73 | Var. 111 | Var. 149 | Var. 187 | Var. 225 | Var. 263 | Var. 301 |
| 5.8 | Var. 36 | Var. 74 | Var. 112 | Var. 150 | Var. 188 | Var. 226 | Var. 264 | Var. 302 |
| 5.9 | Var. 37 | Var. 75 | Var. 113 | Var. 151 | Var. 189 | Var. 227 | Var. 265 | Var. 303 |
| 6 | Var. 38 | Var. 76 | Var. 114 | Var. 152 | Var. 190 | Var. 228 | Var. 266 | Var. 304 |

TABLE 2

Combinations of pH and final ethanol concentration useful
for low pH, high alcohol precipitation of a Cohn pool.
Final Ethanol Concentration [% (v/v)]

| pH | 22-29 | 23-29 | 24-29 | 25-29 | 20-28 | 21-28 | 22-28 |
|---|---|---|---|---|---|---|---|
| 5.0-6.0 | Var. 305 | Var. 343 | Var. 381 | Var. 419 | Var. 457 | Var. 495 | Var. 533 |
| 5.1-5.9 | Var. 306 | Var. 344 | Var. 382 | Var. 420 | Var. 458 | Var. 496 | Var. 534 |
| 5.2-5.8 | Var. 307 | Var. 345 | Var. 383 | Var. 421 | Var. 459 | Var. 497 | Var. 535 |
| 5.3-5.7 | Var. 308 | Var. 346 | Var. 384 | Var. 422 | Var. 460 | Var. 498 | Var. 536 |
| 5.4-5.6 | Var. 309 | Var. 347 | Var. 385 | Var. 423 | Var. 461 | Var. 499 | Var. 537 |
| 5.0 ± 0.2 | Var. 310 | Var. 348 | Var. 386 | Var. 424 | Var. 462 | Var. 500 | Var. 538 |
| 5.1 ± 0.2 | Var. 311 | Var. 349 | Var. 387 | Var. 425 | Var. 463 | Var. 501 | Var. 539 |
| 5.2 ± 0.2 | Var. 312 | Var. 350 | Var. 388 | Var. 426 | Var. 464 | Var. 502 | Var. 540 |
| 5.3 ± 0.2 | Var. 313 | Var. 351 | Var. 389 | Var. 427 | Var. 465 | Var. 503 | Var. 541 |
| 5.4 ± 0.2 | Var. 314 | Var. 352 | Var. 390 | Var. 428 | Var. 466 | Var. 504 | Var. 542 |
| 5.5 ± 0.2 | Var. 315 | Var. 353 | Var. 391 | Var. 429 | Var. 467 | Var. 505 | Var. 543 |
| 5.6 ± 0.2 | Var. 316 | Var. 354 | Var. 392 | Var. 430 | Var. 468 | Var. 506 | Var. 544 |
| 5.7 ± 0.2 | Var. 317 | Var. 355 | Var. 393 | Var. 431 | Var. 469 | Var. 507 | Var. 545 |
| 5.8 ± 0.2 | Var. 318 | Var. 356 | Var. 394 | Var. 432 | Var. 470 | Var. 508 | Var. 546 |
| 5.9 ± 0.2 | Var. 319 | Var. 357 | Var. 395 | Var. 433 | Var. 471 | Var. 509 | Var. 547 |
| 6.0 ± 0.2 | Var. 320 | Var. 358 | Var. 396 | Var. 434 | Var. 472 | Var. 510 | Var. 548 |
| 5.0 ± 0.1 | Var. 321 | Var. 359 | Var. 397 | Var. 435 | Var. 473 | Var. 511 | Var. 549 |
| 5.1 ± 0.1 | Var. 322 | Var. 360 | Var. 398 | Var. 436 | Var. 474 | Var. 512 | Var. 550 |
| 5.2 ± 0.1 | Var. 323 | Var. 361 | Var. 399 | Var. 437 | Var. 475 | Var. 513 | Var. 551 |
| 5.3 ± 0.1 | Var. 324 | Var. 362 | Var. 400 | Var. 438 | Var. 476 | Var. 514 | Var. 552 |
| 5.4 ± 0.1 | Var. 325 | Var. 363 | Var. 401 | Var. 439 | Var. 477 | Var. 515 | Var. 553 |
| 5.5 ± 0.1 | Var. 326 | Var. 364 | Var. 402 | Var. 440 | Var. 478 | Var. 516 | Var. 554 |
| 5.6 ± 0.1 | Var. 327 | Var. 365 | Var. 403 | Var. 441 | Var. 479 | Var. 517 | Var. 555 |

TABLE 2-continued

Combinations of pH and final ethanol concentration useful
for low pH, high alcohol precipitation of a Cohn pool.
Final Ethanol Concentration [% (v/v)]

| pH | 22-29 | 23-29 | 24-29 | 25-29 | 20-28 | 21-28 | 22-28 |
|---|---|---|---|---|---|---|---|
| 5.7 ± 0.1 | Var. 328 | Var. 366 | Var. 404 | Var. 442 | Var. 480 | Var. 518 | Var. 556 |
| 5.8 ± 0.1 | Var. 329 | Var. 367 | Var. 405 | Var. 443 | Var. 481 | Var. 519 | Var. 557 |
| 5.9 ± 0.1 | Var. 330 | Var. 368 | Var. 406 | Var. 444 | Var. 482 | Var. 520 | Var. 558 |
| 6.0 ± 0.1 | Var. 331 | Var. 369 | Var. 407 | Var. 445 | Var. 483 | Var. 521 | Var. 559 |
| 5 | Var. 332 | Var. 370 | Var. 408 | Var. 446 | Var. 484 | Var. 522 | Var. 560 |
| 5.1 | Var. 333 | Var. 371 | Var. 409 | Var. 447 | Var. 485 | Var. 523 | Var. 561 |
| 5.2 | Var. 334 | Var. 372 | Var. 410 | Var. 448 | Var. 486 | Var. 524 | Var. 562 |
| 5.3 | Var. 335 | Var. 373 | Var. 411 | Var. 449 | Var. 487 | Var. 525 | Var. 563 |
| 5.4 | Var. 336 | Var. 374 | Var. 412 | Var. 450 | Var. 488 | Var. 526 | Var. 564 |
| 5.5 | Var. 337 | Var. 375 | Var. 413 | Var. 451 | Var. 489 | Var. 527 | Var. 565 |
| 5.6 | Var. 338 | Var. 376 | Var. 414 | Var. 452 | Var. 490 | Var. 528 | Var. 566 |
| 5.7 | Var. 339 | Var. 377 | Var. 415 | Var. 453 | Var. 491 | Var. 529 | Var. 567 |
| 5.8 | Var. 340 | Var. 378 | Var. 416 | Var. 454 | Var. 492 | Var. 530 | Var. 568 |
| 5.9 | Var. 341 | Var. 379 | Var. 417 | Var. 455 | Var. 493 | Var. 531 | Var. 569 |
| 6 | Var. 342 | Var. 380 | Var. 418 | Var. 456 | Var. 494 | Var. 532 | Var. 570 |

TABLE 3

Combinations of pH and final ethanol concentration useful
for low pH, high alcohol precipitation of a Cohn pool.
Final Ethanol Concentration [% (v/v)]

| pH | 23-28 | 24-28 | 25-28 | 20-27 | 21-27 | 22-27 | 23-27 |
|---|---|---|---|---|---|---|---|
| 5.0-6.0 | Var. 571 | Var. 609 | Var. 647 | Var. 685 | Var. 723 | Var. 761 | Var. 799 |
| 5.1-5.9 | Var. 572 | Var. 610 | Var. 648 | Var. 686 | Var. 724 | Var. 762 | Var. 800 |
| 5.2-5.8 | Var. 573 | Var. 611 | Var. 649 | Var. 687 | Var. 725 | Var. 763 | Var. 801 |
| 5.3-5.7 | Var. 574 | Var. 612 | Var. 650 | Var. 688 | Var. 726 | Var. 764 | Var. 802 |
| 5.4-5.6 | Var. 575 | Var. 613 | Var. 651 | Var. 689 | Var. 727 | Var. 765 | Var. 803 |
| 5.0 ± 0.2 | Var. 576 | Var. 614 | Var. 652 | Var. 690 | Var. 728 | Var. 766 | Var. 804 |
| 5.1 ± 0.2 | Var. 577 | Var. 615 | Var. 653 | Var. 691 | Var. 729 | Var. 767 | Var. 805 |
| 5.2 ± 0.2 | Var. 578 | Var. 616 | Var. 654 | Var. 692 | Var. 730 | Var. 768 | Var. 806 |
| 5.3 ± 0.2 | Var. 579 | Var. 617 | Var. 655 | Var. 693 | Var. 731 | Var. 769 | Var. 807 |
| 5.4 ± 0.2 | Var. 580 | Var. 618 | Var. 656 | Var. 694 | Var. 732 | Var. 770 | Var. 808 |
| 5.5 ± 0.2 | Var. 581 | Var. 619 | Var. 657 | Var. 695 | Var. 733 | Var. 771 | Var. 809 |
| 5.6 ± 0.2 | Var. 582 | Var. 620 | Var. 658 | Var. 696 | Var. 734 | Var. 772 | Var. 810 |
| 5.7 ± 0.2 | Var. 583 | Var. 621 | Var. 659 | Var. 697 | Var. 735 | Var. 773 | Var. 811 |
| 5.8 ± 0.2 | Var. 584 | Var. 622 | Var. 660 | Var. 698 | Var. 736 | Var. 774 | Var. 812 |
| 5.9 ± 0.2 | Var. 585 | Var. 623 | Var. 661 | Var. 699 | Var. 737 | Var. 775 | Var. 813 |
| 6.0 ± 0.2 | Var. 586 | Var. 624 | Var. 662 | Var. 700 | Var. 738 | Var. 776 | Var. 814 |
| 5.0 ± 0.1 | Var. 587 | Var. 625 | Var. 663 | Var. 701 | Var. 739 | Var. 777 | Var. 815 |
| 5.1 ± 0.1 | Var. 588 | Var. 626 | Var. 664 | Var. 702 | Var. 740 | Var. 778 | Var. 816 |
| 5.2 ± 0.1 | Var. 589 | Var. 627 | Var. 665 | Var. 703 | Var. 741 | Var. 779 | Var. 817 |
| 5.3 ± 0.1 | Var. 590 | Var. 628 | Var. 666 | Var. 704 | Var. 742 | Var. 780 | Var. 818 |
| 5.4 ± 0.1 | Var. 591 | Var. 629 | Var. 667 | Var. 705 | Var. 743 | Var. 781 | Var. 819 |
| 5.5 ± 0.1 | Var. 592 | Var. 630 | Var. 668 | Var. 706 | Var. 744 | Var. 782 | Var. 820 |
| 5.6 ± 0.1 | Var. 593 | Var. 631 | Var. 669 | Var. 707 | Var. 745 | Var. 783 | Var. 821 |
| 5.7 ± 0.1 | Var. 594 | Var. 632 | Var. 670 | Var. 708 | Var. 746 | Var. 784 | Var. 822 |
| 5.8 ± 0.1 | Var. 595 | Var. 633 | Var. 671 | Var. 709 | Var. 747 | Var. 785 | Var. 823 |
| 5.9 ± 0.1 | Var. 596 | Var. 634 | Var. 672 | Var. 710 | Var. 748 | Var. 786 | Var. 824 |
| 6.0 ± 0.1 | Var. 597 | Var. 635 | Var. 673 | Var. 711 | Var. 749 | Var. 787 | Var. 825 |
| 5 | Var. 598 | Var. 636 | Var. 674 | Var. 712 | Var. 750 | Var. 788 | Var. 826 |
| 5.1 | Var. 599 | Var. 637 | Var. 675 | Var. 713 | Var. 751 | Var. 789 | Var. 827 |
| 5.2 | Var. 600 | Var. 638 | Var. 676 | Var. 714 | Var. 752 | Var. 790 | Var. 828 |
| 5.3 | Var. 601 | Var. 639 | Var. 677 | Var. 715 | Var. 753 | Var. 791 | Var. 829 |
| 5.4 | Var. 602 | Var. 640 | Var. 678 | Var. 716 | Var. 754 | Var. 792 | Var. 830 |
| 5.5 | Var. 603 | Var. 641 | Var. 679 | Var. 717 | Var. 755 | Var. 793 | Var. 831 |
| 5.6 | Var. 604 | Var. 642 | Var. 680 | Var. 718 | Var. 756 | Var. 794 | Var. 832 |
| 5.7 | Var. 605 | Var. 643 | Var. 681 | Var. 719 | Var. 757 | Var. 795 | Var. 833 |
| 5.8 | Var. 606 | Var. 644 | Var. 682 | Var. 720 | Var. 758 | Var. 796 | Var. 834 |
| 5.9 | Var. 607 | Var. 645 | Var. 683 | Var. 721 | Var. 759 | Var. 797 | Var. 835 |
| 6 | Var. 608 | Var. 646 | Var. 684 | Var. 722 | Var. 760 | Var. 798 | Var. 836 |

TABLE 4

Combinations of pH and final ethanol concentration useful
for low pH, high alcohol precipitation of a Cohn pool.
Final Ethanol Concentration [% (v/v)]

| pH | 24-27 | 25-27 | 20-26 | 21-26 | 22-26 | 23-26 | 24-26 | 25-26 |
|---|---|---|---|---|---|---|---|---|
| 5.0-6.0 | Var. 837 | Var. 875 | Var. 913 | Var. 951 | Var. 989 | Var. 1027 | Var. 1065 | Var. 1103 |
| 5.1-5.9 | Var. 838 | Var. 876 | Var. 914 | Var. 952 | Var. 990 | Var. 1028 | Var. 1066 | Var. 1104 |
| 5.2-5.8 | Var. 839 | Var. 877 | Var. 915 | Var. 953 | Var. 991 | Var. 1029 | Var. 1067 | Var. 1105 |
| 5.3-5.7 | Var. 840 | Var. 878 | Var. 916 | Var. 954 | Var. 992 | Var. 1030 | Var. 1068 | Var. 1106 |
| 5.4-5.6 | Var. 841 | Var. 879 | Var. 917 | Var. 955 | Var. 993 | Var. 1031 | Var. 1069 | Var. 1107 |
| 5.0 ± 0.2 | Var. 842 | Var. 880 | Var. 918 | Var. 956 | Var. 994 | Var. 1032 | Var. 1070 | Var. 1108 |
| 5.1 ± 0.2 | Var. 843 | Var. 881 | Var. 919 | Var. 957 | Var. 995 | Var. 1033 | Var. 1071 | Var. 1109 |
| 5.2 ± 0.2 | Var. 844 | Var. 882 | Var. 920 | Var. 958 | Var. 996 | Var. 1034 | Var. 1072 | Var. 1110 |
| 5.3 ± 0.2 | Var. 845 | Var. 883 | Var. 921 | Var. 959 | Var. 997 | Var. 1035 | Var. 1073 | Var. 1111 |
| 5.4 ± 0.2 | Var. 846 | Var. 884 | Var. 922 | Var. 960 | Var. 998 | Var. 1036 | Var. 1074 | Var. 1112 |
| 5.5 ± 0.2 | Var. 847 | Var. 885 | Var. 923 | Var. 961 | Var. 999 | Var. 1037 | Var. 1075 | Var. 1113 |
| 5.6 ± 0.2 | Var. 848 | Var. 886 | Var. 924 | Var. 962 | Var. 1000 | Var. 1038 | Var. 1076 | Var. 1114 |
| 5.7 ± 0.2 | Var. 849 | Var. 887 | Var. 925 | Var. 963 | Var. 1001 | Var. 1039 | Var. 1077 | Var. 1115 |
| 5.8 ± 0.2 | Var. 850 | Var. 888 | Var. 926 | Var. 964 | Var. 1002 | Var. 1040 | Var. 1078 | Var. 1116 |
| 5.9 ± 0.2 | Var. 851 | Var. 889 | Var. 927 | Var. 965 | Var. 1003 | Var. 1041 | Var. 1079 | Var. 1117 |
| 6.0 ± 0.2 | Var. 852 | Var. 890 | Var. 928 | Var. 966 | Var. 1004 | Var. 1042 | Var. 1080 | Var. 1118 |
| 5.0 ± 0.1 | Var. 853 | Var. 891 | Var. 929 | Var. 967 | Var. 1005 | Var. 1043 | Var. 1081 | Var. 1119 |
| 5.1 ± 0.1 | Var. 854 | Var. 892 | Var. 930 | Var. 968 | Var. 1006 | Var. 1044 | Var. 1082 | Var. 1120 |
| 5.2 ± 0.1 | Var. 855 | Var. 893 | Var. 931 | Var. 969 | Var. 1007 | Var. 1045 | Var. 1083 | Var. 1121 |
| 5.3 ± 0.1 | Var. 856 | Var. 894 | Var. 932 | Var. 970 | Var. 1008 | Var. 1046 | Var. 1084 | Var. 1122 |
| 5.4 ± 0.1 | Var. 857 | Var. 895 | Var. 933 | Var. 971 | Var. 1009 | Var. 1047 | Var. 1085 | Var. 1123 |
| 5.5 ± 0.1 | Var. 858 | Var. 896 | Var. 934 | Var. 972 | Var. 1010 | Var. 1048 | Var. 1086 | Var. 1124 |
| 5.6 ± 0.1 | Var. 859 | Var. 897 | Var. 935 | Var. 973 | Var. 1011 | Var. 1049 | Var. 1087 | Var. 1125 |
| 5.7 ± 0.1 | Var. 860 | Var. 898 | Var. 936 | Var. 974 | Var. 1012 | Var. 1050 | Var. 1088 | Var. 1126 |
| 5.8 ± 0.1 | Var. 861 | Var. 899 | Var. 937 | Var. 975 | Var. 1013 | Var. 1051 | Var. 1089 | Var. 1127 |
| 5.9 ± 0.1 | Var. 862 | Var. 900 | Var. 938 | Var. 976 | Var. 1014 | Var. 1052 | Var. 1090 | Var. 1128 |
| 6.0 ± 0.1 | Var. 863 | Var. 901 | Var. 939 | Var. 977 | Var. 1015 | Var. 1053 | Var. 1091 | Var. 1129 |
| 5 | Var. 864 | Var. 902 | Var. 940 | Var. 978 | Var. 1016 | Var. 1054 | Var. 1092 | Var. 1130 |
| 5.1 | Var. 865 | Var. 903 | Var. 941 | Var. 979 | Var. 1017 | Var. 1055 | Var. 1093 | Var. 1131 |
| 5.2 | Var. 866 | Var. 904 | Var. 942 | Var. 980 | Var. 1018 | Var. 1056 | Var. 1094 | Var. 1132 |
| 5.3 | Var. 867 | Var. 905 | Var. 943 | Var. 981 | Var. 1019 | Var. 1057 | Var. 1095 | Var. 1133 |
| 5.4 | Var. 868 | Var. 906 | Var. 944 | Var. 982 | Var. 1020 | Var. 1058 | Var. 1096 | Var. 1134 |
| 5.5 | Var. 869 | Var. 907 | Var. 945 | Var. 983 | Var. 1021 | Var. 1059 | Var. 1097 | Var. 1135 |
| 5.6 | Var. 870 | Var. 908 | Var. 946 | Var. 984 | Var. 1022 | Var. 1060 | Var. 1098 | Var. 1136 |
| 5.7 | Var. 871 | Var. 909 | Var. 947 | Var. 985 | Var. 1023 | Var. 1061 | Var. 1099 | Var. 1137 |
| 5.8 | Var. 872 | Var. 910 | Var. 948 | Var. 986 | Var. 1024 | Var. 1062 | Var. 1100 | Var. 1138 |
| 5.9 | Var. 873 | Var. 911 | Var. 949 | Var. 987 | Var. 1025 | Var. 1063 | Var. 1101 | Var. 1139 |
| 6 | Var. 874 | Var. 912 | Var. 950 | Var. 988 | Var. 1026 | Var. 1064 | Var. 1102 | Var. 1140 |

TABLE 5

Combinations of pH and final ethanol concentration useful
for low pH, high alcohol precipitation of a Cohn pool.
Final Ethanol Concentration [% (v/v)]

| pH | 20-25 | 21-25 | 22-25 | 23-25 | 24-25 | 20 ± 1 | 21 ± 1 | 22 ± 1 |
|---|---|---|---|---|---|---|---|---|
| 5.0-6.0 | Var. 1141 | Var. 1179 | Var. 1217 | Var. 1255 | Var. 1293 | Var. 1331 | Var. 1369 | Var. 1407 |
| 5.1-5.9 | Var. 1142 | Var. 1180 | Var. 1218 | Var. 1256 | Var. 1294 | Var. 1332 | Var. 1370 | Var. 1408 |
| 5.2-5.8 | Var. 1143 | Var. 1181 | Var. 1219 | Var. 1257 | Var. 1295 | Var. 1333 | Var. 1371 | Var. 1409 |
| 5.3-5.7 | Var. 1144 | Var. 1182 | Var. 1220 | Var. 1258 | Var. 1296 | Var. 1334 | Var. 1372 | Var. 1410 |
| 5.4-5.6 | Var. 1145 | Var. 1183 | Var. 1221 | Var. 1259 | Var. 1297 | Var. 1335 | Var. 1373 | Var. 1411 |
| 5.0 ± 0.2 | Var. 1146 | Var. 1184 | Var. 1222 | Var. 1260 | Var. 1298 | Var. 1336 | Var. 1374 | Var. 1412 |
| 5.1 ± 0.2 | Var. 1147 | Var. 1185 | Var. 1223 | Var. 1261 | Var. 1299 | Var. 1337 | Var. 1375 | Var. 1413 |
| 5.2 ± 0.2 | Var. 1148 | Var. 1186 | Var. 1224 | Var. 1262 | Var. 1300 | Var. 1338 | Var. 1376 | Var. 1414 |
| 5.3 ± 0.2 | Var. 1149 | Var. 1187 | Var. 1225 | Var. 1263 | Var. 1301 | Var. 1339 | Var. 1377 | Var. 1415 |
| 5.4 ± 0.2 | Var. 1150 | Var. 1188 | Var. 1226 | Var. 1264 | Var. 1302 | Var. 1340 | Var. 1378 | Var. 1416 |
| 5.5 ± 0.2 | Var. 1151 | Var. 1189 | Var. 1227 | Var. 1265 | Var. 1303 | Var. 1341 | Var. 1379 | Var. 1417 |
| 5.6 ± 0.2 | Var. 1152 | Var. 1190 | Var. 1228 | Var. 1266 | Var. 1304 | Var. 1342 | Var. 1380 | Var. 1418 |
| 5.7 ± 0.2 | Var. 1153 | Var. 1191 | Var. 1229 | Var. 1267 | Var. 1305 | Var. 1343 | Var. 1381 | Var. 1419 |
| 5.8 ± 0.2 | Var. 1154 | Var. 1192 | Var. 1230 | Var. 1268 | Var. 1306 | Var. 1344 | Var. 1382 | Var. 1420 |
| 5.9 ± 0.2 | Var. 1155 | Var. 1193 | Var. 1231 | Var. 1269 | Var. 1307 | Var. 1345 | Var. 1383 | Var. 1421 |
| 6.0 ± 0.2 | Var. 1156 | Var. 1194 | Var. 1232 | Var. 1270 | Var. 1308 | Var. 1346 | Var. 1384 | Var. 1422 |
| 5.0 ± 0.1 | Var. 1157 | Var. 1195 | Var. 1233 | Var. 1271 | Var. 1309 | Var. 1347 | Var. 1385 | Var. 1423 |
| 5.1 ± 0.1 | Var. 1158 | Var. 1196 | Var. 1234 | Var. 1272 | Var. 1310 | Var. 1348 | Var. 1386 | Var. 1424 |
| 5.2 ± 0.1 | Var. 1159 | Var. 1197 | Var. 1235 | Var. 1273 | Var. 1311 | Var. 1349 | Var. 1387 | Var. 1425 |
| 5.3 ± 0.1 | Var. 1160 | Var. 1198 | Var. 1236 | Var. 1274 | Var. 1312 | Var. 1350 | Var. 1388 | Var. 1426 |
| 5.4 ± 0.1 | Var. 1161 | Var. 1199 | Var. 1237 | Var. 1275 | Var. 1313 | Var. 1351 | Var. 1389 | Var. 1427 |
| 5.5 ± 0.1 | Var. 1162 | Var. 1200 | Var. 1238 | Var. 1276 | Var. 1314 | Var. 1352 | Var. 1390 | Var. 1428 |
| 5.6 ± 0.1 | Var. 1163 | Var. 1201 | Var. 1239 | Var. 1277 | Var. 1315 | Var. 1353 | Var. 1391 | Var. 1429 |

TABLE 5-continued

Combinations of pH and final ethanol concentration useful
for low pH, high alcohol precipitation of a Cohn pool.
Final Ethanol Concentration [% (v/v)]

| pH | 20-25 | 21-25 | 22-25 | 23-25 | 24-25 | 20 ± 1 | 21 ± 1 | 22 ± 1 |
|---|---|---|---|---|---|---|---|---|
| 5.7 ± 0.1 | Var. 1164 | Var. 1202 | Var. 1240 | Var. 1278 | Var. 1316 | Var. 1354 | Var. 1392 | Var. 1430 |
| 5.8 ± 0.1 | Var. 1165 | Var. 1203 | Var. 1241 | Var. 1279 | Var. 1317 | Var. 1355 | Var. 1393 | Var. 1431 |
| 5.9 ± 0.1 | Var. 1166 | Var. 1204 | Var. 1242 | Var. 1280 | Var. 1318 | Var. 1356 | Var. 1394 | Var. 1432 |
| 6.0 ± 0.1 | Var. 1167 | Var. 1205 | Var. 1243 | Var. 1281 | Var. 1319 | Var. 1357 | Var. 1395 | Var. 1433 |
| 5 | Var. 1168 | Var. 1206 | Var. 1244 | Var. 1282 | Var. 1320 | Var. 1358 | Var. 1396 | Var. 1434 |
| 5.1 | Var. 1169 | Var. 1207 | Var. 1245 | Var. 1283 | Var. 1321 | Var. 1359 | Var. 1397 | Var. 1435 |
| 5.2 | Var. 1170 | Var. 1208 | Var. 1246 | Var. 1284 | Var. 1322 | Var. 1360 | Var. 1398 | Var. 1436 |
| 5.3 | Var. 1171 | Var. 1209 | Var. 1247 | Var. 1285 | Var. 1323 | Var. 1361 | Var. 1399 | Var. 1437 |
| 5.4 | Var. 1172 | Var. 1210 | Var. 1248 | Var. 1286 | Var. 1324 | Var. 1362 | Var. 1400 | Var. 1438 |
| 5.5 | Var. 1173 | Var. 1211 | Var. 1249 | Var. 1287 | Var. 1325 | Var. 1363 | Var. 1401 | Var. 1439 |
| 5.6 | Var. 1174 | Var. 1212 | Var. 1250 | Var. 1288 | Var. 1326 | Var. 1364 | Var. 1402 | Var. 1440 |
| 5.7 | Var. 1175 | Var. 1213 | Var. 1251 | Var. 1289 | Var. 1327 | Var. 1365 | Var. 1403 | Var. 1441 |
| 5.8 | Var. 1176 | Var. 1214 | Var. 1252 | Var. 1290 | Var. 1328 | Var. 1366 | Var. 1404 | Var. 1442 |
| 5.9 | Var. 1177 | Var. 1215 | Var. 1253 | Var. 1291 | Var. 1329 | Var. 1367 | Var. 1405 | Var. 1443 |
| 6 | Var. 1178 | Var. 1216 | Var. 1254 | Var. 1292 | Var. 1330 | Var. 1368 | Var. 1406 | Var. 1444 |

TABLE 6

Combinations of pH and final ethanol concentration useful
for low pH, high alcohol precipitation of a Cohn pool.
Final Ethanol Concentration [% (v/v)]

| pH | 23 ± 1 | 24 ± 1 | 25 ± 1 | 26 ± 1 | 27 ± 1 | 28 ± 1 | 29 ± 1 | 30 ± 1 |
|---|---|---|---|---|---|---|---|---|
| 5.0-6.0 | Var. 1445 | Var. 1483 | Var. 1521 | Var. 1559 | Var. 1597 | Var. 1635 | Var. 1673 | Var. 1711 |
| 5.1-5.9 | Var. 1446 | Var. 1484 | Var. 1522 | Var. 1560 | Var. 1598 | Var. 1636 | Var. 1674 | Var. 1712 |
| 5.2-5.8 | Var. 1447 | Var. 1485 | Var. 1523 | Var. 1561 | Var. 1599 | Var. 1637 | Var. 1675 | Var. 1713 |
| 5.3-5.7 | Var. 1448 | Var. 1486 | Var. 1524 | Var. 1562 | Var. 1600 | Var. 1638 | Var. 1676 | Var. 1714 |
| 5.4-5.6 | Var. 1449 | Var. 1487 | Var. 1525 | Var. 1563 | Var. 1601 | Var. 1639 | Var. 1677 | Var. 1715 |
| 5.0 ± 0.2 | Var. 1450 | Var. 1488 | Var. 1526 | Var. 1564 | Var. 1602 | Var. 1640 | Var. 1678 | Var. 1716 |
| 5.1 ± 0.2 | Var. 1451 | Var. 1489 | Var. 1527 | Var. 1565 | Var. 1603 | Var. 1641 | Var. 1679 | Var. 1717 |
| 5.2 ± 0.2 | Var. 1452 | Var. 1490 | Var. 1528 | Var. 1566 | Var. 1604 | Var. 1642 | Var. 1680 | Var. 1718 |
| 5.3 ± 0.2 | Var. 1453 | Var. 1491 | Var. 1529 | Var. 1567 | Var. 1605 | Var. 1643 | Var. 1681 | Var. 1719 |
| 5.4 ± 0.2 | Var. 1454 | Var. 1492 | Var. 1530 | Var. 1568 | Var. 1606 | Var. 1644 | Var. 1682 | Var. 1720 |
| 5.5 ± 0.2 | Var. 1455 | Var. 1493 | Var. 1531 | Var. 1569 | Var. 1607 | Var. 1645 | Var. 1683 | Var. 1721 |
| 5.6 ± 0.2 | Var. 1456 | Var. 1494 | Var. 1532 | Var. 1570 | Var. 1608 | Var. 1646 | Var. 1684 | Var. 1722 |
| 5.7 ± 0.2 | Var. 1457 | Var. 1495 | Var. 1533 | Var. 1571 | Var. 1609 | Var. 1647 | Var. 1685 | Var. 1723 |
| 5.8 ± 0.2 | Var. 1458 | Var. 1496 | Var. 1534 | Var. 1572 | Var. 1610 | Var. 1648 | Var. 1686 | Var. 1724 |
| 5.9 ± 0.2 | Var. 1459 | Var. 1497 | Var. 1535 | Var. 1573 | Var. 1611 | Var. 1649 | Var. 1687 | Var. 1725 |
| 6.0 ± 0.2 | Var. 1460 | Var. 1498 | Var. 1536 | Var. 1574 | Var. 1612 | Var. 1650 | Var. 1688 | Var. 1726 |
| 5.0 ± 0.1 | Var. 1461 | Var. 1499 | Var. 1537 | Var. 1575 | Var. 1613 | Var. 1651 | Var. 1689 | Var. 1727 |
| 5.1 ± 0.1 | Var. 1462 | Var. 1500 | Var. 1538 | Var. 1576 | Var. 1614 | Var. 1652 | Var. 1690 | Var. 1728 |
| 5.2 ± 0.1 | Var. 1463 | Var. 1501 | Var. 1539 | Var. 1577 | Var. 1615 | Var. 1653 | Var. 1691 | Var. 1729 |
| 5.3 ± 0.1 | Var. 1464 | Var. 1502 | Var. 1540 | Var. 1578 | Var. 1616 | Var. 1654 | Var. 1692 | Var. 1730 |
| 5.4 ± 0.1 | Var. 1465 | Var. 1503 | Var. 1541 | Var. 1579 | Var. 1617 | Var. 1655 | Var. 1693 | Var. 1731 |
| 5.5 ± 0.1 | Var. 1466 | Var. 1504 | Var. 1542 | Var. 1580 | Var. 1618 | Var. 1656 | Var. 1694 | Var. 1732 |
| 5.6 ± 0.1 | Var. 1467 | Var. 1505 | Var. 1543 | Var. 1581 | Var. 1619 | Var. 1657 | Var. 1695 | Var. 1733 |
| 5.7 ± 0.1 | Var. 1468 | Var. 1506 | Var. 1544 | Var. 1582 | Var. 1620 | Var. 1658 | Var. 1696 | Var. 1734 |
| 5.8 ± 0.1 | Var. 1469 | Var. 1507 | Var. 1545 | Var. 1583 | Var. 1621 | Var. 1659 | Var. 1697 | Var. 1735 |
| 5.9 ± 0.1 | Var. 1470 | Var. 1508 | Var. 1546 | Var. 1584 | Var. 1622 | Var. 1660 | Var. 1698 | Var. 1736 |
| 6.0 ± 0.1 | Var. 1471 | Var. 1509 | Var. 1547 | Var. 1585 | Var. 1623 | Var. 1661 | Var. 1699 | Var. 1737 |
| 5 | Var. 1472 | Var. 1510 | Var. 1548 | Var. 1586 | Var. 1624 | Var. 1662 | Var. 1700 | Var. 1738 |
| 5.1 | Var. 1473 | Var. 1511 | Var. 1549 | Var. 1587 | Var. 1625 | Var. 1663 | Var. 1701 | Var. 1739 |
| 5.2 | Var. 1474 | Var. 1512 | Var. 1550 | Var. 1588 | Var. 1626 | Var. 1664 | Var. 1702 | Var. 1740 |
| 5.3 | Var. 1475 | Var. 1513 | Var. 1551 | Var. 1589 | Var. 1627 | Var. 1665 | Var. 1703 | Var. 1741 |
| 5.4 | Var. 1476 | Var. 1514 | Var. 1552 | Var. 1590 | Var. 1628 | Var. 1666 | Var. 1704 | Var. 1742 |
| 5.5 | Var. 1477 | Var. 1515 | Var. 1553 | Var. 1591 | Var. 1629 | Var. 1667 | Var. 1705 | Var. 1743 |
| 5.6 | Var. 1478 | Var. 1516 | Var. 1554 | Var. 1592 | Var. 1630 | Var. 1668 | Var. 1706 | Var. 1744 |
| 5.7 | Var. 1479 | Var. 1517 | Var. 1555 | Var. 1593 | Var. 1631 | Var. 1669 | Var. 1707 | Var. 1745 |
| 5.8 | Var. 1480 | Var. 1518 | Var. 1556 | Var. 1594 | Var. 1632 | Var. 1670 | Var. 1708 | Var. 1746 |
| 5.9 | Var. 1481 | Var. 1519 | Var. 1557 | Var. 1595 | Var. 1633 | Var. 1671 | Var. 1709 | Var. 1747 |
| 6 | Var. 1482 | Var. 1520 | Var. 1558 | Var. 1596 | Var. 1634 | Var. 1672 | Var. 1710 | Var. 1748 |

TABLE 7

Combinations of pH and final ethanol concentration useful for low pH, high alcohol precipitation of a Cohn pool.
Final Ethanol Concentration [% (v/v)]

| pH | 20 | 21 | 22 | 23 | 24 | 25 | 26 | 27 |
|---|---|---|---|---|---|---|---|---|
| 5.0-6.0 | Var. 1749 | Var. 1787 | Var. 1825 | Var. 1863 | Var. 1901 | Var. 1939 | Var. 1977 | Var. 2015 |
| 5.1-5.9 | Var. 1750 | Var. 1788 | Var. 1826 | Var. 1864 | Var. 1902 | Var. 1940 | Var. 1978 | Var. 2016 |
| 5.2-5.8 | Var. 1751 | Var. 1789 | Var. 1827 | Var. 1865 | Var. 1903 | Var. 1941 | Var. 1979 | Var. 2017 |
| 5.3-5.7 | Var. 1752 | Var. 1790 | Var. 1828 | Var. 1866 | Var. 1904 | Var. 1942 | Var. 1980 | Var. 2018 |
| 5.4-5.6 | Var. 1753 | Var. 1791 | Var. 1829 | Var. 1867 | Var. 1905 | Var. 1943 | Var. 1981 | Var. 2019 |
| 5.0 ± 0.2 | Var. 1754 | Var. 1792 | Var. 1830 | Var. 1868 | Var. 1906 | Var. 1944 | Var. 1982 | Var. 2020 |
| 5.1 ± 0.2 | Var. 1755 | Var. 1793 | Var. 1831 | Var. 1869 | Var. 1907 | Var. 1945 | Var. 1983 | Var. 2021 |
| 5.2 ± 0.2 | Var. 1756 | Var. 1794 | Var. 1832 | Var. 1870 | Var. 1908 | Var. 1946 | Var. 1984 | Var. 2022 |
| 5.3 ± 0.2 | Var. 1757 | Var. 1795 | Var. 1833 | Var. 1871 | Var. 1909 | Var. 1947 | Var. 1985 | Var. 2023 |
| 5.4 ± 0.2 | Var. 1758 | Var. 1796 | Var. 1834 | Var. 1872 | Var. 1910 | Var. 1948 | Var. 1986 | Var. 2024 |
| 5.5 ± 0.2 | Var. 1759 | Var. 1797 | Var. 1835 | Var. 1873 | Var. 1911 | Var. 1949 | Var. 1987 | Var. 2025 |
| 5.6 ± 0.2 | Var. 1760 | Var. 1798 | Var. 1836 | Var. 1874 | Var. 1912 | Var. 1950 | Var. 1988 | Var. 2026 |
| 5.7 ± 0.2 | Var. 1761 | Var. 1799 | Var. 1837 | Var. 1875 | Var. 1913 | Var. 1951 | Var. 1989 | Var. 2027 |
| 5.8 ± 0.2 | Var. 1762 | Var. 1800 | Var. 1838 | Var. 1876 | Var. 1914 | Var. 1952 | Var. 1990 | Var. 2028 |
| 5.9 ± 0.2 | Var. 1763 | Var. 1801 | Var. 1839 | Var. 1877 | Var. 1915 | Var. 1953 | Var. 1991 | Var. 2029 |
| 6.0 ± 0.2 | Var. 1764 | Var. 1802 | Var. 1840 | Var. 1878 | Var. 1916 | Var. 1954 | Var. 1992 | Var. 2030 |
| 5.0 ± 0.1 | Var. 1765 | Var. 1803 | Var. 1841 | Var. 1879 | Var. 1917 | Var. 1955 | Var. 1993 | Var. 2031 |
| 5.1 ± 0.1 | Var. 1766 | Var. 1804 | Var. 1842 | Var. 1880 | Var. 1918 | Var. 1956 | Var. 1994 | Var. 2032 |
| 5.2 ± 0.1 | Var. 1767 | Var. 1805 | Var. 1843 | Var. 1881 | Var. 1919 | Var. 1957 | Var. 1995 | Var. 2033 |
| 5.3 ± 0.1 | Var. 1768 | Var. 1806 | Var. 1844 | Var. 1882 | Var. 1920 | Var. 1958 | Var. 1996 | Var. 2034 |
| 5.4 ± 0.1 | Var. 1769 | Var. 1807 | Var. 1845 | Var. 1883 | Var. 1921 | Var. 1959 | Var. 1997 | Var. 2035 |
| 5.5 ± 0.1 | Var. 1770 | Var. 1808 | Var. 1846 | Var. 1884 | Var. 1922 | Var. 1960 | Var. 1998 | Var. 2036 |
| 5.6 ± 0.1 | Var. 1771 | Var. 1809 | Var. 1847 | Var. 1885 | Var. 1923 | Var. 1961 | Var. 1999 | Var. 2037 |
| 5.7 ± 0.1 | Var. 1772 | Var. 1810 | Var. 1848 | Var. 1886 | Var. 1924 | Var. 1962 | Var. 2000 | Var. 2038 |
| 5.8 ± 0.1 | Var. 1773 | Var. 1811 | Var. 1849 | Var. 1887 | Var. 1925 | Var. 1963 | Var. 2001 | Var. 2039 |
| 5.9 ± 0.1 | Var. 1774 | Var. 1812 | Var. 1850 | Var. 1888 | Var. 1926 | Var. 1964 | Var. 2002 | Var. 2040 |
| 6.0 ± 0.1 | Var. 1775 | Var. 1813 | Var. 1851 | Var. 1889 | Var. 1927 | Var. 1965 | Var. 2003 | Var. 2041 |
| 5 | Var. 1776 | Var. 1814 | Var. 1852 | Var. 1890 | Var. 1928 | Var. 1966 | Var. 2004 | Var. 2042 |
| 5.1 | Var. 1777 | Var. 1815 | Var. 1853 | Var. 1891 | Var. 1929 | Var. 1967 | Var. 2005 | Var. 2043 |
| 5.2 | Var. 1778 | Var. 1816 | Var. 1854 | Var. 1892 | Var. 1930 | Var. 1968 | Var. 2006 | Var. 2044 |
| 5.3 | Var. 1779 | Var. 1817 | Var. 1855 | Var. 1893 | Var. 1931 | Var. 1969 | Var. 2007 | Var. 2045 |
| 5.4 | Var. 1780 | Var. 1818 | Var. 1856 | Var. 1894 | Var. 1932 | Var. 1970 | Var. 2008 | Var. 2046 |
| 5.5 | Var. 1781 | Var. 1819 | Var. 1857 | Var. 1895 | Var. 1933 | Var. 1971 | Var. 2009 | Var. 2047 |
| 5.6 | Var. 1782 | Var. 1820 | Var. 1858 | Var. 1896 | Var. 1934 | Var. 1972 | Var. 2010 | Var. 2048 |
| 5.7 | Var. 1783 | Var. 1821 | Var. 1859 | Var. 1897 | Var. 1935 | Var. 1973 | Var. 2011 | Var. 2049 |
| 5.8 | Var. 1784 | Var. 1822 | Var. 1860 | Var. 1898 | Var. 1936 | Var. 1974 | Var. 2012 | Var. 2050 |
| 5.9 | Var. 1785 | Var. 1823 | Var. 1861 | Var. 1899 | Var. 1937 | Var. 1975 | Var. 2013 | Var. 2051 |
| 6 | Var. 1786 | Var. 1824 | Var. 1862 | Var. 1900 | Var. 1938 | Var. 1976 | Var. 2014 | Var. 2052 |

TABLE 8

Combinations of pH and final ethanol concentration useful for low pH, high alcohol precipitation of a Cohn pool.
Final Ethanol Concentration [% (v/v)]

| pH | 28 | 29 | 30 |
|---|---|---|---|
| 5.0-6.0 | Var. 2053 | Var. 2091 | Var. 2129 |
| 5.1-5.9 | Var. 2054 | Var. 2092 | Var. 2130 |
| 5.2-5.8 | Var. 2055 | Var. 2093 | Var. 2131 |
| 5.3-5.7 | Var. 2056 | Var. 2094 | Var. 2132 |
| 5.4-5.6 | Var. 2057 | Var. 2095 | Var. 2133 |
| 5.0 ± 0.2 | Var. 2058 | Var. 2096 | Var. 2134 |
| 5.1 ± 0.2 | Var. 2059 | Var. 2097 | Var. 2135 |
| 5.2 ± 0.2 | Var. 2060 | Var. 2098 | Var. 2136 |
| 5.3 ± 0.2 | Var. 2061 | Var. 2099 | Var. 2137 |
| 5.4 ± 0.2 | Var. 2062 | Var. 2100 | Var. 2138 |
| 5.5 ± 0.2 | Var. 2063 | Var. 2101 | Var. 2139 |
| 5.6 ± 0.2 | Var. 2064 | Var. 2102 | Var. 2140 |
| 5.7 ± 0.2 | Var. 2065 | Var. 2103 | Var. 2141 |
| 5.8 ± 0.2 | Var. 2066 | Var. 2104 | Var. 2142 |
| 5.9 ± 0.2 | Var. 2067 | Var. 2105 | Var. 2143 |
| 6.0 ± 0.2 | Var. 2068 | Var. 2106 | Var. 2144 |
| 5.0 ± 0.1 | Var. 2069 | Var. 2107 | Var. 2145 |
| 5.1 ± 0.1 | Var. 2070 | Var. 2108 | Var. 2146 |
| 5.2 ± 0.1 | Var. 2071 | Var. 2109 | Var. 2147 |
| 5.3 ± 0.1 | Var. 2072 | Var. 2110 | Var. 2148 |
| 5.4 ± 0.1 | Var. 2073 | Var. 2111 | Var. 2149 |
| 5.5 ± 0.1 | Var. 2074 | Var. 2112 | Var. 2150 |
| 5.6 ± 0.1 | Var. 2075 | Var. 2113 | Var. 2151 |
| 5.7 ± 0.1 | Var. 2076 | Var. 2114 | Var. 2152 |
| 5.8 ± 0.1 | Var. 2077 | Var. 2115 | Var. 2153 |
| 5.9 ± 0.1 | Var. 2078 | Var. 2116 | Var. 2154 |
| 6.0 ± 0.1 | Var. 2079 | Var. 2117 | Var. 2155 |
| 5 | Var. 2080 | Var. 2118 | Var. 2156 |
| 5.1 | Var. 2081 | Var. 2119 | Var. 2157 |
| 5.2 | Var. 2082 | Var. 2120 | Var. 2158 |
| 5.3 | Var. 2083 | Var. 2121 | Var. 2159 |
| 5.4 | Var. 2084 | Var. 2122 | Var. 2160 |
| 5.5 | Var. 2085 | Var. 2123 | Var. 2161 |
| 5.6 | Var. 2086 | Var. 2124 | Var. 2162 |
| 5.7 | Var. 2087 | Var. 2125 | Var. 2163 |
| 5.8 | Var. 2088 | Var. 2126 | Var. 2164 |
| 5.9 | Var. 2089 | Var. 2127 | Var. 2165 |
| 6 | Var. 2090 | Var. 2128 | Var. 2166 |

Accordingly, in one embodiment, the present invention provides a method for fractionating blood proteins in a plasma sample, the method comprising the steps of: precipitating immunoglobulins and A1PI in a first precipitation step by adding ethanol to a Cohn pool to a final concentration of between 20% and 30% at a pH from 5.0 to 6.0 to form a first precipitate and a first supernatant; separating the first precipitate from the first supernatant; wherein the first supernatant contains at least 75% of the albumin content of the Cohn pool. In one embodiment, ethanol is admixed with the Cohn pool to a final concentration of 25±3% (v/v).

In one embodiment of the methods provided herein, at least 90% of the immunoglobulin content of the starting Cohn pool is precipitated in the initial precipitation reaction. In a preferred embodiment, at least 95% of the immunoglobulin content of the starting Cohn pool is precipitated in the initial precipitation reaction. In a more preferred embodiment, at least 99% of the immunoglobulin content of the starting Cohn pool is precipitated in the initial precipitation reaction. In certain embodiments, at least 90%, 91%, 92%, 93%, 94%, 95%, 96%, 97%, 98%, 99%, or more of the immunoglobulin content of the starting Cohn pool is precipitated in the initial precipitation reaction. In a more specific embodiment, the immunoglobulin content of the starting Cohn pool refers to the IgG, IgA, and IgM content of the starting Cohn pool. In one specific embodiment, the immunoglobulin content of the starting Cohn pool refers to the IgG content of the starting Cohn pool.

In one embodiment of the methods provided herein, at least 80% of the alpha-1-antitrypsin (A1PI) content of the starting Cohn pool is precipitated in the initial precipitation reaction. In a preferred embodiment, at least 90% of the A1PI content of the starting Cohn pool is precipitated in the initial precipitation reaction. In a more preferred embodiment, at least 95% of the A1PI content of the starting Cohn pool is precipitated in the initial precipitation reaction. In certain embodiments, at least 80%, 81%, 82%, 83%, 84%, 85%, 86%, 87%, 88%, 89%, 90%, 91%, 92%, 93%, 94%, 95%, 96%, 97%, 98%, 99%, or more of the A1PI content of the starting Cohn pool is precipitated in the initial precipitation reaction.

In one embodiment of the methods provided herein, at least 70% of the Factor H content of the starting Cohn pool is precipitated in the initial precipitation reaction. In a preferred embodiment, at least 80% of the Factor H content of the starting Cohn pool is precipitated in the initial precipitation reaction. In a preferred embodiment, at least 90% of the Factor H content of the starting Cohn pool is precipitated in the initial precipitation reaction. In a more preferred embodiment, at least 95% of the Factor H content of the starting Cohn pool is precipitated in the initial precipitation reaction. In certain embodiments, at least 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or more of the Factor H content of the starting Cohn pool is precipitated in the initial precipitation reaction.

In one embodiment of the methods provided herein, at least 70% of the inter-alpha-inhibitor (IaIp) content of the starting Cohn pool is precipitated in the initial precipitation reaction. In a preferred embodiment, at least 80% of the IaIp content of the starting Cohn pool is precipitated in the initial precipitation reaction. In a preferred embodiment, at least 90% of the IaIp content of the starting Cohn pool is precipitated in the initial precipitation reaction. In a more preferred embodiment, at least 95% of the IaIp content of the starting Cohn pool is precipitated in the initial precipitation reaction. In certain embodiments, at least 70%, 71%, 72%, 73%, 74%, 75%, 76%, 77%, 78%, 79%, 81%, 82%, 83%, 84%, 85%, 86%, 87%, 88%, 89%, 90%, 91%, 92%, 93%, 94%, 95%, 96%, 97%, 98%, 99%, or more of the IaIp content of the starting Cohn pool is precipitated in the initial precipitation reaction.

Accordingly, in one embodiment, the present invention provides a method for fractionating blood proteins in a Cohn pool, the method comprising the steps of: precipitating immunoglobulins, A1PI, Factor H, and IaIp in a first precipitation step by adding ethanol to a Cohn pool to a final concentration of between 20% and 30% at a pH from 5.0 to 6.0 to form a first precipitate and a first supernatant; separating the first precipitate from the first supernatant; wherein the first precipitate contains i.) at least 95%, preferably at least 97%, more preferably at least 99% of the IgG content of the starting Cohn pool, ii.) at least 90%, preferably at least 95%, most preferably at least 97% of the A1PI content of the starting Cohn pool, iii.) at least 80%, preferably at least 90%, more preferably at least 95% of the Factor H content of the starting Cohn pool, and iv.) at least 80%, preferably at least 90%, more preferably at least 95% of the IaIp content of the starting Cohn pool, and further wherein the first supernatant contains at least 70%, preferably at least 80%, more preferably at least 90% of the albumin content of the Cohn pool. In one embodiment, the first precipitation step is performed by admixing ethanol with a starting plasma pool (the Cohn pool) to a final concentration of from 22% to 28% (v/v) at a pH between 5.0 and 6.0. In one embodiment, ethanol is admixed with the Cohn pool to a final concentration of 25±3% (v/v). In another embodiment, ethanol is admixed with the Cohn pool to a final concentration of 25±2% (v/v). In another embodiment, ethanol is admixed with the Cohn pool to a final concentration of 25±1% (v/v). In another embodiment, ethanol is admixed with the Cohn pool to a final concentration of 25% (v/v). Likewise, in one embodiment, the first precipitation step is performed at a pH of 5.5±0.5. In another embodiment, the first precipitation step is performed at a pH of 5.5±0.4. In another embodiment, the first precipitation step is performed at a pH of 5.5±0.3. In another embodiment, the first precipitation step is performed at a pH of 5.5±0.2. In another embodiment, the first precipitation step is performed at a pH of 5.5±0.1. In another embodiment, the first precipitation step is performed at a pH of 5.5. In yet other embodiments, the final ethanol concentration and pH of the first precipitation step is selected from variations 1 to 2166, as listed in Table 1, Table 2, Table 3, Table 4, Table 5, Table 6, and Table 7.

IV. Preparation of Immunoglobulin Compositions

Generally, immunoglobulin preparations according to the present invention can be prepared from any suitable starting plasma material, for example, recovered plasma or source plasma. In a typical example, blood or plasma is collected from healthy donors. Usually, the blood is collected from the same species of animal as the subject to which the immunoglobulin preparation will be administered (typically referred to as "homologous" immunoglobulins). The recovered or source plasma may or may not be cryo-precipitated to provide a cryo-poor plasma. Furthermore, the plasma or cryo-poor plasma may also be treated to remove one or more blood factor by adsorption, ion exchange chromatography, or other chromatographic method. Immunoglobulins are then precipitated from the plasma or cryo-poor plasma starting material, referred to as a "Cohn pool," under low pH, high alcohol conditions to form a Fraction I-IV-1 precipitate.

The immunoglobulins may be further enriched from the Fraction I-IV-1 precipitate by suitable procedures, for example, precipitation (alcohol fractionation or polyethylene glycol fractionation), chromatographic methods (e.g., ion exchange chromatography, affinity chromatography, immunoaffinity chromatography, etc.), filtration (Ultrafiltration/diafiltration, nanofiltration), ultracentrifugation, electrophoretic preparation, and the like. (See, e.g., Cohn et al., J. Am. Chem. Soc. 68:459-75 (1946); Oncley et al., J. Am. Chem. Soc. 71:541-50 (1949); Barundem et al., Vox Sang. 7:157-74 (1962); Koblet et al., Vox Sang. 13:93-102 (1967); U.S. Pat. Nos. 5,122,373 and 5,177,194; PCT/US2010/036470; and PCT/US2011/038247; the disclosures of which are hereby incorporated by reference in their entireties for all purposes).

A. Upstream Processing

Among other aspects, the present invention provides methods for fractionating proteins present in pooled plasma by performing an initial precipitation step that precipitates a majority of the immunoglobulin and alpha-1-antitrypsin content of the starting plasma. To further increase the purity of individual plasma proteins (e.g., IgG, A1PI, Factor H, IaIp, etc.) found in the precipitate and supernatant of the initial precipitation step, these compositions can be further enriched by fractionation (e.g., by alcohol precipitation, PEG precipitation, salting out, etc.), chromatography, filtration, or other method. Although use of these various techniques for the enrichment of a plasma-derived protein may be performed in any order, in a particular embodiment, the first precipitate and/or supernatant is first fractionated (e.g., by ethanol precipitation) and then enriched using chromatographic and/or filtration techniques. In the context of the present invention, the initial precipitation reaction and subsequent fractionation are aggregately referred to as "upstream processing" steps, while the chromatographic and filtration steps are aggregately referred to as "downstream processing" steps.

1. Mass Immunoglobulin Precipitation

As described herein, the inventors have discovered an improved method for fractionating human plasma in order to purify therapeutically beneficial blood proteins such as immunoglobulins, alpha-1-antitrypsin (A1PI), factor H, Inter-alpha-Inhibitor proteins (IaIp), albumin, fibrinogen, etc. This method incorporates an initial purification step in which the majority of the immunoglobulin, A1PI, factor H, IaIp, and fibrinogen content of the starting Cohn pool (i.e., blood, plasma, and/or pre-treated plasma) is precipitated and the majority of the albumin content of the starting Cohn pool remains in the supernatant. Advantageously, the inventors have developed a method of separating immunoglobulins from A1PI, factor H, and IaIp by extracting the immunoglobulins, but not the other proteins, from the initial precipitate. In particular, the inventors have found that treating a suspension of the initial precipitate with finely divided silicon dioxide ($SiO_2$) improves the retention of A1PI, factor H, and IaIp in the insoluble fraction. Without being bound by theory, the inventors believe that under certain conditions, A1PI, factor H, and IaIp, which may be initially extracted from the precipitate, bind to the finely divided silicon dioxide, which is subsequently removed with the insoluble portion of the suspension. Separation of the resulting supernatant (i.e., the soluble fraction of the suspension) provides an enriched solution containing the majority of the immunoglobulin content of the starting Cohn Fraction.

In one aspect, the present invention provides a method for preparing an enriched immunoglobulin composition from a Cohn pool, the method comprising the steps of: co-precipitating immunoglobulins and alpha-1-antitrypsin (A1PI) from a Cohn pool, in a first precipitation step, to form a first precipitate and a first supernatant; suspending the first precipitate to form a first suspension; removing the A1PI from the suspension; and recovering the soluble fraction of the first suspension, thereby forming an enriched immunoglobulin composition. Generally, any chemical means for the precipitation of immunoglobulins and A1PI may be used, including but not limited to, alcohol precipitation (e.g., using ethanol or methanol), precipitation using water soluble polymers (e.g., PEG or dextran), and salting out (e.g., using ammonium phosphate, ammonium sulfate, sodium citrate, etc.). In a preferred embodiment, the precipitation is alcohol precipitation, preferably ethanol precipitation. In one embodiment, the enriched immunoglobulin composition is an IgG composition.

In one embodiment, the first precipitation step is performed by admixing ethanol with the Cohn pool to a final concentration of from 20% to 30% (v/v) at a pH between 5.0 and 6.0. In one embodiment, ethanol is admixed with the Cohn pool to a final concentration of 25±3% (v/v). In another embodiment, ethanol is admixed with the Cohn pool to a final concentration of 25±2% (v/v). In another embodiment, ethanol is admixed with the Cohn pool to a final concentration of 25±1% (v/v). In another embodiment, ethanol is admixed with the Cohn pool to a final concentration of 25% (v/v). Likewise, in one embodiment, the first precipitation step is performed at a pH of 5.5±0.5. In another embodiment, the first precipitation step is performed at a pH of 5.5±0.4. In another embodiment, the first precipitation step is performed at a pH of 5.5±0.3. In another embodiment, the first precipitation step is performed at a pH of 5.5±0.2. In another embodiment, the first precipitation step is performed at a pH of 5.5±0.1. In another embodiment, the first precipitation step is performed at a pH of 5.5. In yet other embodiments, the final ethanol concentration and pH of the first precipitation step is selected from variations 1 to 2166, as listed in Table 1, Table 2, Table 3, Table 4, Table 5, Table 6, and Table 7. In one embodiment, the enriched immunoglobulin composition is an IgG composition.

The methods provided herein provide significantly higher yields of immunoglobulin recovery in the final enriched product due to the precipitation of a majority of the immunoglobulin content of the starting Cohn pool in the initial precipitation reaction, as compared to state of the art purification procedures that rely on initial low alcohol precipitation steps (i.e., Fraction I precipitation).

Accordingly, in one embodiment of the methods provided herein, at least 90% of the immunoglobulin content of the starting Cohn pool is precipitated in the initial precipitation reaction. In a preferred embodiment, at least 95% of the immunoglobulin content of the starting Cohn pool is precipitated in the initial precipitation reaction. In a more preferred embodiment, at least 99% of the immunoglobulin content of the starting Cohn pool is precipitated in the initial precipitation reaction. In certain embodiments, at least 90%, 91%, 92%, 93%, 94%, 95%, 96%, 97%, 98%, 99%, or more of the immunoglobulin content of the starting Cohn pool is precipitated in the initial precipitation reaction. In one specific embodiment, the immunoglobulin content of the starting Cohn pool refers to the IgG content of the starting Cohn pool.

As shown in the examples provided herein, the use of an initial low pH, high alcohol precipitation step (i.e., Fraction I-IV-1 precipitation) results in the precipitation of at least 99% of the IgG content of the starting Cohn pool. Accordingly, in one embodiment, the present invention provides a method for preparing an enriched immunoglobulin composition, the method comprising the steps of: precipitating from 99% to 100% of IgG content from a Cohn pool in a first precipitation step by adding ethanol to the Cohn pool to a final concentration of between 20% and 30% at a pH from 5.0 to 6.0 to form a first precipitate and a first supernatant; separating the first precipitate from the first supernatant; and recovering IgG from the first precipitate, thereby forming an enriched immunoglobulin composition. In one embodiment, IgG recovered from the first precipitate is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In one embodiment, the enriched immunoglobulin composition is an IgG composition. In one embodiment, ethanol is admixed with the Cohn pool to a final concentration of 25±3% (v/v).

As evidenced by the data presented in Table 15 and Table 31, greater than 97% of the alpha-1-antitrypsin (A1PI) content of a Cohn pool is also precipitated by an initial low pH, high alcohol precipitation step. Accordingly, in one embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; removing the A1PI from the suspension; and recovering the soluble fraction of the first suspension, thereby forming an enriched immunoglobulin composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In one embodiment, the enriched immunoglobulin composition is an IgG composition.

Furthermore, it was found that greater than 90% of the albumin content of a Cohn pool is not precipitated by an initial low pH, high alcohol precipitation step (Table 33), and can thus be recovered from the supernatant. Accordingly, in one embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; removing the A1PI from the suspension; and recovering the soluble fraction of the first suspension, wherein from 80% to 100% of the albumin content of the Cohn pool is present in the first supernatant, thereby forming an enriched immunoglobulin composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In one embodiment, the enriched immunoglobulin composition is an IgG composition.

2. Extraction and Separation of Immunoglobulins

As compared to a Cohn Fraction II+III precipitate or Kistler-Nitschmann Precipitate A, the initial precipitate formed by the methods provided herein contains substantially higher levels of non-immunoglobulin proteins, including A1PI and fibrinogen. For example, as shown in Table 30, nearly 100% of the fibrinogen content of the starting Cohn pool is co-precipitated with immunoglobulins in an initial low pH, high alcohol precipitation reaction. This is in contrast to the Cohn-Oncley and Kistler-Nitschmann purification schemes, in which the bulk of the fibrinogen is removed in an initial low alcohol precipitation step (Fraction I precipitation). Likewise, as shown in Table 15 and Table 31, greater than 97% of the alpha-1-antitrypsin (A1PI) content of the starting Cohn pool is co-precipitated with immunoglobulins in an initial low pH, high alcohol precipitation reaction. In contrast, the bulk of A1PI is not co-precipitated with immunoglobulins in the Cohn-Oncley and Kistler-Nitschmann purification schemes. Rather, A1PI is found in the Fraction II+III supernatant or Supernatant A.

Accordingly, in order to provide pharmaceutical grade immunoglobulin compositions, contaminants such as A1PI and fibrinogen present in the initial precipitate need to be removed from the immunoglobulin composition. This may be achieved, for example, by further fractionation of the first precipitate (e.g., by differential precipitation using alcohol, non-ionic hydrophilic polymers, or salting-out), chromatographic methodologies, or filtration methodologies.

In one embodiment, the first precipitate is suspended in Water for Injection (WFI) or a low ionic strength buffer suitable to extract immunoglobulins from the precipitate. In certain embodiments, the suspension is then treated with finely divided silicon dioxide ($SiO_2$), and the soluble portion of the suspension containing the immunoglobulins is separated from the insoluble portion of the suspension containing the bulk of the A1PI and fibrinogen.

Suitable solutions for the extraction of the first precipitate will generally have a pH between 4.0 and 5.5. In certain embodiments, the solution will have a pH between 4.5 and 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer is 4.7±0.1. In another preferred embodiment, the pH of the extraction buffer is 4.8±0.1. In another preferred embodiment, the pH of the extraction buffer is 4.9±0.1. Generally, these pH requirements can be met using a buffering agent selected from, for example, acetate, citrate, monobasic phosphate, dibasic phosphate, mixtures thereof, and the like. Suitable buffer concentrations typically range from 5 to 100 mM, or from 10 to 50 mM, or 5, 10, 15, 20, 25, 30, 35, 40, 45, 50, 55, 60, 65, 70, 75, 80, 85, 90, 95, or 100 mM buffering agent.

The extraction buffer will preferably have a conductivity of from 0.5 mS/cm to 2.0 mS/cm. For example, in certain embodiments, the conductivity of the extraction buffer will be 0.5±0.1 mS/cm, or 0.6±0.1, 0.7±0.1, 0.8±0.1, 0.9±0.1, 1.0±0.1, 1.1±0.1, 1.2±0.1, 1.3±0.1, 1.4±0.1, 1.5±0.1, 1.6±0.1, 1.7±0.1, 1.8±0.1, 1.9±0.1, or 2.0±0.1 mS/cm. One of ordinary skill in the art will know how to generate extraction buffers having an appropriate conductivity. In one particular embodiment, the extraction buffer contains 5 mM monobasic sodium phosphate and 5 mM acetate at a pH of 4.8±0.2 and conductivity of from 0.7 to 0.9 mS/cm.

In one embodiment, finely divided silicon dioxide is admixed with the Fraction I-IV-1 suspension prior to filtration. In one embodiment, this pretreatment step comprises addition of finely divided silica dioxide particles (e.g., fumed silica; Aerosil®) followed by a 40 to 80 minute incubation period during which the suspension is constantly mixed. In certain embodiments, the incubation period will be between about 50 minutes and about 70 minutes, or about 30, 35, 40, 45, 50, 55, 60, 65, 70, 75, 80, 85, 90, or more minutes. Generally, the treatment will be performed at between 0° C. and 10° C., or between 2° C. and 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between 2° C. and 10° C. In a preferred embodiment, the treatment is performed at between 5° C. and 10° C.

In one embodiment, fumed silica is added at a concentration of between 20 g/kg Fraction I-IV-1 precipitate and 100 g/kg Fraction I-IV-1 precipitate. In another embodiment, fumed silica is added at a concentration of between 30 g/kg Fraction I-IV-1 precipitate and 80 g/kg Fraction I-IV-1 precipitate. In certain embodiments, the fumed silica may be added at a concentration of about 20 g/kg Fraction I-IV-1 precipitate, or about 25, 30, 35, 40, 45, 50, 55, 60, 65, 70, 75, 80, 85, 90, 95, or 100 g/kg Fraction I-IV-1 precipitate. In one specific embodiment, fumed silica (e.g., Aerosil 380 or equivalent) is added to the Fraction I-IV-1 suspension to a final concentration of 40±20 g/kg Fraction I-IV-1 precipitate. In another specific embodiment, fumed silica is added to the Fraction I-IV-1 suspension to a final concentration of 40±10 g/kg Fraction I-IV-1 precipitate. Mixing takes place at 2° C. to 8° C. for at least 50 to 70 minutes.

In certain embodiments, $SiO_2$ is added to an immunoglobulin composition at a concentration of from 0.01 g/g total protein to 10 g/g total protein. In another embodiment, $SiO_2$ is added to an immunoglobulin composition at a concentration of from 0.01 g/g total protein to 5 g/g total protein. In another embodiment, $SiO_2$ is added to an immunoglobulin composition at a concentration of from 0.02 g/g total protein to 4 g/g total protein. In one embodiment, $SiO_2$ is added at a final concentration of at least 0.1 g per gram total protein. In another specific embodiment, fumed silica is added at a concentration of at least 0.2 g per gram total protein. In another specific embodiment, fumed silica is added at a concentration of at least 0.25 g per gram total protein. In other specific embodiments, fumed silica is added at a concentration of at least 1 g per gram total protein. In another specific embodiment, fumed silica is added at a concentration of at least 2 g per gram total protein. In another specific embodiment, fumed silica is added at a concentration of at least 2.5 g per gram total protein. In yet other specific embodiments, finely divided silicon dioxide is added at a concentration of at least 0.01 g/g total protein or at least 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.5 g, 2.0 g, 2.5 g, 3.0 g, 3.5 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, or more per gram total protein.

Accordingly, in one embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp, thereby forming an enriched immunoglobulin composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In a specific embodiment, the soluble and insoluble portions of the first suspension are separated by filtration. In one embodiment, the enriched immunoglobulin composition is an IgG composition.

Furthermore, it was found that greater than 90% of the albumin content of a Cohn pool is not precipitated by an initial low pH, high alcohol precipitation step (Table 33), and can thus be recovered from the supernatant. Accordingly, in one embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp, and further wherein from 80% to 100% of the albumin content of the Cohn pool is present in the first supernatant, thereby forming an enriched immunoglobulin composition. In one embodiment, ethanol is admixed with the Cohn pool to a final concentration of 25±3% (v/v). In one embodiment, IgG present in the soluble portion of the suspension is further enriched. In another embodiment, A1PI present in the insoluble portion of the suspension is further enriched. In another embodiment, fibrinogen present in the insoluble portion of the suspension is further enriched. In another embodiment, Factor H present in the insoluble portion of the suspension is further enriched. In another embodiment, IaIp present in the insoluble portion of the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a specific embodiment, the soluble and insoluble portions of the first suspension are separated by filtration. In one embodiment, the enriched immunoglobulin composition is an IgG composition.

3. Fractionation

In one embodiment, immunoglobulins recovered from the soluble portion of the first suspension (I-IV-1 paste suspension) are further enriched by fractionation. Generally, any method of fractionation (e.g., alcohol or polymer precipitation, salting out, etc.) may be used. In a preferred embodiment, immunoglobulins are further enriched by fractionating the soluble portion of the first suspension by ethanol precipitation. In one embodiment, immunoglobulins are enriched by the addition of ethanol to the soluble portion of the first suspension at a final concentration and pH suitable to precipitate the immunoglobulins, while at least one contaminant is not precipitated. In another embodiment, immunoglobulins are enriched by the addition ethanol to the soluble portion of the first suspension at a final concentration and pH suitable to precipitate at least one contaminant, while the immunoglobulins are not precipitated.

Additional fractionation of the material recovered from the initial low pH, high alcohol precipitation step is optional. In certain embodiments, the immunoglobulin composition recovered from the initial low pH, high alcohol precipitation step may be further enriched using one or more of the various downstream processing steps described herein. In other embodiments, the composition recovered from the initial low pH, high alcohol precipitation step may be further processed through the use of one or more additional precipitation steps. In certain embodiments, an additional immunoglobulin precipitation step may be used to concentrate an immunoglobulin composition, prepare an immunoglobulin for storage, and/or prepare an immunoglobulin composition for transport.

In one embodiment, the present invention provides a method for preparing an enriched immunoglobulin composition from a Cohn pool, the method comprising the steps of: co-precipitating immunoglobulins and alpha-1-antitrypsin (A1PI) from a Cohn pool, in a first precipitation step, to form a first precipitate and a first supernatant; suspending the first precipitate to form a first suspension; removing A1PI from the suspension; precipitating immunoglobulins from the first suspension in a second precipitation step, to form a second precipitate comprising immunoglobulins and a second supernatant comprising at least one contaminant; and recovering immunoglobulins from the second precipitate, thereby forming an enriched immunoglobulin composition. In one embodiment, IgG recovered from the second precipitate is further enriched. In another embodiment, A1PI removed from the first suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In one embodiment, the enriched immunoglobulin composition is an IgG composition.

In an exemplary embodiment, the second precipitation step is performed by admixing ethanol to the soluble portion of the second suspension (e.g., a filtrate or supernatant of the suspension formed after filtration or centrifugation) at a final concentration of from 22% to 28% (v/v) at a pH between 6.5 and 7.5. In one embodiment, ethanol is admixed to a final concentration of 25±3% (v/v). In another embodiment, ethanol is admixed to a final concentration of 25±2% (v/v). In another embodiment, ethanol is admixed to a final concentration of 25±1% (v/v). In another embodiment, ethanol is admixed to a final concentration of 25% (v/v). Likewise, in one embodiment, the second precipitation step is performed at a pH of 7.0±0.5. In another embodiment, the second precipitation step is performed at a pH of 7.0±0.4. In another embodiment, the second precipitation step is performed at a pH of 7.0±0.3. In another embodiment, the second precipitation step is performed at a pH of 7.0±0.2. In another embodiment, the second precipitation step is per-
formed at a pH of 7.0±0.1. In another embodiment, the second precipitation step is performed at a pH of 7.0. In a particular embodiment, the second precipitation step is performed using a final ethanol concentration of 25±3% (v/v) at a pH of 7.0±0.3.

In a preferred embodiment, the first suspension or soluble fraction thereof, is treated with a detergent prior to performing the second precipitation step. In one embodiment, the first suspension or soluble fraction thereof is further treated with citrate prior to performing the second precipitation step. In a particular embodiment, polysorbate-80 is added to the first suspension or soluble fraction thereof and the composition is incubated for at least 30 minutes.

In another particular embodiment, Sodium citrate dihydrade is further added to the first suspension or soluble fraction thereof and the composition is incubated for at least an additional minutes. In one embodiment, polysorbate-80 is added at a final concentration of about 0.2% (w/v). In one embodiment, sodium citrate dihydrate is then mixed into the solution at a final concentration of about 8 g/L. In a particular embodiment, the incubations are performed at a temperature between about 2 to 8° C. with continuous of stirring.

In a particular embodiment, the method comprises the steps of: precipitating from 99% to 100% of IgG content from a Cohn pool plasma in a first precipitation step by adding ethanol to the Cohn pool to a final concentration of between 20% and 30% at a pH from 5.0 to 6.0 to form a first precipitate and a first supernatant; separating the first precipitate from the first supernatant; suspending the first precipitate to form a first suspension; precipitating immunoglobulins from the first suspension in a second precipitation step, to form a second precipitate comprising immunoglobulins and a second supernatant comprising at least one contaminant; and recovering immunoglobulins from the second precipitate, thereby forming an enriched immunoglobulin composition. In one embodiment, ethanol is admixed with the Cohn pool to a final concentration of 25±3% (v/v). In one embodiment, IgG recovered from the second precipitate is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In one embodiment, the enriched immunoglobulin composition is an IgG composition.

In a specific embodiment, the method comprises the steps of: precipitating from 99% to 100% of IgG content from a Cohn pool plasma in a first precipitation step by adding ethanol to the Cohn pool to a final concentration of between 20% and 30% at a pH from 5.0 to 6.0 to form a first precipitate and a first supernatant; separating the first precipitate from the first supernatant; suspending the first precipitate to form a first suspension; precipitating immunoglobulins from the first suspension in a second precipitation step by admixing ethanol to the first suspension at a final concentration of from 25±3% (v/v) at a pH of 7.0±0.3, to form a second precipitate comprising immunoglobulins and a second supernatant comprising at least one contaminant; and recovering immunoglobulins from the second precipitate, thereby forming an enriched immunoglobulin composition. In one embodiment, ethanol is admixed with the Cohn pool to a final concentration of 25±3% (v/v). In one embodiment, IgG recovered from the second precipitate is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In one embodiment, the enriched immunoglobulin composition is an IgG composition.

In one embodiment, the method comprises the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; removing A1PI from the suspension; recovering the soluble fraction of the first suspension; precipitating immunoglobulins from the first suspension in a second precipitation step, to form a second precipitate comprising immunoglobulins and a second supernatant comprising at least one contaminant; and recovering immunoglobulins from the second precipitate, thereby forming an enriched immunoglobulin composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step. In one embodiment, the enriched immunoglobulin composition is an IgG composition.

In a specific embodiment, the method comprises the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; removing A1PI from the suspension; recovering the soluble fraction of the first suspension; precipitating immunoglobulins from the first suspension in a second precipitation step by admixing ethanol to the first suspension at a final concentration of from 25±3% (v/v) at a pH of 7.0±0.3, to form a second precipitate comprising immunoglobulins and a second supernatant comprising at least one contaminant; and recovering immunoglobulins from the second precipitate, thereby forming an enriched immunoglobulin composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step. In one embodiment, the enriched immunoglobulin composition is an IgG composition.

In another embodiment, the method comprises the steps of: precipitating from 99% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; removing the A1PI from the suspension; recovering the soluble portion of the first suspension; precipitating immunoglobulins from the soluble portion of the first suspension in a second precipitation step, to form a second precipitate comprising immunoglobulins and a second supernatant comprising at least one contaminant; and recovering immunoglobulins from the second precipitate, wherein from 80% to 100% of the albumin content of the Cohn pool is present in the first supernatant, thereby forming an enriched immunoglobulin composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In another embodiment, albumin present in the first supernatant is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step. In a preferred embodiment, between 90% and 100% of the albumin content of the Cohn pool is present in the first supernatant. In one embodiment, the enriched immunoglobulin composition is an IgG composition.

In another embodiment, the method comprises the steps of: precipitating from 99% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; removing the A1PI from the suspension; recovering the soluble portion of the first suspension; precipitating immunoglobulins from the soluble portion of the first suspension in a second precipitation step by admixing ethanol to the soluble portion of the first suspension at a final concentration of from 25±3% (v/v) at a pH of 7.0±0.3, to form a second precipitate comprising immunoglobulins and a second supernatant comprising at least one contaminant; and recovering immunoglobulins from the second precipitate, wherein from 80% to 100% of the albumin content of the Cohn pool is present in the first supernatant, thereby forming an enriched immunoglobulin composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In another embodiment, albumin present in the first supernatant is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step. In a preferred embodiment, between 90% and 100% of the albumin content of the Cohn pool is present in the first supernatant. In one embodiment, the enriched immunoglobulin composition is an IgG composition.

In one embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp, recovering the soluble portion of the first suspension; precipitating immunoglobulins from the soluble portion of the first suspension in a second precipitation step, to form a second precipitate comprising immunoglobulins and a second supernatant comprising at least one contaminant; and recovering immunoglobulins from the second precipitate, thereby forming an enriched immunoglobulin composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In a specific embodiment, the soluble and insoluble portions of the first suspension are separated by filtration. In one embodiment, the enriched immunoglobulin composition is an IgG composition.

In a specific embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp, recovering the soluble portion of the first suspension; precipitating immunoglobulins from the soluble portion of the first suspension in a second precipitation step by admixing ethanol to the soluble portion of the first suspension at a final concentration of from 25±3% (v/v) at a pH of 7.0±0.3, to form a second precipitate comprising immunoglobulins and a second supernatant comprising at least one contaminant; and recovering immunoglobulins from the second precipitate, thereby forming an enriched immunoglobulin composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In a specific embodiment, the soluble and insoluble portions of the first suspension are separated by filtration. In one embodiment, the enriched immunoglobulin composition is an IgG composition.

In one embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp; precipitating immunoglobulins from the soluble portion of the first suspension in a second precipitation step, to form a second precipitate comprising immunoglobulins and a second supernatant comprising at least one contaminant; and recovering immunoglobulins from the second precipitate, wherein from 80% to 100% of the albumin content of the Cohn pool is present in the first supernatant, thereby forming an enriched immunoglobulin composition. In one embodiment, ethanol is admixed with the Cohn pool to a final concentration of 25±3% (v/v). In one embodiment, IgG present in the soluble portion of the suspension is further enriched. In another embodiment, A1PI present in the insoluble portion of the suspension is further enriched. In another embodiment, fibrinogen present in the insoluble portion of the suspension is further enriched. In another embodiment, Factor H present in the insoluble portion of the suspension is further enriched. In another embodiment, IaIp present in the insoluble portion of the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the first precipitation step is selected from variations 1 to 2166, as listed in Table 1, Table 2, Table 3, Table 4, Table 5, Table 6, and Table 7. In a specific embodiment, the soluble and insoluble portions of the first suspension are separated by filtration. In one embodiment, the enriched immunoglobulin composition is an IgG composition.

In one embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp; precipitating immunoglobulins from the soluble portion of the first suspension in a second precipitation step by admixing ethanol to the soluble portion of the first suspension at a final concentration of from 25±3% (v/v) at a pH of 7.0±0.3, to form a second precipitate comprising immunoglobulins and a second supernatant comprising at least one contaminant; and recovering immunoglobulins from the second precipitate, wherein from 80% to 100% of the albumin content of the Cohn pool is present in the first supernatant, thereby forming an enriched immunoglobulin composition. In one embodiment, ethanol is admixed with the Cohn pool to a final concentration of 25±3% (v/v). In one embodiment, IgG present in the soluble portion of the suspension is further enriched. In another embodiment, A1PI present in the insoluble portion of the suspension is further enriched. In another embodiment, fibrinogen present in the insoluble portion of the suspension is further enriched. In another embodiment, Factor H present in the insoluble portion of the suspension is further enriched. In another embodiment, IaIp present in the insoluble portion of the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the first precipitation step is selected from variations 1 to 2166, as listed in Table 1, Table 2, Table 3, Table 4, Table 5, Table 6, and Table 7. In a specific embodiment, the soluble and insoluble portions of the first suspension are separated by filtration. In one embodiment, the enriched immunoglobulin composition is an IgG composition.

In one embodiment, immunoglobulins are recovered from the second precipitate by suspending the precipitate with a cold extraction buffer. For example, the second precipitate is suspended at a ratio of 1 part precipitate to 2-15 parts of Water for Injection (WFI) or low conductivity buffer. In a preferred embodiment, the second precipitate suspended at a ratio of 1 part precipitate to 4-5 parts, preferably 3.5 parts, WFI. In one embodiment, the suspension step is performed at a temperature between 0° C. and 8° C. In one embodiment, the final pH of the solution is adjusted to from 4.5 to 5.6, preferably to 5.2±0.2. In one embodiment, this pH adjustment is performed with acetic acid. In one embodiment, the conductivity of the suspension is increased to between 2.5 and 6.0 mS/cm to increase the solubility of immunoglobulins. In one embodiment, the conductivity is increased by the addition of sodium chloride.

Suitable solutions for the extraction of the second precipitate include WFI and low conductivity buffers. In one embodiment, a low conductivity buffer has a conductivity of less than about 10 mS/cm. In other embodiments, the low conductivity buffer has a conductivity of less than about 9, 8, 7, 6, 5, 4, 3, 2, or 1 mS/cm. In a preferred embodiment, the low conductivity buffer has a conductivity of less than about 6 mS/cm. In another preferred embodiment, the low conductivity buffer has a conductivity of less than about 4 mS/cm. In another preferred embodiment, the low conductivity buffer has a conductivity of less than about 2 mS/cm.

In one embodiment, the soluble portion of the suspension, containing immunoglobulins, is separated from the insoluble portion. In one embodiment, this is done by filtering the suspension with a depth filter having a nominal pore size of from 0.1 µm and 0.4 µm. In one embodiment, the nominal pore size of the depth filter is 0.2 µm (e.g., Cuno VR06 filter or equivalent). In one embodiment, the filter is washed with WFI or a suitable buffer after filtration to recover additional immunoglobulin and the post-wash added to the filtrate. In a preferred embodiment, the post-wash of the filter is performed using a sodium chloride solution with a conductivity of between about 2.5 and about 6.0 mS/cm. In another embodiment, the second suspension is centrifuged to recover the soluble portion.

B. Downstream Processing

Immunoglobulin fractions obtained after fractionation using an initial precipitation step that precipitates immunoglobulins and alpha-1-antitrypsin (A1PI), but not albumin, can be further enriched according to well known methods in the art, including without limitation: chromatography (e.g., anion exchange chromatography, cation exchange chromatography, hydrophobic interaction chromatography (HIC), hydroxyapatite chromatography (HAP), Protein A affinity chromatography, immuno-affinity chromatography, size exclusion chromatography, etc.); filtration (e.g., ultrafiltration and/or diafiltration); and one or more viral reduction steps (e.g., nanofiltration, solvent and detergent treatment, UV irradiation, heat treatment, low pH incubation, etc.).

In one embodiment, the present invention provides a method for preparing an enriched immunoglobulin composition from a Cohn pool comprising an initial low pH, high alcohol precipitation step and at least one downstream processing step (e.g., chromatography). In certain embodiments, the method further comprises a second precipitation step prior to the at least one downstream processing step (e.g., a PptG precipitation step). The second precipitation is optional, as a suspension of the initial low pH, high alcohol precipitate may be used directly for downstream purification.

In one embodiment, immunoglobulins present in a plasma-derived composition prepared using an initial low pH, high alcohol precipitation step are further enriched by performing at least one chromatographic step. In one embodiment, the chromatographic step is selected from anion exchange chromatography, cation exchange chromatography, hydrophobic interaction chromatography (HIC), hydroxyapatite chromatography (HAP), Protein A affinity chromatography, immuno-affinity chromatography, and size exclusion chromatography. In a particular embodiment, immunoglobulins are enriched by performing anion exchange chromatography. In another embodiment, immunoglobulins are further enriched by performing cation exchange chromatography. In a specific embodiment, immunoglobulins are further enriched by performing both cation and anion exchange chromatography.

In a particular embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp; binding the immunoglobulins to a cation exchange resin; eluting the immunoglobulins from the cation exchange to form a cation exchange eluate; contacting the cation exchange eluate with an anion exchange resin; and recovering immunoglobulins that do not bind to the resin, thereby forming an enriched immunoglobulin composition. In one embodiment, ethanol is admixed with the Cohn pool to a final concentration of 25±3% (v/v). In one embodiment, IgG recovered from the anion exchange chromatographic step is further enriched. In another embodiment, A1PI removed from the suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In another embodiment, between 80% and 100%, preferably between 90% and 100%, of the albumin content of the Cohn pool is present in the first supernatant. In a specific embodiment, the soluble and insoluble portions of the first suspension are separated by filtration. In one embodiment, the method further comprises at least one viral reduction/inactivation step. In a preferred embodiment, the method further comprises at least two viral reduction/inactivation steps. In a more preferred embodiment, the method further comprises at least three viral reduction/inactivation steps. In one embodiment, the enriched immunoglobulin composition is an IgG composition.

In a particular embodiment, the present invention provides a method for preparing an enriched immunoglobulin composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp, recovering the soluble portion of the first suspension; precipitating immunoglobulins from the soluble portion of the first suspension in a second precipitation step by admixing ethanol to the soluble portion of the first suspension at a final concentration of from 25±3% (v/v) at a pH of 7.0±0.3, to form a second precipitate comprising immunoglobulins and a second supernatant comprising at least one contaminant; recovering immunoglobulins from the second precipitate; binding the immunoglobulins to a cation exchange resin; eluting the immunoglobulins from the cation exchange to form a cation exchange eluate; contacting the cation exchange eluate with an anion exchange resin; and recovering immunoglobulins that do not bind to the resin, thereby forming an enriched immunoglobulin composition. In one embodiment, ethanol is admixed with the Cohn pool to a final concentration of 25±3% (v/v). In one embodiment, IgG recovered from the anion exchange chromatographic step is further enriched. In another embodiment, A1PI removed from the suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In another embodiment, between 80% and 100%, preferably between 90% and 100%, of the albumin content of the Cohn pool is present in the first supernatant. In a specific embodiment, the soluble and insoluble portions of the first suspension are separated by filtration. In one embodiment, the method further comprises at least one viral reduction/inactivation step. In a preferred embodiment, the method further comprises at least two viral reduction/inactivation steps. In a more preferred embodiment, the method further comprises at least three viral reduction/inactivation steps. In one embodiment, the enriched immunoglobulin composition is an IgG composition.

In one particular embodiment, the present invention provides a method for preparing an enriched immunoglobulin composition, the method comprising the steps of: precipitating immunoglobulins and A1PI from a Cohn pool in a low pH, high alcohol precipitation step; separating the precipitated immunoglobulins and A1PI; enriching the immunoglobulin composition by performing cation exchange chromatography; and further enriching the immunoglobulin composition by performing anion exchange chromatography. In one embodiment, the final ethanol concentration and pH used in the low pH, high alcohol precipitation step is selected from variations 1 to 2166, as listed in Table 1, Table 2, Table 3, Table 4, Table 5, Table 6, and Table 7. In one embodiment, the method further comprises at least one viral reduction/inactivation step. In a preferred embodiment, the method further comprises at least two viral reduction/inactivation steps. In a more preferred embodiment, the method further comprises at least three viral reduction/inactivation steps. In one embodiment, the enriched immunoglobulin composition is an IgG composition.

In another particular embodiment, the present invention provides a method for preparing an enriched immunoglobulin composition, the method comprising the steps of: precipitating immunoglobulins and A1PI from a Cohn pool in a low pH, high alcohol precipitation step; separating the precipitated immunoglobulins and A1PI; precipitating the separated immunoglobulins in a second precipitation step; enriching the immunoglobulin composition by performing cation exchange chromatography; and further enriching the immunoglobulin composition by performing anion exchange chromatography. In one embodiment, the final ethanol concentration and pH used in the low pH, high alcohol precipitation step is selected from variations 1 to 2166, as listed in Table 1, Table 2, Table 3, Table 4, Table 5, Table 6, and Table 7. In one embodiment, the method further comprises at least one viral reduction/inactivation step. In a preferred embodiment, the method further comprises at least two viral reduction/inactivation steps. In a more preferred embodiment, the method further comprises at least three viral reduction/inactivation steps. In one embodiment, the enriched immunoglobulin composition is an IgG composition.

In another particular embodiment, the present invention provides a method for preparing an enriched immunoglobulin composition, the method comprising the steps of: precipitating immunoglobulins and A1PI from a Cohn pool in a low pH, high alcohol precipitation step; separating the precipitated immunoglobulins and A1PI; precipitating the separated immunoglobulins in a second precipitation step; treating the immunoglobulin composition with a solvent and detergent to inactivate viruses; enriching the immunoglobulin composition by performing cation exchange chromatography; further enriching the immunoglobulin composition by performing anion exchange chromatography; and nanofiltering the immunoglobulin composition to remove viruses. In one embodiment, the final ethanol concentration and pH used in the low pH, high alcohol precipitation step is selected from variations 1 to 2166, as listed in Table 1, Table 2, Table 3, Table 4, Table 5, Table 6, and Table 7. In one embodiment, the method further comprises concentrating the immunoglobulin composition by ultrafiltration/diafiltration to a final protein concentration of from 5 g/L to 25 g/L. In a particular embodiment, the final concentration of the enriched immunoglobulin composition is 5±1% (w/v). In another particular embodiment, the final concentration of the enriched immunoglobulin composition is 10±1% (w/v). In another particular embodiment, the final concentration of the enriched immunoglobulin composition is 15±1% (w/v). In another particular embodiment, the final concentration of the enriched immunoglobulin composition is 20±2% (w/v). In another particular embodiment, the final concentration of the enriched immunoglobulin composition is 25±2% (w/v). In one embodiment, the enriched immunoglobulin composition is an IgG composition.

C. Exemplary Enrichment of IgG from Fraction I-IV-1 Precipitate

1. Extraction of Fraction I-IV-1 Precipitate

In order to solubilize the IgG content of the Fraction I-IV-1 precipitate, a cold extraction buffer is used to re-suspend the Fractionation II+III precipitate at a typical ratio of 1 part precipitate to 15 parts of extraction buffer. Other suitable re-suspension ratios may be used, for example from 1:8 to 1:30, or from 1:10 to 1:20, or from 1:12 to 1:18, or from 1:13 to 1:17, or from 1:14 to 1:16. In certain embodiments, the re-suspension ratio may be 1:8, 1:9, 1:10, 1:11, 1:12, 1:13, 1:14, 1:15, 1:16, 1:17, 1:18, 1:19, 1:20, 1:21, 1:22, 1:23, 1:24, 1:25, 1:26, 1:27, 1:28, 1:29, 1:30, or higher.

Suitable solutions for the extraction of the first precipitate will generally have a pH between 4.0 and 5.5. In certain embodiments, the solution will have a pH between 4.5 and 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer is 4.7±0.1. In another preferred embodiment, the pH of the extraction buffer is 4.8±0.1. In another preferred embodiment, the pH of the extraction buffer is 4.9±0.1. Generally, these pH requirements can be met using a buffering agent selected from, for example, acetate, citrate, monobasic phosphate, dibasic phosphate, mixtures thereof, and the like. Suitable buffer concentrations typically range from 5 to 100 mM, or from 10 to 50 mM, or 5, 10, 15, 20, 25, 30, 35, 40, 45, 50, 55, 60, 65, 70, 75, 80, 85, 90, 95, or 100 mM buffering agent.

The extraction buffer will preferably have a conductivity of from 0.5 mS/cm to 2.0 mS/cm. For example, in certain embodiments, the conductivity of the extraction buffer will be 0.5±0.1 mS/cm, or about 0.6±0.1, 0.7±0.1, 0.8±0.1, 0.9±0.1, 1.0±0.1, 1.1±0.1, 1.2±0.1, 1.3±0.1, 1.4±0.1, 1.5±0.1, 1.6±0.1, 1.7±0.1, 1.8±0.1, 1.9±0.1, or 2.0±0.1 mS/cm. One of ordinary skill in the art will know how to generate extraction buffers having an appropriate conductivity.

In an exemplary embodiment, the Fraction I-IV-1 precipitate is extracted with a paste to buffer ratio of 1:15 using an extraction buffer containing 5 mM monobasic sodium phosphate and 5 mM acetate, the pH of which is adjusted to 4.8±0.2 with acetic acid. In one embodiment, the pH of the solution is maintained at a pH of 4.8±0.3 for the duration of the extraction process. In a specific embodiment, the pH of the solution is maintained at a pH of 4.8±0.2 for the duration of the extraction process.

Generally, the extraction is performed at a temperature between 0° C. and 10° C., or between 2° C. and 8° C. In certain embodiments, the extraction may be performed at 0±1° C., 1±1° C., 2±1° C., 3±1° C., 4±1° C., 5±1° C., 6±1° C., 7±1° C., 8±1° C., 9±1° C., or 10±1° C. In a particular embodiment, the extraction is performed at between 2° C. and 10° C. Typically, the extraction process will proceed for between 60 and 300 minutes, or for between 120 and 240 minutes, or for between 150 and 210 minutes, while the suspension is continuously stirred. In certain embodiments, the extraction process will proceed for about 60, 70, 80, 90, 100, 110, 120, 130, 140, 150, 160, 170, 180, 190, 200, 210, 220, 230, 240, 250, 260, 270, 280, 290, 300 minutes, or more. In a preferred embodiment, the extraction process will proceed for at least 160 minutes with continuous stirring.

2. Silicon Dioxide ($SiO_2$) Treatment

As compared to Cohn-Oncley and Kistler-Nitschmann purifications, the initial immunoglobulin-containing precipitates formed by the methods provided herein contain substantially higher levels of non-immunoglobulin proteins, including A1PI, fibrinogen, Factor H, and IaIp. It is known that Factor H and IaIp can be bound by and subsequently eluted off of finely divided silicon dioxide (see, WO 2011/011753 and PCT/US2011/045099, the disclosures of which are both expressly incorporated by reference in their entireties for all purposes). Advantageously, it was found that inclusion of a $SiO_2$ treatment step after extraction of the Fraction I-IV-1 precipitate and prior to filtration of the Fraction I-IV-1 suspension aids in the separation of A1PI, fibrinogen, Factor H, and IaIp into the insoluble filter cake formed during filtration of the Fraction I-IV-1 suspension.

Accordingly, in one embodiment, finely divided silicon dioxide is admixed with the Fraction I-IV-1 suspension prior to filtration. In one embodiment, this pretreatment step comprises addition of finely divided silica dioxide particles (e.g., fumed silica; Aerosil®) followed by a 40 to 80 minute incubation period during which the suspension is constantly mixed. In certain embodiments, the incubation period will be between about 50 minutes and about 70 minutes, or about 30, 35, 40, 45, 50, 55, 60, 65, 70, 75, 80, 85, 90, or more minutes. Generally, the treatment will be performed at between 0° C. and 10° C., or between 2° C. and 8° C. In certain embodiments, the treatment may be performed at about 0° C., 1° C., 2° C., 3° C., 4° C., 5° C., 6° C., 7° C., 8° C., 9° C., or 10° C. In a particular embodiment, the treatment is performed at between 2° C. and 10° C. In a preferred embodiment, the treatment is performed at between 5° C. and 10° C.

In certain embodiments, fumed silica is added at a concentration of between 20 g/kg Fraction I-IV-1 precipitate and 100 g/kg Fraction I-IV-1 precipitate. In certain embodiments, the fumed silica may be added at a concentration of about 20 g/kg Fraction I-IV-1 precipitate, or about 25, 30, 35, 40, 45, 50, 55, 60, 65, 70, 75, 80, 85, 90, 95, or 100 g/kg Fraction I-IV-1 precipitate. In one specific embodiment, fumed silica (e.g., Aerosil 380 or equivalent) is added to the Fraction I-IV-1 suspension to a final concentration of 40±10 g/kg Fraction I-IV-1 precipitate. Mixing takes place at 2° C. to 8° C. for at least 50 to 70 minutes.

In certain embodiments, $SiO_2$ is added to an IgG composition at a concentration of from 0.01 g/g total protein to 10 g/g total protein. In another embodiment, $SiO_2$ is added to an IgG composition at a concentration of from 0.01 g/g total protein to 5 g/g total protein. In another embodiment, $SiO_2$ is added to an IgG composition at a concentration of from 0.02 g/g total protein to 4 g/g total protein. In one embodiment, $SiO_2$ is added at a final concentration of at least 0.1 g per gram total protein. In another specific embodiment, fumed silica is added at a concentration of at least 0.2 g per gram total protein. In another specific embodiment, fumed silica is added at a concentration of at least 0.25 g per gram total protein. In other specific embodiments, fumed silica is added at a concentration of at least 1 g per gram total protein. In another specific embodiment, fumed silica is added at a concentration of at least 2 g per gram total protein. In another specific embodiment, fumed silica is added at a concentration of at least 2.5 g per gram total protein. In yet other specific embodiments, finely divided silicon dioxide is added at a concentration of at least 0.01 g/g total protein or at least 0.02 g, 0.03 g, 0.04 g, 0.05 g, 0.06 g, 0.07 g, 0.08 g, 0.09 g, 0.1 g, 0.2 g, 0.3 g, 0.4 g, 0.5 g, 0.6 g, 0.7 g, 0.8 g, 0.9 g, 1.0 g, 1.5 g, 2.0 g, 2.5 g, 3.0 g, 3.5 g, 4.0 g, 4.5 g, 5.0 g, 5.5 g, 6.0 g, 6.5 g, 7.0 g, 7.5 g, 8.0 g, 8.5 g, 9.0 g, 9.5 g, 10.0 g, or more per gram total protein.

3. Filtration of the Fraction I-IV-1 Suspension

In order to separate the soluble portion of the Fraction I-IV-1 suspension containing immunoglobulins from the insoluble portion containing fibrinogen, A1PI, Factor H, and IaIp, the suspension is filtered, typically using depth filtration. Depth filters that may be employed in the methods provided herein include, metallic, glass, ceramic, organic (such as diatomaceous earth) depth filters, and the like. Examples of suitable filters include, without limitation, Cuno 50SA, Cuno 90SA, and Cuno VR06 filters (3M). Alternatively, the separation step can be performed by centrifugation rather than filtration.

In certain embodiments, filter aid, for example Celpure C300 (Advanced Minerals) or Hyflo-Super-Cel (World Minerals), is added to the suspension after the silica dioxide treatment to facilitate depth filtration. Filter aid is added at a final concentration of from 0.1 kg/kg Fraction I-IV-1 precipitate to 1.0 kg/kg Fraction I-IV-1 precipitate, or from 0.2 kg/kg Fraction I-IV-1 precipitate to 0.8 kg/kg Fraction I-IV-1 precipitate, or from 0.3 kg/kg Fraction I-IV-1 precipitate to 0.7 kg/kg Fraction I-IV-1 precipitate. In other embodiments, filter aid can be added at a final concentration of from 0.1 kg/kg Fraction I-IV-1 precipitate to 0.7 kg/kg Fraction I-IV-1 precipitate, or from 0.2 kg/kg Fraction I-IV-1 precipitate to 0.6 kg/kg Fraction I-IV-1 precipitate, or from about 0.3 kg/kg Fraction I-IV-1 precipitate to about 0.05 kg/kg Fraction I-IV-1 precipitate. In certain embodiments, the filter aid will be added at a final concentration of about 0.01 kg/kg Fraction I-IV-1 precipitate, or about 0.02, 0.03, 0.04, 0.05, 0.06, 0.07, 0.08, 0.09, 0.1, 0.2, 0.3, 0.4, 0.5, 0.6, 0.7, 0.8, 0.9, or 1.0 kg/kg Fraction I-IV-1 precipitate.

In order to minimize the loss of immunoglobulins during filtration, the filter cake formed should be washed with at least one dead volume, preferably at least two dead volumes, more preferably at least three dead volumes, of suspension buffer or a similar buffer thereto, which is not sufficient to solubilize non-immunoglobulin proteins present in the filter cake. In one embodiment, the filter and filter cake are post washed with at least 3.0 dead volumes of buffer. In another embodiment, the filter and filter cake are post washed with at least 3.6 dead volumes of buffer. In another embodiment, the filter and filter cake are post washed with at least 50% of the suspension volume filtered, using a suitable buffer. In another embodiment, the filter and filter cake are post washed with at least 75% of the suspension volume filtered, using a suitable buffer. In another embodiment, the filter and filter cake are post washed with at least 100% of the suspension volume filtered, using a suitable buffer. Typically, no more than 200% of the suspension volume filtered should be used to wash the filter and filter cake.

In a specific embodiment, the wash buffer is the dissolution buffer containing from 90 to 150 mL of glacial acetic acid per 1000 L. In one embodiment, the pH of the post-wash extraction buffer is between about 4.6 and about 5.3. In a preferred embodiment, the pH of the post-wash buffer is between about 4.7 and about 5.2. In another preferred embodiment, the pH of the post-wash buffer is between about 4.8 and about 5.1. In yet another preferred embodiment, the pH of the post-wash buffer is between about 4.9 and about 5.0.

4. Detergent Treatment

To remove additional contaminants from the Fraction I-IV-1 filtrate, the sample is next subjected to a detergent treatment. Methods for the detergent treatment of plasma derived fractions are well known in the art. Generally, any standard non-ionic detergent treatment may be used in conjunction with the methods provided herein. For example, an exemplary protocol for a detergent treatment is provided below.

Polysorbate-80 is added to the Fraction I-IV-1 filtrate at a final concentration of about 0.2% (w/v) with stirring and the sample is incubated for at least 30 minutes at a temperature between about 2 to 8° C. Sodium citrate dihydrate is then mixed into the solution at a final concentration of about 8 g/L and the sample is incubated for an additional 30 minutes, with continuous of stirring at a temperature between about 2 to 8° C.

In certain embodiments, any suitable non-ionic detergent can be used. Examples of suitable non-ionic detergents include, without limitation, Octylglucoside, Digitonin, C12E8, Lubrol, Triton X-100, Nonidet P-40, Tween-20 (i.e., polysorbate-20), Tween-80 (i.e., polysorbate-80), an alkyl poly(ethylene oxide), a Brij detergent, an alkylphenol poly(ethylene oxide), a poloxamer, octyl glucoside, decyl maltoside, and the like.

In one embodiment, a process improvement is realized by adding the detergent reagents (e.g., polysorbate-80 and sodium citrate dehydrate) by diffuse addition. The diffuse addition of these reagents minimizes local fluctuations of alcohol concentration and pH as compared to addition at a single entry point. In one embodiment, the diffuse addition comprises spraying, rather than fluent addition. In another embodiment, the diffuse addition comprises addition of a reagent from multiple ports. In one embodiment, the diffuse addition comprises addition of a reagent from a diffuser port. In certain embodiments, at least one port used to introduce a reagent into the system is located at or near an impeller or other dispersive element. In other embodiments, the detergent reagents may be added as solids to the Modified Fraction II+III filtrate while the sample is being mixed to ensure rapid distribution of the additives. In certain embodiments, it is preferable to add solid reagents by sprinkling the solids over a delocalized surface area of the filtrate such that local overconcentration does not occur, such as in fluent addition.

5. Second Precipitation Event—Precipitation G

In order to remove residual impurities, a second precipitation is performed at pH 6.5 to 7.5 using 25% alcohol. Briefly, the Fraction I-IV-1 extraction is adjusted to a pH from 6.5 to 7.5, preferably from 6.8 to 7.2, more preferably from 6.9 to 7.1, most preferably 7.0 with a suitable pH modifying solution (e.g., sodium hydroxide or acetic acid). Cold alcohol is then added to the solution to a final concentration of about 25% (v/v) and the mixture is incubated while stirring at between about −6° C. to about −10° C. for at least 1 hour to form a second precipitate (i.e., precipitate G). In one embodiment, the mixture is incubated for at least 2 hours, or at least 3, 4, 5, 6, 7, 8, 9, 10, 11, 12, 13, 14, 15, 16, 17, 18, 19, 20, 21, 22, 23, 24, or more hours. In a preferred embodiment, the mixture is incubated for at least 2 hours. In a more preferred embodiment, the mixture is incubated for at least 4 hours. In an even more preferred embodiment, the mixture is incubated for at least 8 hours.

In certain embodiments, a higher percentage of IgG may be precipitated from the I-IV-1 extraction by adjusting the pH of the solution during and/or after the addition of alcohol to the precipitation reaction. Likewise, due to fluctuations in the pH of the solution during the precipitation process, the pH of the reaction mixture may be monitored and/or adjusted throughout the entirety of the incubation. In another embodiment, improvement in the yield of IgG is achieved by adding the precipitating alcohol and/or the solution used to adjust the pH of the mixture by diffuse addition of the alcohol or pH modifying agent. The diffuse addition of these reagents minimizes local fluctuations of alcohol concentration and pH as compared to addition at a single entry point. In one embodiment, the diffuse addition comprises spraying, rather than fluent addition. In another embodiment, the diffuse addition comprises addition of a reagent from multiple ports. In one embodiment, the diffuse addition comprises addition of a reagent from a diffuser port. In certain embodiments, at least one port used to introduce a reagent into the system is located at or near an impeller or other dispersive element.

6. Suspension and Filtration of Precipitate G (Ppt G)

In order to solubilize the IgG content of the precipitate G, a cold extraction buffer is used to re-suspend the PptG. Briefly, the precipitate G is dissolved at a ratio of 1 part precipitate to 2-5 parts Water for Injection (WFI) or low conductivity buffer. In a preferred embodiment, the precipitate G is dissolved at a ratio of 1 part precipitate to 1-15 parts, preferably 3.5 parts, WFI. The suspension step is typically done at a temperature between 0° C. and 8° C. to achieve an $AU_{280-320}$ value of from 40 to 95. The final pH of the solution, which is stirred for at least 2 hours, is then adjusted to from 4.5 to 5.6, preferably to 5.2±0.2. In one embodiment, this pH adjustment is performed with acetic acid. To increase the solubility of IgG, the conductivity of the suspension is increased to between 2.5 and 6.0 mS/cm. In one embodiment, the conductivity is increased by the addition of sodium chloride.

Suitable solutions for the extraction of precipitate G include WFI and low conductivity buffers. In one embodiment, a low conductivity buffer has a conductivity of less than about 10 mS/cm. In other embodiments, the low conductivity buffer has a conductivity of less than about 9, 8, 7, 6, 5, 4, 3, 2, or 1 mS/cm. In a preferred embodiment, the low conductivity buffer has a conductivity of less than about 6 mS/cm. In another preferred embodiment, the low conductivity buffer has a conductivity of less than about 4 mS/cm. In another preferred embodiment, the low conductivity buffer has a conductivity of less than about 2 mS/cm.

The suspended PptG solution is then filtered with a suitable depth filter having a nominal pore size of between 0.1 μm and 0.4 μm in order to remove any undissolved particles. In one embodiment, the nominal pore size of the depth filter is about 0.2 μm (e.g., Cuno VR06 filter or equivalent). In another embodiment, the suspended PptG solution is centrifuged to recover a clarified supernatant. The filter is washed with WFI or a suitable buffer after filtration to recover additional IgG and the post-wash added to the filtrate. In a preferred embodiment, the post-wash of the filter is performed using a sodium chloride solution with a conductivity of between about 2.5 and about 6.0 mS/cm.

7. Solvent and Detergent (S/D) Treatment

In order to inactivate various viral contaminants present in plasma-derived products, the clarified PptG filtrate is next subjected to a solvent detergent (S/D) treatment. Methods for the detergent treatment of plasma derived fractions are well known in the art (for review see, Pelletier J P et al., Best Pract Res Clin Haematol. 2006; 19(1):205-42). Generally, any standard S/D treatment may be used in conjunction with the methods provided herein. For example, an exemplary protocol for an S/D treatment is provided below.

Triton X-100, Tween-20, and tri(n-butyl)phosphate (TNBP) are added to the clarified PptG filtrate at final concentrations of about 1.0%, 0.3%, and 0.3%, respectively. The mixture is then stirred at a temperature between 18° C. and 25° C. for at least an hour.

In one embodiment, the S/D reagents (e.g., Triton X-100, Tween-20, and TNBP) are added by diffuse addition. In a specific embodiment, the S/D reagents are added by spraying rather than by fluent addition. In another embodiment, the detergent reagents are added as solids to the clarified PptG filtrate, which is being mixed to ensure rapid distribution of the S/D components. In certain embodiments, it is preferable to add solid reagents by sprinkling the solids over a delocalized surface area of the filtrate such that local overconcentration does not occur, such as in fluent addition.

8. Ion Exchange Chromatography

In order to further purify and concentrate IgG, cation exchange and/or anion exchange chromatography can be employed. Methods for purifying and concentrating IgG using ion exchange chromatography are well known in the art. For example, U.S. Pat. No. 5,886,154 describes a method in which a Fraction II+III precipitate is extracted at low pH (between about 3.8 and 4.5), followed by precipitation of IgG using caprylic acid, and finally implementation of two anion exchange chromatography steps. U.S. Pat. No. 6,069,236 describes a chromatographic IgG purification scheme that does not rely on alcohol precipitation at all. PCT Publication No. WO 2005/073252 describes an IgG purification method involving the extraction of a Fraction II+III precipitate, caprylic acid treatment, PEG treatment, and a single anion exchange chromatography step. U.S. Pat. No. 7,186,410 describes an IgG purification method involving the extraction of a Fraction I+II+III or Fraction II precipitate followed by a single anion exchange step performed at an alkaline pH. U.S. Pat. No. 7,553,938 describes a method involving the extraction of a Fraction I+II+III or Fraction II+III precipitate, caprylate treatment, and either one or two anion exchange chromatography steps. U.S. Pat. No. 6,093,324 describes a purification method comprising the use of a macroporous anion exchange resin operated at a pH between about 6.0 and about 6.6. U.S. Pat. No. 6,835,379 describes a purification method that relies on cation exchange chromatography in the absence of alcohol fractionation. The disclosures of the above publications are hereby incorporated by reference in their entireties for all purposes In one embodiment, the S/D treated PptG filtrate may be subjected to both cation exchange chromatography and anion exchange chromatography. For example, in one embodiment, the S/D treated PptG filtrate is contacted by a cation exchange resin under suitable conditions to binds the IgG to the resin. The S/D reagents can then be washed away from the adsorbed IgG, which is subsequently eluted off of the resin with a suitable elution buffer. In this fashion, the cation exchange chromatography step can be used to remove the S/D reagents from the preparation, concentrate the IgG containing solution, and/or remove impurities from the composition.

In one embodiment, IgG is eluted from the cation exchange resin using an elution buffer having a pH between about 8.0 and 9.0. In certain embodiments, the pH elution buffer may have a pH between about 8.2 and about 8.8, or between about 8.4 and about 8.6, or a pH of about 8.0, 8.1, 8.2, 8.3, 8.4, 8.5, 8.6, 8.7, 8.8, 8.9, or 9.0. In a preferred embodiment, the pH of the elution buffer is about 8.5±0.1.

Likewise, anion exchange chromatography can be used to reduce impurities in the IgG composition. In one embodiment, anion exchange chromatography is performed under solution conditions in which one or more impurities bind to the anion exchange resin but IgG does not. In a specific embodiment, anion exchange chromatography is performed at slightly acidic conditions, i.e., at a pH between 5.0 and 7.0, preferably between 5.5 and 6.5, at a low ionic strength suitable for binding of contaminants but not IgG to the anion exchange resin.

In a specific embodiment, the eluate from the cation exchange column may be adjusted to a lower pH, for example between about 5.5 and about 6.5, and diluted with an appropriate buffer such that the conductivity of the solution is reduced. In certain embodiments, the pH of the cation exchange eluate may be adjusted to a pH between about 5.7 and about 6.7, or between about 5.9 and about 6.5, or a pH of about 5.5, 5.6, 5.7, 5.8, 5.9, 6.0, 6.1, 6.2, 6.3, 6.4, 6.5, 6.6, or 6.7. In a preferred embodiment, the pH of the eluate is adjusted to a pH of about 6.4±0.1. The eluate is then loaded onto an anion exchange column, which binds several contaminants found in the preparation. The column flow through, containing the IgG fraction, is collected during column loading and washing. In certain embodiments, the ion exchange chromatographic steps of the present invention can be performed in column mode, batch mode, or in a combination of the two. In one embodiment, the solution used to adjust the pH of the IgG composition prior to anion exchange chromatography is added by diffuse addition. In a specific embodiment, the solution is added by spraying, rather than by fluent addition.

9. Nanofiltration

In order to reduce the viral load of an IgG composition provided herein, the composition may be nanofiltered using a suitable nanofiltration device. In certain embodiments, the nanofiltration device will have a mean pore size of between about 15 nm and about 200 nm. Examples of nanofilters suitable for this use include, without limitation, DVD, DV 50, DV 20 (Pall), Viresolve NFP, Viresolve NFR (Millipore), Planova 15N, 20N, 35N, and 75N (Planova). In a specific embodiment, the nanofilter may have a mean pore size of between about 15 nm and about 72 nm, or between about 19 nm and about 35 nm, or of about 15 nm, 19 nm, 35 nm, or 72 nm. In a preferred embodiment, the nanofilter will have a mean pore size of about 35 nm, such as an Asahi PLANOVA 35N filter or equivalent thereof. In a particular embodiment, the IgG composition recovered from the anion exchange step is nanofiltered using a nanofilter having a pore size between 30 nm and 40 nm, preferably 35±2 nm. In another preferred embodiment, the nanofilter will have a mean pore size of about 19 or 20 nm, such as an Asahi PLANOVA 20N filter (19±2 nm) or equivalent thereof. In a particular embodiment, the IgG composition recovered from the anion exchange step is nanofiltered using a nanofilter having a pore size between 15 nm and 25 nm, preferably 19±2 nm.

10. Ultra-/Diafiltration (UF/DF)

Ultrafiltration/diafiltration may be performed to concentrate the IgG composition at any step during the purification process. In one embodiment, the nanofiltrate is concentrated by UF/DF. In one embodiment, the nanofiltrate may be concentrated by ultrafiltration to a protein concentration of between about 2% and about 10% (w/v). In certain embodiments, the ultrafiltration is carried out in a cassette with an open channel screen and the ultrafiltration membrane has a nominal molecular weight cut off (NMWCO) of less than about 100 kDa or less than about 90, 80, 70, 60, 50, 40, 30, or fewer kDa. In a preferred embodiment, the ultrafiltration membrane has a NMWCO of no more than 50 kDa.

In one embodiment, an open channel membrane is used with a specifically designed post-wash and formulation near the end the production process to render the resulting IgG compositions about twice as high in protein concentration (200 mg/mL) compared to state of the art IVIGs (e.g., GAMMAGARD® LIQUID, 10% IgG) without affecting yield and storage stability. With most of the commercial available ultrafiltration membranes a concentration of 200 mg/mL IgG cannot be reached without major protein losses. These membranes are blocked early and therefore adequate post-wash is difficult to achieve. Therefore open channel membrane configurations have to be used. Even with open channel membranes, a specifically designed post-wash procedure has to be used to obtain the required concentration without significant protein loss (less than 2% loss). Even more surprising is the fact that the higher protein concentration of 200 mg/mL does not reduce the virus inactivation capacity of a low pH storage step.

Upon completion of the ultrafiltration step, the concentrate may further be concentrated via diafiltration against a solution suitable for intravenous or intramuscular administration. In certain embodiments, the diafiltration solution may comprise a stabilizing and/or buffering agent. In a preferred embodiment, the stabilizing and buffering agent is glycine at an appropriate concentration, for example between about 0.20 M and about 0.30 M, or between about 0.22 M and about 0.28 M, or between about 0.24 M and about 0.26 M, or at a concentration of 0.20±0.01 M, 0.21±0.01 M, 0.22±0.01 M, 0.23±0.01 M, 0.24±0.01 M, 0.25±0.01 M, 0.26±0.01 M, 0.27±0.01 M, 0.28±0.01 M, 0.29±0.01 M, or 0.3±0.01 M. In a preferred embodiment, the diafiltration buffer contains 0.25±0.01 M glycine.

Typically, the minimum exchange volume for diafiltration is at least about 3 times the original concentrate volume or at least about 4, 5, 6, 7, 8, 9, or more times the original concentrate volume. The IgG solution may be concentrated to a final protein concentration of between about 5% and about 25% (w/v), or between about 6% and about 18% (w/v), or between about 7% and about 16% (w/v), or between about 8% and about 14% (w/v), or between about 9% and about 12%, or to a final concentration of about 5%, or 6%, 7%, 8%, 9%, 10%, 11%, 12%, 13%, 14%, 15%, 16%, 17%, 18%, 19%, 20%, 21%, 22%, 23%, 24%, 25% or higher. In one embodiment, a final protein concentration of at least about 23% is achieved without adding the post-wash fraction to the concentrated solution. In another embodiment, a final protein concentration of at least about 24% is achieved without adding the post-wash fraction to the concentrated solution. In another embodiment, a final protein concentration of at least about 24% is achieved without adding the post-wash fraction to the concentrated solution. In one embodiment, the pH of the solution will be from 4.6 to 5.1 after diafiltration.

In an exemplary embodiment, the pH of the IgG composition is adjusted to about 4.5 prior to ultrafiltration. The solution is concentrated to a protein concentration of 5±2% w/v through ultrafiltration. The UF membrane has a nominal molecular weight cut off (NMWCO) of 50,000 Daltons or less (e.g., Millipore Pellicon Polyether sulfon membrane). The concentrate is then diafiltered against ten volumes of 0.25 M glycine solution, pH 4.5±0.2. Throughout the ultra-diafiltration operation the solution is maintained at a temperature of between about 2° C. to about 8° C. After diafiltration, the solution is concentrated to a protein concentration of at least 11% (w/v).

11. Formulation

Upon completion of the diafiltration step, the protein concentration of the solution is adjusted to with the diafiltration buffer to a final concentration of between about 5% and about 20% (w/v), or between about 6% and about 18% (w/v), or between about 7% and about 16% (w/v), or between about 8% and about 14% (w/v), or between about 9% and about 12%, or to a final concentration of about 5%, or 6%, 7%, 8%, 9%, 10%, 11%, 12%, 13%, 14%, 15%, 16%, 17%, 18%, 19%, 20%, 21%, 22%, 23%, 24%, or 25%. In one embodiment, the final protein concentration of the solution is between about 9% and about 11%, more preferably about 10%.

The formulated bulk solution is further sterilized by filtering through a membrane filter with an absolute pore size of no more than about 0.22 micron, for example about 0.2 micron. Then the solution is aseptically dispensed into final containers for proper sealing, with samples taken for testing.

In one embodiment, the IgG composition is further adjusted to a concentration of 10.2±0.2% (w/v) with diafiltration buffer. In another embodiment, the IgG composition is adjusted to a concentration of 15±1% (w/v). In another embodiment, the IgG composition is adjusted to a concentration of 20±1% (w/v). In another embodiment, the IgG composition is adjusted to a concentration of 25±1% (w/v).

The pH is adjusted to about 4.4 to about 4.9 if necessary. Finally, the solution is sterile filtered and incubated for three weeks at or about 30° C.

D. Immunoglobulin G (IgG)

In one aspect, the present invention provides a method for preparing an enriched immunoglobulin G (IgG) composition from a Cohn pool, the method comprising the steps of: co-precipitating IgG and alpha-1-antitrypsin (A1PI) from a Cohn pool, in a first precipitation step, to form a first precipitate and a first supernatant; suspending the first precipitate to form a first suspension; removing the A1PI from the suspension; and recovering the soluble fraction of the first suspension containing IgG, thereby forming an enriched IgG composition. Generally, any chemical means for the precipitation of immunoglobulins and A1PI may be used, including but not limited to, alcohol precipitation (e.g., using ethanol or methanol), precipitation using water soluble polymers (e.g., PEG or dextran), and salting out (e.g., using ammonium phosphate, ammonium sulfate, sodium citrate, etc.). In a preferred embodiment, the precipitation is alcohol precipitation, preferably ethanol precipitation.

In one embodiment, the present invention provides a method for preparing an enriched immunoglobulin G (IgG) composition by precipitating IgG from cryo-poor plasma in a low pH, high alcohol precipitation step. In a specific embodiment, the method comprises the steps of: precipitating IgG from cryo-poor plasma in a first precipitation step by adding ethanol to the cryo-poor plasma to a final concentration of between 20% and 30% at a pH from 5.0 to 6.0 to form a first precipitate and a first supernatant; separating the first precipitate from the first supernatant; and recovering IgG from the first precipitate, thereby forming an enriched IgG composition. In one embodiment, ethanol is admixed with the Cohn pool to a final concentration of 25±3% (v/v). In one embodiment, IgG recovered from the first precipitate is further enriched.

In one embodiment, the method comprises the steps of: precipitating IgG from cryo-poor plasma in a first precipitation step by adding ethanol to the cryo-poor plasma to a final concentration and pH selected from variations 1 to 2166, as listed in Table 1, Table 2, Table 3, Table 4, Table 5, Table 6, and Table 7 to form a first precipitate and a first supernatant; separating the first precipitate from the first supernatant; and recovering IgG from the first precipitate, thereby forming an enriched IgG composition. In one embodiment, IgG recovered from the first precipitate is further enriched.

In one embodiment, the first precipitation step is performed by admixing ethanol with the Cohn pool to a final concentration of from 20% to 30% (v/v) at a pH between 5.0 and 6.0. In one embodiment, ethanol is admixed with the Cohn pool to a final concentration of 25±3% (v/v). In another embodiment, ethanol is admixed with the Cohn pool to a final concentration of 25±2% (v/v). In another embodiment, ethanol is admixed with the Cohn pool to a final concentration of 25±1% (v/v). In another embodiment, ethanol is admixed with the Cohn pool to a final concentration of 25% (v/v). Likewise, in one embodiment, the first precipitation step is performed at a pH of 5.5±0.5. In another embodiment, the first precipitation step is performed at a pH of 5.5±0.4. In another embodiment, the first precipitation step is performed at a pH of 5.5±0.3. In another embodiment, the first precipitation step is performed at a pH of 5.5±0.2. In another embodiment, the first precipitation step is performed at a pH of 5.5±0.1. In another embodiment, the first precipitation step is performed at a pH of 5.5. In yet other embodiments, the final ethanol concentration and pH of the first precipitation step is selected from variations 1 to 2166, as listed in Table 1, Table 2, Table 3, Table 4, Table 5, Table 6, and Table 7.

The methods provided herein provide significantly higher yields of IgG recovery in the final enriched product due to the precipitation of a majority of the immunoglobulin content of the starting Cohn pool in the initial precipitation reaction, as compared to state of the art purification procedures that rely on initial low alcohol precipitation steps (i.e., Fraction I precipitation).

Accordingly, in one embodiment of the methods provided herein, at least 90% of the IgG content of the starting Cohn pool is precipitated in the initial precipitation reaction. In a preferred embodiment, at least 95% of the IgG content of the starting Cohn pool is precipitated in the initial precipitation reaction. In a more preferred embodiment, at least 99% of the IgG content of the starting Cohn pool is precipitated in the initial precipitation reaction. In certain embodiments, at least 90%, 91%, 92%, 93%, 94%, 95%, 96%, 97%, 98%, 99%, or more of the IgG content of the starting Cohn pool is precipitated in the initial precipitation reaction.

As shown in the examples provided herein, the use of an initial low pH, high alcohol precipitation step (i.e., Fraction I-IV-1 precipitation) results in the precipitation of at least 99% of the IgG content of the starting Cohn pool. Accordingly, in one embodiment, the present invention provides a method for preparing an enriched IgG composition, the method comprising the steps of: precipitating from 99% to 100% of the IgG content from a Cohn pool in a first precipitation step by adding ethanol to the Cohn pool to a final concentration of between 20% and 30% at a pH from 5.0 to 6.0 to form a first precipitate and a first supernatant; separating the first precipitate from the first supernatant; and recovering IgG from the first precipitate, thereby forming an enriched immunoglobulin composition. In one embodiment, ethanol is admixed with the Cohn pool to a final concentration of 25±3% (v/v). In one embodiment, IgG recovered from the first precipitate is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7.

In one embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; removing the A1PI from the suspension; and recovering the soluble fraction of the first suspension, thereby forming an enriched IgG composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step.

In one embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; removing the A1PI from the suspension; and recovering the soluble fraction of the first suspension, wherein from 80% to 100% of the albumin content of the Cohn pool is present in the first supernatant, thereby forming an enriched IgG composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7.

In order to provide pharmaceutical grade IgG compositions, contaminants such as A1PI and fibrinogen present in the initial precipitate need to be removed from the immunoglobulin composition. This may be achieved, for example, by further fractionation of the first precipitate (e.g., by differential precipitation using alcohol, non-ionic hydrophilic polymers, or salting-out), chromatographic methodologies, or filtration methodologies.

In one embodiment, the first precipitate is suspended in Water for Injection (WFI) or a low ionic strength buffer suitable to extract IgG from the precipitate, the suspension is then treated with finely divided silicon dioxide ($SiO_2$), and the soluble portion of the suspension containing the IgG is separated from the insoluble portion of the suspension containing the bulk of the A1PI and fibrinogen.

Suitable solutions for the extraction of the first precipitate will generally have a pH between 4.0 and 5.5. In certain embodiments, the solution will have a pH between 4.5 and 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer is 4.7±0.1. In another preferred embodiment, the pH of the extraction buffer is 4.8±0.1. In another preferred embodiment, the pH of the extraction buffer is 4.9±0.1. Generally, these pH requirements can be met using a buffering agent selected from, for example, acetate, citrate, monobasic phosphate, dibasic phosphate, mixtures thereof, and the like. Suitable buffer concentrations typically range from 5 to 100 mM, or from 10 to 50 mM, or 5, 10, 15, 20, 25, 30, 35, 40, 45, 50, 55, 60, 65, 70, 75, 80, 85, 90, 95, or 100 mM buffering agent.

The extraction buffer will preferably have a conductivity of from 0.5 mS/cm to 2.0 mS/cm. For example, in certain embodiments, the conductivity of the extraction buffer will be 0.5±0.1 mS/cm, or 0.6±0.1, 0.7±0.1, 0.8±0.1, 0.9±0.1, 1.0±0.1, 1.1±0.1, 1.2±0.1, 1.3±0.1, 1.4±0.1, 1.5±0.1, 1.6±0.1, 1.7±0.1, 1.8±0.1, 1.9±0.1, or 2.0±0.1 mS/cm. One of ordinary skill in the art will know how to generate extraction buffers having an appropriate conductivity. In one particular embodiment, the extraction buffer contains 5 mM monobasic sodium phosphate and 5 mM acetate at a pH of 4.8±0.2 and conductivity of from 0.7 to 0.9 mS/cm.

In one embodiment, fumed silica is added prior to separation (e.g., filtration or centrifugation) at a concentration of between 20 g/kg Fraction I-IV-1 precipitate and 100 g/kg Fraction I-IV-1 precipitate. In another embodiment, fumed silica is added at a concentration of between 30 g/kg Fraction I-IV-1 precipitate and 80 g/kg Fraction I-IV-1 precipitate. In certain embodiments, the fumed silica may be added at a concentration of about 20 g/kg Fraction I-IV-1 precipitate, or about 25, 30, 35, 40, 45, 50, 55, 60, 65, 70, 75, 80, 85, 90, 95, or 100 g/kg Fraction I-IV-1 precipitate. In one specific embodiment, fumed silica (e.g., Aerosil 380 or equivalent) is added to the Fraction I-IV-1 suspension to a final concentration of 40±20 g/kg Fraction I-IV-1 precipitate. In another specific embodiment, fumed silica is added to the Fraction I-IV-1 suspension to a final concentration of 40±10 g/kg Fraction I-IV-1 precipitate. Mixing takes place at 2° C. to 8° C. for at least 50 to 70 minutes.

Accordingly, in one embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains IgG and the insoluble portion of the suspension contains A1PI, fibrinogen, Factor H, and IaIp, thereby forming an enriched IgG composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In a specific embodiment, the soluble and insoluble portions of the first suspension are separated by filtration. In one embodiment, $SiO_2$ is added to a final concentration of 40±10 g/kg Fraction I-IV-1 precipitate.

In one embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains IgG and the insoluble portion of the suspension contains A1PI, fibrinogen, Factor H, and IaIp, and further wherein from 80% to 100% of the albumin content of the Cohn pool is present in the first supernatant, thereby forming an enriched IgG composition. In one embodiment, ethanol is admixed with the Cohn pool to a final concentration of 25±3% (v/v). In one embodiment, IgG present in the soluble portion of the suspension is further enriched. In another embodiment, A1PI present in the insoluble portion of the suspension is further enriched. In another embodiment, fibrinogen present in the insoluble portion of the suspension is further enriched. In another embodiment, Factor H present in the insoluble portion of the suspension is further enriched. In another embodiment, IaIp present in the insoluble portion of the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a specific embodiment, the soluble and insoluble portions of the first suspension are separated by filtration. In one embodiment, $SiO_2$ is added to a final concentration of 40±10 g/kg Fraction I-IV-1 precipitate.

In one embodiment, IgG recovered from the soluble portion of the first suspension is further enriched by fractionation. Generally, any method of fractionation (e.g., alcohol or polymer precipitation, salting out, etc.) may be used. In a preferred embodiment, IgG is further enriched by fractionating the soluble portion of the first suspension by ethanol precipitation. In one embodiment, IgG is enriched by the addition of ethanol to the soluble portion of the first suspension at a final concentration and pH suitable to precipitate the IgG, while at least one contaminant is not precipitated. In another embodiment, IgG is enriched by the addition of ethanol to the soluble portion of the first suspension at a final concentration and pH suitable to precipitate at least one contaminant, while IgG is not precipitated.

In one embodiment, the present invention provides a method for preparing an enriched IgG composition from a Cohn pool, the method comprising the steps of: co-precipitating IgG and alpha-1-antitrypsin (A1PI) from a Cohn pool, in a first precipitation step, to form a first precipitate and a first supernatant; suspending the first precipitate to form a first suspension; removing A1PI from the suspension; precipitating IgG from the first suspension in a second precipitation step, to form a second precipitate comprising IgG and a second supernatant comprising at least one contaminant; and recovering IgG from the second precipitate, thereby forming an enriched IgG composition. In one embodiment, IgG recovered from the second precipitate is further enriched. In another embodiment, A1PI removed from the first suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7.

In an exemplary embodiment, the second precipitation step is performed by admixing ethanol to the soluble portion of the second suspension (e.g., a filtrate or supernatant of the suspension formed after filtration or centrifugation) at a final concentration of from 22% to 28% (v/v) at a pH between 6.5 and 7.5. In one embodiment, ethanol is admixed to a final concentration of 25±3% (v/v). In another embodiment, ethanol is admixed to a final concentration of 25±2% (v/v). In another embodiment, ethanol is admixed to a final concentration of 25±1% (v/v). In another embodiment, ethanol is admixed to a final concentration of 25% (v/v). Likewise, in one embodiment, the second precipitation step is performed at a pH of 7.0±0.5. In another embodiment, the second precipitation step is performed at a pH of 7.0±0.4. In another embodiment, the second precipitation step is performed at a pH of 7.0±0.3. In another embodiment, the second precipitation step is performed at a pH of 7.0±0.2. In another embodiment, the second precipitation step is performed at a pH of 7.0±0.1. In another embodiment, the second precipitation step is performed at a pH of 7.0. In a particular embodiment, the second precipitation step is performed using a final ethanol concentration of 25±3% (v/v) at a pH of 7.0±0.3.

In a particular embodiment, the method comprises the steps of: precipitating from 99% to 100% of IgG content from a Cohn pool plasma in a first precipitation step by adding ethanol to the Cohn pool to a final concentration of between 20% and 30% at a pH from 5.0 to 6.0 to form a first precipitate and a first supernatant; separating the first precipitate from the first supernatant; suspending the first precipitate to form a first suspension; precipitating IgG from the first suspension in a second precipitation step, to form a second precipitate comprising IgG and a second supernatant comprising at least one contaminant; and recovering IgG from the second precipitate, thereby forming an enriched IgG composition. In one embodiment, ethanol is admixed with the Cohn pool to a final concentration of 25±3% (v/v). In one embodiment, IgG recovered from the second precipitate is further enriched. In certain embodiments, the final ethanol concentration and pH used in the first precipitation step is selected from variations 1 to 2166, as listed in Table 1, Table 2, Table 3, Table 4, Table 5, Table 6, and Table 7.

In a specific embodiment, the method comprises the steps of: precipitating from 99% to 100% of IgG content from a Cohn pool plasma in a first precipitation step by adding ethanol to the Cohn pool to a final concentration of between 20% and 30% at a pH from 5.0 to 6.0 to form a first precipitate and a first supernatant; separating the first precipitate from the first supernatant; suspending the first precipitate to form a first suspension; precipitating IgG from the first suspension in a second precipitation step by admixing ethanol to the first suspension at a final concentration of from 25±3% (v/v) at a pH of 7.0±0.3, to form a second precipitate comprising IgG and a second supernatant comprising at least one contaminant; and recovering IgG from the second precipitate, thereby forming an enriched IgG composition. In one embodiment, ethanol is admixed with the Cohn pool to a final concentration of 25±3% (v/v). In one embodiment, IgG recovered from the second precipitate is further enriched. In certain embodiments, the final ethanol concentration and pH used in the first precipitation step is selected from variations 1 to 2166, as listed in Table 1, Table 2, Table 3, Table 4, Table 5, Table 6, and Table 7.

In one embodiment, the method comprises the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; removing A1PI from the suspension; recovering the soluble fraction of the first suspension; precipitating IgG from the first suspension in a second precipitation step, to form a second precipitate comprising IgG and a second supernatant comprising at least one contaminant; and recovering IgG from the second precipitate, thereby forming an enriched IgG composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step.

In a specific embodiment, the method comprises the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; removing A1PI from the suspension; recovering the soluble fraction of the first suspension; precipitating IgG from the first suspension in a second precipitation step by admixing ethanol to the first suspension at a final concentration of from 25±3% (v/v) at a pH of 7.0±0.3, to form a second precipitate comprising IgG and a second supernatant comprising at least one contaminant; and recovering IgG from the second precipitate, thereby forming an enriched IgG composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step.

In another embodiment, the method comprises the steps of: precipitating from 99% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; removing the A1PI from the suspension; recovering the soluble portion of the first suspension; precipitating IgG from the soluble portion of the first suspension in a second precipitation step, to form a second precipitate comprising IgG and a second supernatant comprising at least one contaminant; and recovering IgG from the second precipitate, wherein from 80% to 100% of the albumin content of the Cohn pool is present in the first supernatant, thereby forming an enriched IgG composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In another embodiment, albumin present in the first supernatant is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step. In a preferred embodiment, between 90% and 100% of the albumin content of the Cohn pool is present in the first supernatant.

In another embodiment, the method comprises the steps of: precipitating from 99% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; removing the A1PI from the suspension; recovering the soluble portion of the first suspension; precipitating IgG from the soluble portion of the first suspension in a second precipitation step by admixing ethanol to the soluble portion of the first suspension at a final concentration of from 25±3% (v/v) at a pH of 7.0±0.3, to form a second precipitate comprising IgG and a second supernatant comprising at least one contaminant; and recovering IgG from the second precipitate, wherein from 80% to 100% of the albumin content of the Cohn pool is present in the first supernatant, thereby forming an enriched IgG composition. In one embodiment, ethanol is admixed with the Cohn pool to a final concentration of 25±3% (v/v). In one embodiment, IgG recovered from the second precipitate is further enriched. In one embodiment, A1PI separated from the first suspension is further enriched. In another embodiment, albumin present in the first supernatant is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, between 99% and 100% of the IgG content of the Cohn pool is precipitated in the first precipitation step. In a preferred embodiment, between 90% and 100% of the albumin content of the Cohn pool is present in the first supernatant.

In one embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains IgG and the insoluble portion of the suspension contains A1PI, fibrinogen, Factor H, and IaIp, recovering the soluble portion of the first suspension; precipitating IgG from the soluble portion of the first suspension in a second precipitation step, to form a second precipitate comprising IgG and a second supernatant comprising at least one contaminant; and recovering IgG from the second precipitate, thereby forming an enriched IgG composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In a specific embodiment, the soluble and insoluble portions of the first suspension are separated by filtration. In one embodiment, $SiO_2$ is added to a final concentration of 40±10 g/kg Fraction I-IV-1 precipitate.

In a specific embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains IgG and the insoluble portion of the suspension contains A1PI, fibrinogen, Factor H, and IaIp, recovering the soluble portion of the first suspension; precipitating IgG from the soluble portion of the first suspension in a second precipitation step by admixing ethanol to the soluble portion of the first suspension at a final concentration of from 25±3% (v/v) at a pH of 7.0±0.3, to form a second precipitate comprising IgG and a second supernatant comprising at least one contaminant; and recovering IgG from the second precipitate, thereby forming an enriched IgG composition. In one embodiment, ethanol is admixed with the Cohn pool to a final concentration of 25±3% (v/v). In one embodiment, IgG recovered from the first precipitate is further enriched. In another embodiment, A1PI removed from the suspension is further enriched. In certain embodiments, the final ethanol concentration and pH used in the first precipitation step is selected from variations 1 to 2166, as listed in Table 1, Table 2, Table 3, Table 4, Table 5, Table 6, and Table 7. In a preferred embodiment, from 99% to 100% of the IgG content of the Cohn pool is precipitated in the first precipitation step. In a specific embodiment, the soluble and insoluble portions of the first suspension are separated by filtration. In one embodiment, $SiO_2$ is added to a final concentration of 40±10 g/kg Fraction I-IV-1 precipitate.

In one embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains IgG and the insoluble portion of the suspension contains A1PI, fibrinogen, Factor H, and IaIp; precipitating IgG from the soluble portion of the first suspension in a second precipitation step, to form a second precipitate comprising IgG and a second supernatant comprising at least one contaminant; and recovering IgG from the second precipitate, wherein from 80% to 100% of the albumin content of the Cohn pool is present in the first supernatant, thereby forming an enriched IgG composition. In one embodiment, ethanol is admixed with the Cohn pool to a final concentration of 25±3% (v/v). In one embodiment, IgG recovered from the second precipitate is further enriched. In another embodiment, A1PI present in the insoluble portion of the suspension is further enriched. In another embodiment, fibrinogen present in the insoluble portion of the suspension is further enriched. In another embodiment, Factor H present in the insoluble portion of the suspension is further enriched. In another embodiment, IaIp present in the insoluble portion of the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the first precipitation step is selected from variations 1 to 2166, as listed in Table 1, Table 2, Table 3, Table 4, Table 5, Table 6, and Table 7. In a specific embodiment, the soluble and insoluble portions of the first suspension are separated by filtration. In one embodiment, $SiO_2$ is added to a final concentration of 40±10 g/kg Fraction I-IV-1 precipitate.

In one embodiment, the present invention provides a method for preparing an enriched IgG composition, the method comprising the steps of: precipitating from 95% to 100% of IgG and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains IgG and the insoluble portion of the suspension contains A1PI, fibrinogen, Factor H, and IaIp; precipitating IgG from the soluble portion of the first suspension in a second precipitation step by admixing ethanol to the soluble portion of the first suspension at a final concentration of from 25±3% (v/v) at a pH of 7.0±0.3, to form a second precipitate comprising IgG and a second supernatant comprising at least one contaminant; and recovering IgG from the second precipitate, wherein from 80% to 100% of the albumin content of the Cohn pool is present in the first supernatant, thereby forming an enriched IgG composition. In one embodiment, ethanol is admixed with the Cohn pool to a final concentration of 25±3% (v/v). In one embodiment, IgG recovered from the second precipitate is further enriched. In another embodiment, A1PI present in the insoluble portion of the suspension is further enriched. In another embodiment, fibrinogen present in the insoluble portion of the suspension is further enriched. In another embodiment, Factor H present in the insoluble portion of the suspension is further enriched. In another embodiment, IaIp present in the insoluble portion of the suspension is further enriched. In yet another embodiment, albumin found in the first supernatant is further enriched. In a preferred embodiment, from 99% to 100% of the IgG content of the Cohn pool is precipitated in the first precipitation step. In certain embodiments, the final ethanol concentration and pH used in the first precipitation step is selected from variations 1 to 2166, as listed in Table 1, Table 2, Table 3, Table 4, Table 5, Table 6, and Table 7. In a specific embodiment, the soluble and insoluble portions of the first suspension are separated by filtration. In one embodiment, $SiO_2$ is added to a final concentration of 40±10 g/kg Fraction I-IV-1 precipitate.

In one embodiment, IgG are recovered from the second precipitate by suspending the precipitate with a cold extraction buffer. For example, the second precipitate is suspended at a ratio of 1 part precipitate to 2-5 parts Water for Injection (WFI) or low conductivity buffer. In a preferred embodiment, the second precipitate suspended at a ratio of 1 part precipitate to 4-5 parts, preferably 3.5 parts, WFI. In one embodiment, the suspension step is performed at a temperature between 0° C. and 8° C. In one embodiment, the final pH of the solution is adjusted to from 4.8 to 5.6, preferably to 5.2±0.2. In one embodiment, this pH adjustment is performed with acetic acid. In one embodiment, the conductivity of the suspension is increased to between 2.5 and 6.0 mS/cm to increase the solubility of IgG. In one embodiment, the conductivity is increased by the addition of sodium chloride.

Suitable solutions for the extraction of the second precipitate include WFI and low conductivity buffers. In one embodiment, a low conductivity buffer has a conductivity of less than about 10 mS/cm. In other embodiments, the low conductivity buffer has a conductivity of less than about 9, 8, 7, 6, 5, 4, 3, 2, or 1 mS/cm. In a preferred embodiment, the low conductivity buffer has a conductivity of less than about 6 mS/cm. In another preferred embodiment, the low conductivity buffer has a conductivity of less than about 4 mS/cm. In another preferred embodiment, the low conductivity buffer has a conductivity of less than about 2 mS/cm.

In one embodiment, the soluble portion of the first suspension, containing IgG, is separated from the insoluble portion. In one embodiment, this is done by filtering the suspension with a depth filter having a nominal pore size of from 0.1 μm and 0.4 μm. In one embodiment, the nominal pore size of the depth filter is 0.2 μm (e.g., Cuno VR06 filter or equivalent). In one embodiment, the filter is washed with WFI or a suitable buffer after filtration to recover additional IgG and the post-wash added to the filtrate. In a preferred embodiment, the post-wash of the filter is performed using a sodium chloride solution with a conductivity of between about 2.5 and about 6.0 mS/cm. In another embodiment, the second suspension is centrifuged to recover the soluble portion.

In one aspect of the present invention, the methods provided for preparing an enriched IgG composition further comprise purifying at least one additional blood factor from the same Cohn pool. In one embodiment, the methods further comprise purifying at least two additional blood proteins from the same Cohn pool. In another embodiment, the methods further comprise purifying at least three additional blood proteins from the same Cohn pool. In yet other embodiments, the methods further comprise purifying at least four, five, six, or more additional blood proteins from the same Cohn pool. Exemplary blood proteins that may be co-purified from the same Cohn pool as IgG include, without limitation, albumin, alpha-1-antitrypsin (A1PI), Factor H, inter-alpha-inhibitor proteins (IaIp), Prothrombin complexes, Factor VII (FVII), Factor VIII (FVIII), antithrombin III (ATIII), fibrinogen, butyrylcholinesterase, and others.

In one embodiment, alpha-1-antitrypsin (A1PI) is further purified from the same Cohn pool as IgG. In a specific embodiment, A1PI is purified from the insoluble fraction of the first suspension.

In another embodiment, fibrinogen is further purified from the same Cohn pool as IgG. In a specific embodiment, fibrinogen is purified from the insoluble fraction of the first suspension. In another specific embodiment, both A1PI and fibrinogen are purified from the insoluble fraction of the first suspension.

In another embodiment, Factor H is further purified from the same Cohn pool as IgG. In a specific embodiment, Factor H is purified from the insoluble fraction of the first suspension. In another specific embodiment, both A1PI and Factor H are purified from the insoluble fraction of the first suspension.

In another embodiment, inter-alpha-inhibitor proteins (IaIp) are further purified from the same Cohn pool as IgG. In a specific embodiment, IaIp is purified from the insoluble fraction of the first suspension. In another specific embodiment, both A1PI and IaIp are purified from the insoluble fraction of the first suspension.

In another embodiment, albumin is further purified from the same Cohn pool as IgG. In a specific embodiment, albumin is purified from the first supernatant formed. In a specific embodiment, albumin is purified from the first supernatant formed, while at least one additional blood factor is purified from the insoluble portion of the first suspension formed.

In one embodiment, immunoglobulins recovered from an initial low pH, high alcohol precipitation step are further enriched according to a downstream Kistler-Nitschmann or Deutsch et al. fractionation. For example, a recovered immunoglobulin composition may be subjected to a step similar to a Kistler-Nitschmann B precipitation or Deutsch et al. β-globulin precipitation. The conditions used in these steps result in the precipitation of α- and β-globulin, while immunoglobulin G remains in the supernatant.

Accordingly, in one aspect the present invention provides a method for preparing an enriched immunoglobulin G (IgG) composition comprising the steps of (i) co-precipitating immunoglobulins and alpha-1-antitrypsin (A1PI) from a Cohn pool in an initial low pH, high alcohol precipitation; (ii) recovering immunoglobulins from the precipitate; (iii) precipitating at least one non-gamma globulin protein from the immunoglobulin composition recovered from the first precipitate; and (iv) recovering the supernatant from the second precipitation step. In certain embodiments, these methods may further comprise additional precipitation steps (e.g., a Precipitate G precipitation), an anion and/or cation exchange step, one or more ultrafiltration/diafiltration steps, and one or more viral reduction or inactivation steps (e.g., S/D treatment, nanofiltration, incubation at low pH, etc.).

V. Preparation of Alpha-1-Antitrypsin (A1PI) Compositions

Modern methods for manufacturing blood proteins from donated plasma are derived from early work done in the 1940's and 1950's. Since this work was focused primarily on the purification of albumin and gamma immunoglobulins (IgG) the fractionation schemes developed were not optimized for the recovery of additional blood proteins, which are becoming increasingly more therapeutically important. For example, the use of an initial high pH, low alcohol precipitation of plasma (e.g., Fraction I precipitation) results in the partial loss of Factor H, IaIp, and to some extent immunoglobulins in the Fraction I precipitate. Furthermore, the separation of immunoglobulins and A1PI achieved by subsequent precipitation steps (e.g., Fraction II+III precipitation or Precipitation A) is incomplete, with immunoglobulins lost in the supernatant due to incomplete precipitation and A1PI lost in the precipitate due to partial precipitation. Accordingly, updated fractionation methods that provide higher yields of multiple blood proteins are needed.

The present invention provides methods that satisfy these requirements through the use of an initial precipitation step that fractionates immunoglobulins, A1PI, and other blood proteins in an initial precipitate and albumin in an initial supernatant. In a preferred embodiment, this initial precipitation is performed under low pH, high alcohol conditions.

In one aspect, the present invention provides a method for the manufacture of alpha-1-antitrypsin (A1PI) from pooled plasma using an initial step that precipitates the bulk of the immunoglobulin and A1PI content of a Cohn pool. In a particular embodiment, this initial step is a low pH, high alcohol precipitation step. As shown in the examples provided herein, greater than 95% of the A1PI content of the starting Cohn pool is precipitated under these conditions. Furthermore, the present invention provides methods for efficiently separating A1PI and immunoglobulins in this initial precipitation.

In one aspect, the present invention provides a method for preparing an enriched alpha-1-antitrypsin (A1PI) composition from a Cohn pool, the method comprising the steps of: co-precipitating immunoglobulins and A1PI from a Cohn pool, in a first precipitation step, to form a first precipitate and a first supernatant; solubilizing immunoglobulins present in the first precipitate, to form a first suspension having a soluble portion comprising immunoglobulins and an insoluble portion comprising A1PI; separating the soluble and insoluble portions of the first suspension; and recovering A1PI from the insoluble portion of the first suspension, thereby forming an enriched A1PI composition. Generally, any chemical means for the precipitation of immunoglobulins and A1PI may be used, including but not limited to, alcohol precipitation (e.g., using ethanol or methanol), precipitation using water soluble polymers (e.g., PEG or dextran), and salting out (e.g., using ammonium phosphate, ammonium sulfate, sodium citrate, etc.). In a preferred embodiment, the precipitation is alcohol precipitation, preferably ethanol precipitation.

In one embodiment, the present invention provides a method for preparing an enriched A1PI composition by precipitating A1PI from cryo-poor plasma in a low pH, high alcohol precipitation step. In a specific embodiment, the method comprises the steps of: precipitating A1PI from cryo-poor plasma in a first precipitation step by adding ethanol to the cryo-poor plasma to a final concentration of between 20% and 30% at a pH from 5.0 to 6.0 to form a first precipitate and a first supernatant; separating the first precipitate from the first supernatant; and recovering A1PI from the first precipitate, thereby forming an enriched A1PI composition. In one embodiment, ethanol is admixed with the Cohn pool to a final concentration of 25±3% (v/v). In one embodiment, A1PI recovered from the first precipitate is further enriched.

In one embodiment, the method comprises the steps of: precipitating A1PI from a Cohn pool in a first precipitation step by adding ethanol to the Cohn pool to a final concentration and pH selected from variations 1 to 2166, as listed in Table 1, Table 2, Table 3, Table 4, Table 5, Table 6, and Table 7 to form a first precipitate and a first supernatant; separating the first precipitate from the first supernatant; and recovering A1PI from the first precipitate, thereby forming an enriched A1PI composition. In one embodiment, A1PI recovered from the first precipitate is further enriched.

In one embodiment, the first precipitation step is performed by admixing ethanol with the Cohn pool to a final concentration of from 22% to 28% (v/v) at a pH between 5.0 and 6.0. In one embodiment, ethanol is admixed with the Cohn pool to a final concentration of 25±3% (v/v). In another embodiment, ethanol is admixed with the Cohn pool to a final concentration of 25±2% (v/v). In another embodiment, ethanol is admixed with the Cohn pool to a final concentration of 25±1% (v/v). In another embodiment, ethanol is admixed with the Cohn pool to a final concentration of 25% (v/v). Likewise, in one embodiment, the first precipitation step is performed at a pH of 5.5±0.5. In another embodiment, the first precipitation step is performed at a pH of 5.5±0.4. In another embodiment, the first precipitation step is performed at a pH of 5.5±0.3. In another embodiment, the first precipitation step is performed at a pH of 5.5±0.2. In another embodiment, the first precipitation step is performed at a pH of 5.5±0.1. In another embodiment, the first precipitation step is performed at a pH of 5.5. In yet other embodiments, the final ethanol concentration and pH of the first precipitation step is selected from variations 1 to 2166, as listed in Table 1, Table 2, Table 3, Table 4, Table 5, Table 6, and Table 7.

The methods provided herein provide significantly higher yields of A1PI recovery in the final enriched product due to the precipitation of a majority of the A1PI content of the starting Cohn pool in the initial precipitation reaction, as compared to state of the art purification procedures that rely on initial low alcohol precipitation steps (i.e., Fraction I precipitation).

Accordingly, in one embodiment of the methods provided herein, at least 80% of the alpha-1-antitrypsin (A1PI) content of the starting Cohn pool is precipitated in the initial precipitation reaction. In a preferred embodiment, at least 90% of the A1PI content of the starting Cohn pool is precipitated in the initial precipitation reaction. In a more preferred embodiment, at least 95% of the A1PI content of the starting Cohn pool is precipitated in the initial precipitation reaction. In a most preferred embodiment, at least 97% of the A1PI content of the starting Cohn pool is precipitated in the initial precipitation reaction. In certain embodiments, at least 80%, 81%, 82%, 83%, 84%, 85%, 86%, 87%, 88%, 89%, 90%, 91%, 92%, 93%, 94%, 95%, 96%, 97%, 98%, 99%, or more of the A1PI content of the starting Cohn pool is precipitated in the initial precipitation reaction.

As shown in the examples provided herein, the use of an initial low pH, high alcohol precipitation step (i.e., Fraction I-IV-1 precipitation) results in the precipitation of at least 95% of the A1PI content of the starting Cohn pool. Accordingly, in one embodiment, the present invention provides a method for preparing an enriched A1PI composition, the method comprising the steps of: precipitating from 95% to 100% of the A1PI content from a Cohn pool in a first precipitation step by adding ethanol to the Cohn pool to a final concentration of between 20% and 30% at a pH from 5.0 to 6.0 to form a first precipitate and a first supernatant; separating the first precipitate from the first supernatant; and recovering A1PI from the first precipitate, thereby forming an enriched A1PI composition. In one embodiment, ethanol is admixed with the Cohn pool to a final concentration of 25±3% (v/v). In one embodiment, A1PI recovered from the first precipitate is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7.

In one embodiment, the present invention provides a method for preparing an enriched A1PI composition, the method comprising the steps of: precipitating from 95% to 100% of immunoglobulin and A1PI content from a Cohn pool in a first precipitation step by adding ethanol to the Cohn pool to a final concentration of between 20% and 30% at a pH from 5.0 to 6.0 to form a first precipitate and a first supernatant; solubilizing immunoglobulins present in the first precipitate, to form a first suspension having a soluble portion comprising immunoglobulins and an insoluble portion comprising A1PI; separating the soluble and insoluble portions of the first suspension; and recovering A1PI from the insoluble portion of the first suspension, thereby forming an enriched A1PI composition. In one embodiment, immunoglobulins recovered from the soluble portion of the first suspension are further enriched. In another embodiment, A1PI removed from the insoluble fraction of the first suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the immunoglobulin content of the Cohn pool is precipitated in the first precipitation step.

In one embodiment, the present invention provides a method for preparing an enriched A1PI composition, the method comprising the steps of: precipitating from 95% to 100% of immunoglobulin and A1PI content from a Cohn pool in a first precipitation step by adding ethanol to the Cohn pool to a final concentration of from 20% to 30% at a pH from 5.0 to 6.0 to form a first precipitate and a first supernatant; solubilizing immunoglobulins present in the first precipitate, to form a first suspension having a soluble portion comprising immunoglobulins and an insoluble portion comprising A1PI; separating the soluble and insoluble portions of the first suspension; and recovering A1PI from the insoluble portion of the first suspension, wherein from 80% to 100% of the albumin content of the Cohn pool is present in the first supernatant, thereby forming an enriched A1PI composition. In one embodiment, ethanol is admixed with the Cohn pool to a final concentration of 25±3% (v/v). In one embodiment, immunoglobulins recovered from the soluble portion of the first suspension are further enriched. In another embodiment, A1PI removed from the insoluble portion of the first suspension is further enriched. In yet another embodiment, albumin found in the first supernatant is further enriched. In a preferred embodiment, from 99% to 100% of the immunoglobulin content of the Cohn pool is precipitated in the first precipitation step. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7.

In one embodiment, the first precipitate is suspended in Water for Injection (WFI) or a low ionic strength buffer suitable to extract immunoglobulins from the precipitate, the suspension is then treated with finely divided silicon dioxide ($SiO_2$), and the soluble portion of the suspension containing the immunoglobulins is separated from the insoluble portion of the suspension containing the bulk of the A1PI content.

Suitable solutions for the extraction of immunoglobulins from the first precipitate will generally have a pH between 4.0 and 5.5. In certain embodiments, the solution will have a pH between 4.5 and 5.0, in other embodiments, the extraction solution will have a pH of about 4.0, 4.1, 4.2, 4.3, 4.4, 4.5, 4.6, 4.7, 4.8, 4.9, 5.0, 5.1, 5.2, 5.3, 5.4, or 5.5. In a preferred embodiment, the pH of the extraction buffer is 4.7±0.1. In another preferred embodiment, the pH of the extraction buffer is 4.8±0.1. In another preferred embodiment, the pH of the extraction buffer is 4.9±0.1. Generally, these pH requirements can be met using a buffering agent selected from, for example, acetate, citrate, monobasic phosphate, dibasic phosphate, mixtures thereof, and the like. Suitable buffer concentrations typically range from 5 to 100 mM, or from 10 to 50 mM, or 5, 10, 15, 20, 25, 30, 35, 40, 45, 50, 55, 60, 65, 70, 75, 80, 85, 90, 95, or 100 mM buffering agent.

The extraction buffer will preferably have a conductivity of from 0.5 mS/cm to 2.0 mS/cm. For example, in certain embodiments, the conductivity of the extraction buffer will be 0.5±0.1 mS/cm, or 0.6±0.1, 0.7±0.1, 0.8±0.1, 0.9±0.1, 1.0±0.1, 1.1±0.1, 1.2±0.1, 1.3±0.1, 1.4±0.1, 1.5±0.1, 1.6±0.1, 1.7±0.1, 1.8±0.1, 1.9±0.1, or 2.0±0.1 mS/cm. One of ordinary skill in the art will know how to generate extraction buffers having an appropriate conductivity. In one particular embodiment, the extraction buffer contains 5 mM monobasic sodium phosphate and 5 mM acetate at a pH of 4.8±0.2 and conductivity of from 0.7 to 0.9 mS/cm.

In one embodiment, fumed silica is added prior to separation (e.g., filtration or centrifugation) at a concentration of between 20 g/kg Fraction I-IV-1 precipitate and 100 g/kg Fraction I-IV-1 precipitate. In another embodiment, fumed silica is added at a concentration of between 30 g/kg Fraction I-IV-1 precipitate and 80 g/kg Fraction I-IV-1 precipitate. In certain embodiments, the fumed silica may be added at a concentration of about 20 g/kg Fraction I-IV-1 precipitate, or about 25, 30, 35, 40, 45, 50, 55, 60, 65, 70, 75, 80, 85, 90, 95, or 100 g/kg Fraction I-IV-1 precipitate. In one specific embodiment, fumed silica (e.g., Aerosil 380 or equivalent) is added to the Fraction I-IV-1 suspension to a final concentration of 40±20 g/kg Fraction I-IV-1 precipitate. In another specific embodiment, fumed silica is added to the Fraction I-IV-1 suspension to a final concentration of 40±10 g/kg Fraction I-IV-1 precipitate. Mixing takes place at 2° C. to 8° C. for at least 50 to 70 minutes.

Accordingly, in one embodiment, the present invention provides a method for preparing an enriched A1PI composition, the method comprising the steps of: precipitating from 95% to 100% of immunoglobulin and A1PI content from a Cohn pool in a first precipitation step by adding ethanol to the Cohn pool to a final concentration of between 20% and 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI; and recovering A1PI from the insoluble portion of the first suspension, thereby forming an enriched A1PI composition. In one embodiment, ethanol is admixed with the Cohn pool to a final concentration of 25±3% (v/v). In one embodiment, immunoglobulins recovered from the first precipitate are further enriched. In another embodiment, A1PI removed from the suspension is further enriched. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a preferred embodiment, from 99% to 100% of the immunoglobulin content of the Cohn pool is precipitated in the first precipitation step. In a specific embodiment, the soluble and insoluble portions of the first suspension are separated by filtration. In one embodiment, $SiO_2$ is added to a final concentration of 40±10 g/kg Fraction I-IV-1 precipitate.

In one embodiment, the present invention provides a method for preparing an enriched A1PI composition, the method comprising the steps of: precipitating from 95% to 100% of immunoglobulin and A1PI content from a Cohn pool in a first precipitation step by adding ethanol to the Cohn pool to a final concentration of from 20% to 30% at a pH from 5.0 to 6.0 to form a first precipitate and a first supernatant; suspending the first precipitate to form a first suspension; treating the first suspension with finely divided silicon dioxide; and separating the soluble portion of the suspension from the insoluble portion of the suspension, wherein the soluble portion of the suspension contains immunoglobulins and the insoluble portion of the suspension contains A1PI, fibrinogen, Factor H, and IaIp, and further wherein from 80% to 100% of the albumin content of the Cohn pool is present in the first supernatant. In one embodiment, ethanol is admixed with the Cohn pool to a final concentration of 25±3% (v/v). In one embodiment, immunoglobulins present in the soluble portion of the suspension are further enriched. In another embodiment, A1PI present in the insoluble portion of the suspension is further enriched. In another embodiment, fibrinogen present in the insoluble portion of the suspension is further enriched. In another embodiment, Factor H present in the insoluble portion of the suspension is further enriched. In another embodiment, IaIp present in the insoluble portion of the suspension is further enriched. In yet another embodiment, albumin found in the first supernatant is further enriched. In a preferred embodiment, from 99% to 100% of the immunoglobulin content of the Cohn pool is precipitated in the first precipitation step. In certain embodiments, the final ethanol concentration and pH used in the low pH, high alcohol precipitation step is selected from variations 1 to 2166, as listed in Table 1, Table 2, Table 3, Table 4, Table 5, Table 6, and Table 7. In a specific embodiment, the soluble and insoluble portions of the first suspension are separated by filtration. In one embodiment, $SiO_2$ is added to a final concentration of 40±10 g/kg Fraction I-IV-1 precipitate.

In one embodiment, the soluble portion of the first suspension, containing IgG, is separated from the insoluble portion, containing A1PI by filtering the suspension with a depth filter having a nominal pore size of from 0.1 μm and 0.4 μm. In one embodiment, the nominal pore size of the depth filter is 0.2 μm (e.g., Cuno VR06 filter or equivalent). In one embodiment, the filter is washed with WFI or a suitable buffer after filtration to recover additional IgG and the post-wash added to the filtrate. In another embodiment, the first suspension is centrifuged to separate the soluble and insoluble portions.

In one embodiment, A1PI is recovered from the separated insoluble portion by suspending the insoluble portion in an A1PI extraction buffer. For example, in one embodiment, the separated insoluble portion is suspended at a ratio of 1 part insoluble material to 2-15 parts Water for Injection (WFI) or low conductivity buffer, to form a second suspension. In another embodiment, the separated insoluble portion is suspended at a ratio of 1 part insoluble material to 2-10 parts Water for Injection (WFI) or low conductivity buffer. In another embodiment, the separated insoluble portion is suspended at a ratio of 1 part insoluble material to 3-7 parts Water for Injection (WFI) or low conductivity buffer. In yet other embodiments, the separated insoluble portion is suspended at a ratio of 1 part insoluble material to 2, 3, 4, 5, 6, 7, 8, 9, 10, 11, 12, 13, 14, 15, 16, 17, 18, 19, 20, or more parts Water for Injection (WFI) or low conductivity buffer. In one embodiment, the extraction is stirred for at least 2 hours. In another embodiment, the extraction is stirred for at least 4 hours. In another embodiment, the extraction is stirred for at least 8 hours. In another embodiment, the extraction is stirred for 6 to 12 hours. In one embodiment, the extraction is performed at from 10° C. to 25° C. In another embodiment, the extraction is performed at 17±5° C. In another embodiment, the extraction is performed at 17±4° C. In another embodiment, the extraction is performed at 17±3° C. In another embodiment, the extraction is performed at 17±2° C. In another embodiment, the extraction is performed at 17±1° C. In one embodiment, the soluble portion containing A1PI is separated from the insoluble portion by filtration, for example, depth filtration. In another embodiment, the soluble portion containing A1PI is separated from the insoluble portion by centrifugation.

Suitable solutions for the extraction of A1PI include WFI and low conductivity buffers. In one embodiment, a low conductivity buffer has a conductivity of less than about 10 mS/cm. In other embodiments, the low conductivity buffer has a conductivity of less than about 9, 8, 7, 6, 5, 4, 3, 2, or 1 mS/cm. In a preferred embodiment, the low conductivity buffer has a conductivity of less than about 6 mS/cm. In another preferred embodiment, the low conductivity buffer has a conductivity of less than about 4 mS/cm. In another preferred embodiment, the low conductivity buffer has a conductivity of less than about 2 mS/cm. In one embodiment, the WFI or low conductivity buffer has a pH of between 8.0 and 9.5. In a particular embodiment, the pH of the A1PI extraction buffer is 8.8±0.5. In a specific embodiment, the pH of the A1PI extraction buffer is 8.8±0.4. In a specific embodiment, the pH of the A1PI extraction buffer is 8.8±0.3. In a specific embodiment, the pH of the A1PI extraction buffer is 8.8±0.2. In a specific embodiment, the pH of the A1PI extraction buffer is 8.8±0.1. In yet other embodiments, the pH of the A1PI extraction buffer is 8.0±0.2, 8.1±0.2, 8.2±0.2, 8.3±0.2, 8.4±0.2, 8.5±0.2, 8.6±0.2, 8.7±0.2, 8.8±0.2, 8.9±0.2, 9.0±0.2, 9.1±0.2, 9.2±0.2, 9.3±0.2, 9.4±0.2, or 9.5±0.2.

In one embodiment, the separated insoluble portion of the first suspension is suspended in WFI or a low ionic strength buffer which is not suitable for extracting A1PI to form an intermediate suspension, prior to extraction using an A1PI buffer. In this embodiment, the method comprises suspending the insoluble portion in WFI or a low ionic strength buffer at a pH of no more than 7.0; separating the soluble and insoluble portions of the intermediate suspension; and recovering A1PI in the insoluble portion of the intermediate suspension. In one embodiment, the intermediate suspension is formed by suspending the insoluble material at a ratio of 1 part insoluble material to 2-15 parts WFI or buffer. In one embodiment, the WFI or low ionic strength buffer has a pH of from 4.5 to 6.5. In another embodiment, the low ionic strength buffer has a pH of 5.5±0.4. In another embodiment, the low ionic strength buffer has a pH of 5.5±0.3. In another embodiment, the low ionic strength buffer has a pH of 5.5±0.2. In another embodiment, the low ionic strength buffer has a pH of 5.5±0.1. In yet other embodiments, the low ionic strength buffer has a pH of 4.5±0.2, 4.6±0.2, 4.7±0.2, 4.8±0.2, 4.9±0.2, 5.0±0.2, 5.1±0.2, 5.2±0.2, 5.3±0.2, 5.4±0.2, 5.5±0.2, 5.6±0.2, 5.7±0.2, 5.8±0.2, 5.9±0.2, 6.0±0.2, 6.1±0.2, 6.2±0.2, 6.3±0.2, 6.4±0.2, or 6.5±0.2. In one embodiment, the soluble portion is separated from the insoluble portion containing A1PI by filtration, for example, depth filtration. In another embodiment, the soluble portion is separated from the insoluble portion containing A1PI by centrifugation.

In one embodiment, A1PI extracted from the insoluble portion of the first suspension is further enriched according to well known methods in the art, including without limitation: chromatography (e.g., anion exchange chromatography, cation exchange chromatography, hydrophobic interaction chromatography (HIC), hydroxyapatite chromatography (HAP), Protein A affinity chromatography, immuno-affinity chromatography, size exclusion chromatography, etc.); filtration (e.g., ultrafiltration and/or diafiltration); and one or more viral reduction steps (e.g., nanofiltration, solvent and detergent treatment, UV irradiation, heat treatment, low pH incubation, etc.).

In one embodiment, A1PI extracted from the insoluble portion of the first suspension is further enriched by fractionation. Generally, any method of fractionation (e.g., alcohol or polymer precipitation, salting out, etc.) may be used. In a preferred embodiment, the composition is further enriched by precipitating A1PI from the clarified extracted solution using a divalent cation, preferably zinc. In one embodiment, zinc chloride is added to the solution to a final concentration of from 1 mM to 15 mM. In a specific embodiment, zinc chloride is added to the solution to a final concentration of from 1 mM to 4 mM. In a more specific embodiment, zinc chloride is added to the solution to a final concentration of from 2.0 mM to 3.0 mM.

In certain embodiments, A1PI is further enriched according to purification methods known in the art, for example, those described in WO 1995/35306, WO 1998/00154, and U.S. Pat. Nos. 5,981,715; 7,807,435; and 7,879,800, the disclosures of which are hereby expressly incorporated by reference in their entireties for all purposes.

VI. Pharmaceutical Compositions

In one aspect, the present invention provides compositions of plasma-derived proteins which are prepared according to any of the methods described herein. In certain embodiments, these compositions will be formulated for pharmaceutical administration (i.e., pharmaceutical compositions).

In one embodiment, the present invention provides a plasma-derived protein composition prepared by a method comprising the steps of: co-precipitating immunoglobulins and alpha-1-antitrypsin (A1PI) from a Cohn pool, in a first precipitation step, to form a first precipitate and a first supernatant; suspending the first precipitate to form a first suspension; solubilizing immunoglobulins from the first suspension to form a soluble portion of the suspension comprising immunoglobulins and an insoluble portion of the suspension comprising A1PI, fibrinogen, Factor H, and IaIp; and separating the soluble portion of the suspension from the insoluble portion of the suspension. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

Generally, any chemical means for the precipitation of immunoglobulins and A1PI may be used, including but not limited to, alcohol precipitation (e.g., using ethanol or methanol), precipitation using water soluble polymers (e.g., PEG or dextran), and salting out (e.g., using ammonium phosphate, ammonium sulfate, sodium citrate, etc.). In a preferred embodiment, the precipitation is alcohol precipitation, preferably ethanol precipitation.

In one embodiment, the composition is formulated for pharmaceutical administration. In a specific embodiment, the composition is formulated for intravenous administration. In another specific embodiment, the composition is formulated for intramuscular administration. In another embodiment, the composition is formulated for subcutaneous administration. In yet another embodiment, the composition is formulated for intraocular administration.

In one embodiment, the pharmaceutical compositions provided herein are prepared by formulating a plasma-derived protein composition isolated using a method provided herein. Generally, the formulated composition will have been subjected to at least one, preferably at least two, most preferably at least three, viral inactivation or removal steps. Non-limiting examples of viral inactivation or removal steps that may be employed with the methods provided herein include, solvent detergent treatment (Horowitz et al., Blood Coagul fibrinogenolysis 1994 (5 Suppl 3):S21-S28 and Kreil et al., Transfusion 2003 (43): 1023-1028, both of which are herein expressly incorporated by reference in their entirety for all purposes), nanofiltration (Hamamoto et al., Vox Sang 1989 (56)230-236 and Yuasa et al., J Gen Virol. 1991 (72 (pt 8)):2021-2024, both of which are herein expressly incorporated by reference in their entirety for all purposes), and low pH incubation at high temperatures (Kempf et al., Transfusion 1991 (31)-423-427 and Louie et al., Biologicals 1994 (22):13-19). In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one embodiment, the pharmaceutical compositions provided herein will comprise one or more buffering agents or pH stabilizing agents suitable for intravenous, subcutaneous, intramuscular, and/or intraocular administration. Non-limiting examples of buffering agents suitable for formulating a plasma-derived protein composition provided herein include glycine, citrate, phosphate, acetate, glutamate, tartrate, benzoate, lactate, histidine or other amino acids, gluconate, malate, succinate, formate, propionate, carbonate, or any combination thereof adjusted to an appropriate pH. Generally, the buffering agent will be sufficient to maintain a suitable pH in the formulation for an extended period of time. In a preferred embodiment, the buffering agent is glycine. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In some embodiments, the pharmaceutical compositions provided herein may optionally further comprise an agent for adjusting the osmolarity of the composition. Non-limiting examples of osmolarity agents include mannitol, sorbitol, glycerol, sucrose, glucose, dextrose, levulose, fructose, lactose, polyethylene glycols, phosphates, sodium chloride, potassium chloride, calcium chloride, calcium gluconoglucoheptonate, dimethyl sulfone, and the like.

Typically, the formulations provided herein will have osmolarities that are comparable to physiologic osmolarity, about 285 to 295 mOsmol/kg (Lacy et al., Drug Information Handbook—Lexi-Comp 1999:1254. In certain embodiments, the osmolarity of the formulation will be between about 200 mOsmol/kg and about 350 mOsmol/kg, preferably between about 240 and about 300 mOsmol/kg. In particular embodiments, the osmolarity of the formulation will be about 200 mOsmol/kg, or 210 mOsmol/kg, 220 mOsmol/kg, 230 mOsmol/kg, 240 mOsmol/kg, 245 mOsmol/kg, 250 mOsmol/kg, 255 mOsmol/kg, 260 mOsmol/kg, 265 mOsmol/kg, 270 mOsmol/kg, 275 mOsmol/kg, 280 mOsmol/kg, 285 mOsmol/kg, 290 mOsmol/kg, 295 mOsmol/kg, 300 mOsmol/kg, 310 mOsmol/kg, 320 mOsmol/kg, 330 mOsmol/kg, 340 mOsmol/kg, 340 mOsmol/kg, or 350 mOsmol/kg.

The plasma-derived formulations provided herein are generally stable in liquid form for an extended period of time. In certain embodiments, the formulations are stable for at least about 3 months at room temperature, or at least about 4, 5, 6, 7, 8, 9, 10, 11, 12, 13, 14, 15, 16, 17, 18, 19, 20, 21, 22, 23, or 24 months at room temperature. The formulation will also generally be stable 6 or at least about 18 months under refrigerated conditions (typically between about 2° C. and about 8° C.), or for at least about 21, 24, 27, 30, 33, 36, 39, 42, or 45 months under refrigerated conditions.

VII. Method of Treatment

In one aspect, the present invention provides methods for treating a disease or disorder associated with a blood protein deficiency or dysfunction in a subject in need thereof by administering a therapeutically effective dose of a plasma-derived protein prepared according to a method provided herein. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one aspect, the present invention provides the use of a plasma-derived protein composition prepared according to a method provided herein for the manufacture of a medicament for use in the treatment of a condition associated with a blood protein deficiency or dysfunction. In certain embodiments, the plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

In one embodiment, the plasma-derived protein composition is prepared by a method comprising the steps of: co-precipitating immunoglobulins and alpha-1-antitrypsin (A1PI) from a Cohn pool, in a first precipitation step, to form a first precipitate and a first supernatant; suspending the first precipitate to form a first suspension; solubilizing immunoglobulins from the first suspension to form a soluble portion of the suspension comprising immunoglobulins and an insoluble portion of the suspension comprising A1PI, fibrinogen, Factor H, and IaIp; and separating the soluble portion of the suspension from the insoluble portion of the suspension. In certain embodiments, the composition comprises a plasma-derived protein is selected from an immunoglobulin (Ig), albumin, alpha-1-antitrypsin (A1PI), butyrylcholinesterase, Factor H, a protein of the complement system, and an inter-alpha-trypsin inhibitor (IαI) protein.

VIII. Examples

Example 1—NG2 C91

Immunoglobulin G (IgG) compositions are commercially manufactured by fractionating plasma through a series of precipitation reactions. In a common methodology, impurities are precipitated out of an immunoglobulin-containing cryo-poor plasma in a first alcohol precipitation step. IgG immunoglobulins are then precipitated from the resulting supernatant and subsequently further enriched. In an attempt to increase the yield of IgG recovered from human plasma during alcohol fractionation, pH values from 5.5 to 7.0 and ethanol concentrations from 20% to 25% were tested in IgG precipitation reactions.

Briefly, Fraction I supernatant, an intermediate used in the commercial manufacturing of plasma-derived Immunoglobulin G (IgG), alpha-1-antitrypsin (A1PI), and albumin products, was formed by admixing ethanol at a final concentration of 8% (v/v) to cryo-poor plasma at pH 7.2±0.2, incubating the mixture at 0° C., and separating the precipitate formed (Fraction I) from the supernatant (Fraction I supernatant). The resulting Fraction I supernatant was then aliquoted into 600 g samples. The pH of the individual samples were adjusted to from 5.5 to 7.0 and ethanol was admixed to a final concentration of from 20% to 25%, as shown in Table 9.

As reported in Table 9, conditions similar to those used to prepare a traditional Cohn Fraction II+III precipitate (25% ethanol; pH 6.8) and the modified Fraction II+III precipitate used in the manufacture of GAMMAGARD LIQUID® (Baxter International; Deerfield, Ill.) result in a loss of 2.9% and 6.7% of total IgG in the supernatant, due to incomplete precipitation. However, it was found that by reducing the pH of the reaction to 6.0 or lower and using a final ethanol concentration of at least 22.5%, IgG loss is significantly reduced. For example, the use of 22.5% alcohol at pH 5.5 resulted in the loss of only 0.4% of total IgG in the supernatant. Similarly, the use of 25% alcohol at pH 6.0 or 5.5 resulted in the loss of only 0.5% and 0.1% of total IgG in the supernatant. As reported in Table 10, this equates to an increase of more than 300 mg IgG/L plasma and 125 mg IgG/L plasma in the precipitate as compared to the traditional and modified Fraction II+III precipitates, respectively.

TABLE 9

Yield of proteins in precipitation supernatant, expressed as a percent of the protein content of the starting material (Fraction I supernatant).

| EtOH (%) | pH | protein biuret | IgG ELISA | IgA ELISA | IgM ELISA | fibrinogen ELISA | transferrin ELISA | a1-antitrypsin ELISA | albumin neph |
|---|---|---|---|---|---|---|---|---|---|
| 20 | 5.5 | 60.8 | 1.1 | 3.5 | 0.2 | 0.2 | 73.9 | 6.1 | 93.1 |
| 20 | 6 | 68.0 | 2.9 | 12.8 | 0.5 | 0.2 | 94.3 | 38.9 | 92.4 |
| 20 | 6.5 | 70.0 | 4.1 | 20.6 | 1.0 | 0.7 | 100.2 | 63.2 | 97.4 |
| 20 | 7 | 73.0 | 6.7 | 45.8 | 1.9 | 4.6 | 98.4 | 76.9 | 96.5 |
| 22.5 | 5.5 | 56.7 | 0.4 | 1.2 | 0.1 | 0.2 | 47.5 | 1.1 | 90.6 |
| 22.5 | 6 | 64.6 | 1.1 | 4.8 | 0.4 | 0.4 | 78.2 | 21.7 | 98.0 |
| 22.5 | 6.5 | 68.0 | 1.8 | 9.0 | 0.6 | 0.4 | 85.9 | 27.3 | 96.6 |
| 22.5 | 7 | 70.3 | 3.0 | 19.4 | 1.2 | 0.9 | 97.3 | 27.1 | 96.5 |
| 25 | 5.5 | 45.6 | 0.1 | 0.6 | 0.0 | 0.2 | 8.6 | 0.8 | 76.8 |
| 25 | 6 | 60.2 | 0.5 | 1.4 | 0.3 | 0.3 | 59.2 | 7.6 | 92.9 |
| 25 | 6.5 | 66.9 | 2.2 | 5.7 | 1.6 | 1.7 | 86.0 | 18.3 | 95.6 |
| 25 | 7 | 67.8 | 2.9 | 8.5 | 2.3 | 1.7 | 95.1 | 18.9 | 96.5 |

TABLE 10

Yield of proteins in precipitation supernatant, expressed as g/L plasma.

| EtOH (%) | pH | protein biuret | IgG ELISA | IgA ELISA | IgM ELISA | fibrinogen ELISA | transferrin ELISA | a1-antitrypsin ELISA | albumin neph |
|---|---|---|---|---|---|---|---|---|---|
| 20 | 5.5 | 26.457 | 0.061 | 0.045 | 0.001 | 0.000 | 1.327 | 0.071 | 29.402 |
| 20 | 6 | 29.603 | 0.157 | 0.162 | 0.002 | 0.001 | 1.692 | 0.459 | 29.174 |
| 20 | 6.5 | 30.445 | 0.223 | 0.261 | 0.004 | 0.002 | 1.799 | 0.745 | 30.737 |
| 20 | 7 | 31.792 | 0.368 | 0.579 | 0.008 | 0.012 | 1.765 | 0.907 | 30.460 |
| 22.5 | 5.5 | 24.673 | 0.021 | 0.015 | 0.000 | 0.000 | 0.852 | 0.013 | 28.591 |

TABLE 10-continued

Yield of proteins in precipitation supernatant, expressed as g/L plasma.

| EtOH (%) | pH | protein biuret | IgG ELISA | IgA ELISA | IgM ELISA | fibrinogen ELISA | transferrin ELISA | a1-antitrypsin ELISA | albumin neph |
|---|---|---|---|---|---|---|---|---|---|
| 22.5 | 6 | 28.095 | 0.062 | 0.061 | 0.002 | 0.001 | 1.403 | 0.255 | 30.946 |
| 22.5 | 6.5 | 29.577 | 0.097 | 0.114 | 0.002 | 0.001 | 1.542 | 0.322 | 30.488 |
| 22.5 | 7 | 30.609 | 0.165 | 0.246 | 0.005 | 0.001 | 1.747 | 0.320 | 30.455 |
| 25 | 5.5 | 19.833 | 0.004 | 0.007 | 0.000 | 0.000 | 0.155 | 0.009 | 24.263 |
| 25 | 6 | 26.212 | 0.025 | 0.018 | 0.001 | 0.001 | 1.062 | 0.089 | 29.325 |
| 25 | 6.5 | 29.097 | 0.119 | 0.072 | 0.006 | 0.004 | 1.795 | 0.215 | 30.198 |
| 25 | 7 | 29.512 | 0.157 | 0.107 | 0.009 | 0.004 | 1.706 | 0.223 | 30.458 |

Example 2—NG2 C96

An experimental comparison of IgG purification schemes performed with and without an initial 8% ethanol precipitation was undertaken to determine if further increases in the recovery of IgG could be obtained using a low pH (5.5), high ethanol (25%) precipitation, as outlined in Example 1.

Briefly, 100 kg of cryo-poor plasma was processed with (NG2C96/1) or without (NG2C96/2) an initial precipitation step (Fraction I) performed using 8% (v/v) final concentration ethanol at pH 7.4 and 0° C. The pH of the cryo-poor plasma (NG2C96/1) or Fraction I supernatant (NG2C96/2) was adjusted to pH 5.5±0.1 and ethanol was admixed to a final concentration of 25% (v/v). The mixtures where then incubated at −5±2° C. for 5 hours to allow for protein precipitation. The resulting precipitates (precipitate (I)+II+III) and supernatants (supernatant (I)+II+III) were separated by centrifugation. Due to the size of the precipitation reactions, two centrifugations were required for each reaction. The resulting precipitates from each centrifugation were processed separately.

The precipitates were suspended in buffer containing 5 mM monosodium phosphate, 5 mM sodium acetate, and 600 mg/L glacial acetic acid at a ratio of 1 part precipitate per 15 parts buffer, the pH was adjusted to 4.8±0.2, and stirred to extract proteins for 2 hours at between 4° C. and 8° C. After the extraction incubation, 40 g of fumed silica (SiO$_2$)/kg precipitate (I)+II+III was admixed into the reactions and stirred for 50 minutes at between 4° C. and 8° C. 400 g Cellpure filter aid/kg precipitate (I)+II+III was then admixed and the reactions were filtered through Cuno 50SA membranes to remove insoluble material, forming a (I)+II+III filtrate and a filtercake. The filtercake was washed with buffer containing 5 mM monosodium phosphate, 5 mM sodium acetate, and 150 mg/L glacial acetic acid, the filtrate of which was added to the (I)+II+III filtrate.

Polysorbate 80 was added to the filtrates to a final concentration of 0.2% (w/w) and the solutions were incubated for 30 minutes. Sodium citrate dihydrate was then added to the solutions to a final concentration of 0.8% (w/w) and the solution was incubated for an additional minutes. After the second incubation, the pH of the solution was adjusted to 7.0 using sodium hydroxide and ethanol was admixed to a final concentration of 25%. The temperature was lowered to between 0° C. and −10° C. to allow for precipitation. The precipitate (PptG) and supernatant (PptG supernatant) were separated by centrifugation.

The IgG, IgA, and IgM immunoglobulin contents of each sub-step of the purification reactions were determined. As shown in Table 11, removal of the initial Fraction I precipitation step resulted in a significantly greater yield of IgG in the final composition (compare PptG dissolved NG2C96/2 (without Fraction I precipitation) to NG2C96/1 (with Fraction I precipitation). Likewise, the IgA (Table 12) and IgM (Table 13) content of the dissolved PptG fraction formed without the initial Fraction I precipitation step.

Notably, the Fraction I precipitation step is used in part to remove fibrinogen from immunoglobulin-containing compositions. Although the final fibrinogen content of the dissolved PptG fraction formed without the initial Fraction I precipitation step is roughly 6 times greater than the content of the PptG fraction formed with the initial Fraction I precipitation step, the fractionation scheme removes greater than 99% of the fibrinogen content present in the cryo-poor plasma starting material (Table 14).

TABLE 11

IgG content, expressed as g/L starting plasma, of the various fractions formed during fractionation of plasma using a low pH, high alcohol precipitation reaction with and without an initial 8% ethanol Fraction I precipitation step.

| | IgG g/L Plasma | | | |
|---|---|---|---|---|
| | NG2C96/1 precipitation II + III | NG2C96/1 B | NG2C96/2 precipitation I + II + III | NG2C96/2 B |
| plasma | 5.36 | | 5.36 | |
| supernatant I | 5.32 | | — | |
| Ppt I dissolved supernatant | 0.11 | | — | |
| supernatant (I) + II + III | 0.004 | | 0.007 | |
| (I) + II + III suspension | 4.37 | 4.72 | 5.07 | 4.40 |
| (I) + II + III filtrate | 4.55 | 5.33 | 5.36 | 4.77 |
| filtercake dissolved supernatant | 0.10 | 0.18 | 0.08 | 0.10 |
| PptG supernatant | 0.08 | 0.06 | 0.09 | 0.05 |
| PptG dissolved | 4.03 | — | 5.03 | — |

TABLE 12

IgA content, expressed as g/L starting plasma, of the various fractions formed during fractionation of plasma using a low pH, high alcohol precipitation reaction with and without an initial 8% ethanol Fraction I precipitation step.

| | IgA g/L Plasma | | | |
|---|---|---|---|---|
| | NG2C96/1 precipitation II + III | NG2C96/1 B | NG2C96/2 precipitation I + II + III | NG2C96/2 B |
| plasma | 1.20 | | 1.20 | |
| supernatant I | 1.14 | | — | |
| Ppt I dissolved supernatant | — | | — | |
| supernatant (I) + II + III | 0.001 | | 0.002 | |

TABLE 12-continued

IgA content, expressed as g/L starting plasma, of the various fractions formed during fractionation of plasma using a low pH, high alcohol precipitation reaction with and without an initial 8% ethanol Fraction I precipitation step.

| | IgA g/L Plasma | | | |
|---|---|---|---|---|
| | NG2C96/1 precipitation II + III | NG2C96/1 B | NG2C96/2 precipitation I + II + III | NG2C96/2 B |
| (I) + II + III suspension | 0.92 | 1.37 | 1.08 | 1.21 |
| (I) + II + III filtrate | 0.80 | 1.02 | 1.01 | 0.96 |
| filtercake dissolved supernatant | — | — | — | — |
| PptG supernatant | — | — | — | — |
| PptG dissolved | 0.66 | — | 0.79 | — |

TABLE 13

IgM content, expressed as g/L starting plasma, of the various fractions formed during fractionation of plasma using a low pH, high alcohol precipitation reaction with and without an initial 8% ethanol Fraction I precipitation step.

| | IgM g/L Plasma | | | |
|---|---|---|---|---|
| | NG2C96/1 precipitation II + III | NG2C96/1 B | NG2C96/2 precipitation I + II + III | NG2C96/2 B |
| plasma | 0.41 | | 0.41 | |
| supernatant I | 0.39 | | — | |
| Ppt I dissolved supernatant | — | | — | |
| supernatant (I) + II + III | 0.0001 | | 0.0004 | |
| (I) + II + III suspension | 0.38 | 0.45 | 0.40 | 0.41 |
| (I) + II + III filtrate | 0.22 | 0.24 | 0.29 | 0.28 |
| filtercake dissolved supernatant | — | — | — | — |
| PptG supernatant | — | — | — | — |
| PptG dissolved | 0.19 | — | 0.29 | — |

TABLE 14 fibrinogen content, expressed as g/L starting plasma, of the various fractions formed during fractionation of plasma using a low pH, high alcohol precipitation reaction with and without an initial 8% ethanol Fraction I precipitation step.

| | Fibrinogen g/L Plasma | | | |
|---|---|---|---|---|
| | NG2C96/1 precipitation II + III | NG2C96/1 B | NG2C96/2 precipitation I + II + III | NG2C96/2 B |
| plasma | 1.45 | | 1.45 | |
| supernatant I | 0.28 | | — | |
| Ppt I dissolved supernatant | — | | — | |
| supernatant (I) + II + III | 0.0001 | | 0.0004 | |
| (I) + II + III suspension | 0.25 | 0.34 | 1.27 | 1.34 |
| (I) + II + III filtrate | 0.002 | 0.005 | 0.017 | 0.018 |
| filtercake dissolved supernatant | — | — | — | — |
| PptG supernatant | — | — | — | — |
| PptG dissolved | 0.0021 | — | 0.013 | — |

Example 3—NG2 C99

To further explore the use of a low pH, high alcohol precipitation in place of traditional upstream Cohn-Oncley and Kistler-Nitschmann alcohol fraction steps (i.e., Cohn Fraction I and II; Cohn Fraction I and II+III; or Kistler Nitschmann 8-10% ethanol, precipitate A, and precipitate B), the NG2C96/2 and NG2C96/2B PptG precipitates were combined and further enriched for IgG immunoglobulins.

Briefly, the combined NG2C96/2 and NG2C96/2B PptG precipitates were suspended in water for injection (WFI) adjusted to pH 4.75±0.75 with acetic acid and a conductivity of 4.5±1.5 mS/cm with sodium chloride. Filter aid was added and the suspension was filtered through Cuno VR06 membranes to form a clarified PptG filtrate (VR06). The clarified filtrate was then treated with solvents and detergents (S/D treatment) according to standard procedures.

The S/D treated filtrate was loaded onto a CM sepharose column equilibrated with buffer containing 10 mM sodium acetate (pH 5.0) and the flow through (CM D/N) was collected. The column was then washed with buffer containing 10 mM sodium acetate (pH 5.5) and the wash (CM W) was collected. The immunoglobulins were eluted off of the column using an elution buffer containing 55 mM monosodium phosphate and 10 mM TRIS (pH 8.5). The eluate was collected in three fractions: Fraction 1 (CM E-VL) including the first portion of the eluate having an $OD_{280}$ of less than 100 mAU; Fraction 2 (CM E) including the peak of the eluate having an $OD_{280}$ of greater than 100 mAU on the leading edge of the elution peak and an OD280 of greater than 400 mAU on the lagging edge of the elution peak; and Fraction 3 (CM E-NL) including the portion of the eluate on the lagging side of the peak having an OD280 of less than 400 mAU.

The pH and conductivity of the Fraction 2 eluate was adjusted to 6.4 and 2.3 mS/cm using glacial acetic acid and water for injection (WFI), respectively. The Fraction 2 eluate was then loaded onto an ANX Sepharose fast flow anion exchange resin equilibrated with buffer containing 15 mM monosodium phosphate (pH 6.4) at a load concentration of 100 mg protein/mL resin. The anion exchange flow through, containing the majority of the IgG was collected (ANX D/N). Protein binding to the anion exchange resin was eluted off the column using a solution containing 2 M sodium chloride (ANX 2M NaCl).

Glycine was added to the anion exchange flow through fraction and the sample was ultra- and diafiltered (UF/DF) using a Pellicon® 2 Mini (Millipore) against solution containing 0.25 M glycine (pH 5.2) until a protein concentration of 5% was achieved. The immunoglobulin solution was further concentrated to a final protein concentration of 10% and the pH was adjusted to 4.5 (dia-concentrate). The 10% immunoglobulin solution was then sterile filtered using a Millipak 20 (Millipore) to form the final immunoglobulin composition (final container).

The biochemical profile for each sub-step of the purification reaction was determined (Table 15 and Table 16). As shown in the data, the final composition contained only low levels of non-IgG proteins, within acceptable parameters for pharmaceutical administration.

TABLE 15

Biochemical characterization of the various fractions formed during fractionation of plasma using a low pH, high alcohol precipitation reaction without an initial 8% ethanol Fraction I precipitation step.

| | Protein g/L Cohn Pool | | IgG | IgA | IgM | α1 Antitrypsin |
|---|---|---|---|---|---|---|
| | Biuret | UV | g/L Cohn Pool | g/L Cohn Pool | g/L Cohn Pool | g/L Cohn Pool |
| Cohn pool | 47.38 | | 5.36 | 1.20 | 0.41 | 1.01 |
| supernatant I + II + III | 19.79 | | <0.0073 | 0.002 | 0.0004 | 0.004 |
| I + II + III suspension | 25.83 | | 4.62 | 1.17 | 0.41 | 0.33 |
| I + II + III filtrate | 18.24 | | 4.97 | 0.98 | 0.28 | |
| filtercake dissolved supernatant | 4.52 | | 0.09 | | | 0.61 |
| PptG supernatant | 11.00 | | 0.06 | | | |
| PptG dissolved | 7.46 | | 5.46 | 1.01 | 0.32 | 0.01 |
| VR 06 | 7.47 | | 5.20 | 0.95 | 0.31 | |
| VR 06 diluted | 7.23 | | 5.20 | 0.99 | 0.31 | |
| CM D/N | 0.66 | | <0.04/0.026 | | | |
| CM W | 0.11 | 0.09 | <0.13/0.0066 | | | |
| CM E-VL | 0.001 | 0.001 | <0.0031/<0.00001 | | | |
| CM E | 6.16 | 5.38 | 4.85 | 0.60 | 0.042 | |
| CM E-NL | 0.08 | 0.04 | 0.011/0.014 | | | |
| CM 2M NaCl | 0.19 | 0.11 | 0.05/0.04 | 0.014 | 0.02 | |
| CM E diluted | | 5.33 | 4.61 | | | |
| ANX D/N | | 4.45 | 4.52 | 0.0014 | 0.00007 | |
| ANX 2M NaCl | 1.34 | | 0.40/0.28 | 0.59 | 0.044 | |
| dia-concentrate | | 4.16 | 2.55 | | | |
| post wash 1 | | 0.59 | | | | |
| post wash 2 | | 0.05 | | | | |
| post wash 3 | | 0.01 | | | | |
| dia-concentrate diluted | | 3.81 | | | | |
| final container | | 3.86 | 3.94 | 0.0012 | 0.00004 | |

TABLE 16

Further biochemical characterization of the various fractions formed during fractionation of plasma using a low pH, high alcohol precipitation reaction without an initial 8% ethanol Fraction I precipitation step.

| | α2 Macroglobulin g/L Cohn Pool | Fibrinogen g/L Cohn Pool | Transferrin g/L Cohn Pool | Albumin g/L Cohn Pool | Complement C3 g/L Cohn Pool |
|---|---|---|---|---|---|
| Cohn pool | | 1.45 | 2.17 | | 0.80 |
| supernatant (I) + II + III | | 0.0004 | 2.44 | | <0.001 |
| (I) + II + III suspension | | 1.32 | 1.99 | 6.40 | 0.55 |
| (I) + II + III filtrate | | 0.02 | 1.95 | 6.82 | 0.05 |
| filtercake dissolved supernatant | | | | | |
| PptG supernatant | | | | | |
| PptG dissolved | 0.46 | 0.02 | 0.02 | | 0.04 |
| VR 06 | | 0.01 | 0.02 | | 0.03 |
| VR 06 diluted | | | | | |
| CM D/N | 0.17 | | | | |
| CM W | | | | | |
| CM E-VL | | | | | |
| CM E | 0.22 | 0.011 | 0.024 | | 0.020 |
| CM E-NL | | | | | |
| CM 2M NaCl | | | | | |
| CM E diluted | | | | | |
| ANX D/N | <0.00002 | <0.00006 | 0.003 | | <0.00004 |
| ANX 2M NaCl | | | | | |
| dia-concentrate | | | | | |
| post wash 1 | | | | | |
| post wash 2 | | | | | |
| post wash 3 | | | | | |
| dia-concentrate diluted | | | | | |
| final container | 0.000001 | 0.00001 | 0.0028 | | 0.00003 |

Example 4—NG2 C100

To validate the use of a low pH, high alcohol precipitation without an initial low alcohol precipitation step to remove fibrinogen, 200 kg of cryo-poor plasma was fractionated and enriched as described for sample NG2C96/2 in Examples 2 and 3, with a couple of alterations to the process. First, the low pH, high alcohol precipitation step (I-IV1 precipitation) was performed using 25% ethanol at pH 5.1, rather than 5.5. Secondly, the suspended I-IV1 precipitate was treated with 33 g of fumed silica ($SiO_2$)/kg precipitate I-IV1, rather than 40 g $SiO_2$/kg precipitate. Thirdly, the CM cation exchange eluate was loaded onto the ANX anion exchange resin at a concentration of 150 mg protein/mL ANX resin, rather than 100 mg/mL ANX resin. Finally, the Cuno VR06 filtered anion exchange flow through was passed through a PLANOVA®35N (Asahi Kasei Medical Co., Ltd.; Tokyo, Japan) to perform a nanofiltration step prior to ultra-/diafiltration.

The IgG content of each step of the purification was determined and the results are provided in Table 17. As compared to the average IgG yield for the GAMMAGARD LIQUID® manufacturing process (3.7 g IgG/L source plasma), the purification method used in this example results in a significantly higher yield of 4.4 g IgG/L source plasma. This represents almost a 20% increase in the IgG yield. Biochemical characterization of the final IgG composition is reported in Table 10. As seen in the table, the final IgG composition has greater than 99% purity and the IgG monomer/dimer content is greater than 99.8%. The final container contains only traces of impurities, the levels of which are within regulatory standards.

TABLE 17

IgG content of the fractions formed during enrichment from cryo-poor plasma using an initial low pH, high alcohol precipitation step.

| | | IgG | | | | |
|---|---|---|---|---|---|---|
| | | mg/ml | g | % | purity (%) | g/l plasma |
| I-IV-1 precipitation | Cohn pool | 5.52 | 1113.94 | 100.00 | 11.43 | 5.52 |
| | I-IV1 prior EtOH addition | | | | | |
| | I-IV1 after EtOH addition | | | | | |
| | I-IV1 supernatant | <0.00121 | <0.029 | <0.026 | <0.013 | <0.0014 |
| | I-IV1 supernatant centrifuge 1 | <0.00121 | <0.029 | <0.026 | <0.013 | <0.0014 |
| | I-IV1 supernatant centrifuge 2 | <0.00121 | <0.029 | <0.026 | <0.013 | <0.0014 |
| | I-IV1 precipitate | | | | | |
| I-IV1 extraction a. filtration filter cake | I-IV1 precipitate used | | | | | |
| | I-IV1 suspension | 2.69 | 975.30 | 87.55 | 13.43 | 4.83 |
| | CUNO filtrate | 1.69 | 1186.24 | 106.49 | 21.41 | 5.88 |
| | REZ 1 | 0.09 | 18.23 | 1.64 | 1.78 | 0.090 |
| | REZ 2 | 0.02 | 2.31 | 0.21 | 1.04 | 0.011 |
| PptG-precipitation | PptG precipitation | | | | | |
| | PptG supernatant | 0.02 | 14.02 | 1.26 | 0.35 | 0.069 |
| | PptG used | | | | | |
| PptG extraction, clarification. SD and CM sepharose ff | PptG suspension | 47.4 | 1152.39 | 103.45 | 69.55 | 5.71 |
| | VR06 (PptG) | 22.8 | 1074.82 | 96.49 | 66.31 | 5.33 |
| | VR06 diluted | 13.80 | 1126.98 | 101.17 | 80.00 | 5.58 |
| | SD | | | | | |
| | Load CM | | | | | |
| | D/N | 0.140 | 18.38 | 1.65 | 7.93 | 0.091 |
| | D/N | 0.228 | 29.84 | 2.68 | 12.88 | 0.15 |
| | W | 0.005 | 1.96 | 0.18 | 16.45 | 0.010 |
| | W | <0.068 | <27.91 | <2.51 | <234.48 | <0.14 |
| | E-VL | <0.0712 | <0.59 | <0.05 | <334.63 | <0.00 |
| | E | 23.2 | 1026.43 | 92.14 | 86.02 | 5.09 |
| | E-NL | 0.661 | 4.55 | 0.41 | 89.26 | 0.023 |
| | 2M NaCl | 0.114 | 5.82 | 0.52 | 43.92 | 0.029 |
| | 2M NaCl | 0.139 | 7.08 | 0.64 | 53.46 | 0.035 |
| ANX SEPH 4FF low sub | E diluted | 9.005 | 1113.29 | 99.94 | 92.64 | 5.52 |
| | Load ANX | | | | | |
| | D/N | 6.35 | 903.11 | 81.07 | 94.49 | 4.48 |
| | 2M NaCl | 3 | 78.99 | 7.09 | 26.31 | 0.39 |
| VR06 | VR06 (ANX) | 6.185 | 972.42 | 87.30 | 101.23 | 4.82 |
| Asahi | ASAHI filtrate | 5.27 | 907.55 | 81.47 | 94.95 | 4.50 |
| UF/DF | Diaconcentrate | 102.5 | 910.38 | 81.73 | 100.89 | 4.51 |
| | post wash 1 | 8.255 | 51.70 | 4.64 | 102.78 | 0.26 |
| | post wash 2 | | | | | |
| | post wash 3 | | | | | |
| | Diaconcentrate (final) | 96.1 | 871.30 | 78.22 | 96.56 | 4.32 |
| FC | final container (calculated) | 100 | 888.18 | 79.73 | | 4.40 |

TABLE 18

Biochemical characterization of the final IgG composition enriched from 200 L of cryo-poor plasma using an initial low pH, high alcohol precipitation step.

| Test | Unit | Result |
|---|---|---|
| Total Protein - Kjeldahl | mg/ml | 109.8 |
| Total Protein - Kjeldahl | mg/ml | 108.5213 |
| Purity (CAE) | Albumin % | 0 |
|  | α/β globulin % | 0 |
|  | γ-globulin % | 100 |
|  | denat. Protein % | 0 |
| Molecular size distribution | Monomer [%] | 93.2085 |
|  | Dimer [%] | 6.6806 |
|  | Polymer [%] | 0.0828 |
|  | Fragments [%] | 0.0281 |
| IgG neph | mg/ml | 100 |
| IgA (ELISA) | mg/ml | 0.03 |
| IgM (ELISA) | mg/dl | 0 |
| IgE (ELISA) | IU/ml | 66.2 |
| Albumin (ELISA) | mg/ml | 0.00184 |
| Fibrinogen (ELISA) | µg/ml | <0.17 |
| Plasminogen (ELISA) | µg/ml | 0.26 |
| C3 complement | mg/dl | <19.4 |

| Test | Subclass group | Result (mg/ml) |
|---|---|---|
| IgG-subclass distribution | IgG1 | 54.7158 |
|  | IgG2 | 29.22 |
|  | IgG3 | 7.2029 |
|  | IgG4 | 2.3634 |

| Test | Unit | Result |
|---|---|---|
| IgG Fc Function (FACS) |  | 108 ± 15 |
| IgG Fc Function HemaggL | % | 103 |
| Protein identity |  | positive |
| Amidolytic activity (PL-1) | nmol/ml | 87.3 |
| Anticomple. Activity | % | 42 |
| PKA | % of ref lot 3 | 1.59 |
| PKA | IU/ml | 1.2 |
| NAPPT | mg | 0.773 |
| Factor XIa | mU/ml | 24.9 |
|  | pM | 771.6 |
| Appearance |  | satisfactory |
| ph |  | 5.643 |
| Silicon | µg/l | 664 |
| Aluminum | µg/l | <25 |
| Glycine | M | 0.074 |
| Osmolality | mosmol/kg | 90 |
| Pyrogen | EU/US | sat./sat. |
| Density | g/cm³ | 1.0301 |
| SD Reagents |  |  |
| Octoxynol 9 (Triton X100) | ppm | 0.50 |
| Polysorbate 80 | ppm | <26 |
| Tri(n-butyl)phosphate | ppm | <0.2 |

TABLE 18-continued

Biochemical characterization of the final IgG composition enriched from 200 L of cryo-poor plasma using an initial low pH, high alcohol precipitation step.

| Antibodies | | |
|---|---|---|
| Diphtheria | IU/mL | 8.0 |
| Diphtheria | IU/mL | 9 |
| Measles | IU/mL | 39.63 |
| HBs antigen (ELISA) |  | negative |
| HBs (ELISA) | mIU/mL | 5775 |
| Poliomyelitis | Quotient gg 176 | 0.90 |
| HAV (ELISA) | IU/mL | 13.8 |
| Parvo B19 (ELISA) | IU/mL | 426 |
| Haemophilus Influenzae | Titer | 1:6400 |
| Anti D Antibodies |  | satisfactory |
| Anti A&AntiB Hemagglutinins | Anti A | 16 |
|  | Anti B | 8 |

Example 5—P02910NG2

To compare the effect of passing the CM cation exchange eluate over an ANX anion exchange column at loading concentrations of 100 g protein/mL ANX resin and 150 g protein/mL ANX resin, 200 L of cryo-poor plasma was fractionated via an initial low pH (5.4), high alcohol (25%) precipitation step and processed to form a PptG precipitate as described for sample NG2C96/2 in Examples 2 and 3. The IgG, IgA, and IgM contents of the upstream fractions formed were determined and are reported in Table 19, Table 20, and Table 21, respectively.

The resulting PptG precipitate was divided into two 1.8 kg samples, which were enriched to the final container as described for sample NG2C96/2 in Examples 2 and 3, except that one sample was passed over the ANX anion exchange resin at a loading concentration of 100 mg protein/mL ANX resin (P03010NG2) and the other was passed over the ANX anion exchange resin at a loading concentration of 150 mg protein/mL ANX resin (P03110NG2).

The IgG content of each downstream enrichment step of the purifications was determined and the results are provided in Table 22 and Table 23. As compared to the average IgG yield for the GAMMAGARD LIQUID® manufacturing process (3.7 g IgG/L source plasma), the purification methods used in this example results in significantly higher yields of 4.3 g IgG/L source plasma. This represents a 16% increase in the IgG yield. Biochemical characterizations of the final IgG compositions are reported in Table 16 and Table 17. As seen in the tables, the final IgG compositions have greater than 99% purity and the IgG monomer/dimer contents are greater than 99.8%. The final container contains only traces of impurities, the levels of which are within regulatory standards.

TABLE 19

IgG content of the upstream fractions formed during fractionation of plasma using an initial low pH (5.4), high alcohol (25% ethanol) precipitation reaction.

|  |  | weight | weight calc. | IgG nephelometry IPC/ELISA | | | |
|---|---|---|---|---|---|---|---|
|  |  | kg | kg | mg/ml | g | % | purity (%) | g/l plasma |
|  | Cohn Pool | 204.60 | 204.60 | 5.26 | 1076.20 | 100.00 | 10.72 | 5.26 |
| I-IV-1 precipitation | I-IV1 prior EtOH addition | 206.46 | 206.81 |  |  |  |  |  |
|  | I-IV1 after EtOH addition | 266.56 | 267.14 |  |  |  |  |  |
|  | I-IV1 supernatant | 247.80 | 248.64 | 0.00517 | 1.29 | 0.12 | 0.03 | 0.01 |
|  | I-IV1 precipitate | 17.10 | 17.16 |  |  |  |  |  |

TABLE 19-continued

IgG content of the upstream fractions formed during fractionation of plasma using an initial low pH (5.4), high alcohol (25% ethanol) precipitation reaction.

| | | weight kg | weight calc. kg | IgG nephelometry IPC/ELISA | | | | |
|---|---|---|---|---|---|---|---|---|
| | | | | mg/ml | g | % | purity (%) | g/l plasma |
| I-IV1 | I-IV1 precipitate used | 11.21 | 17.16 | | | | | |
| extraction a. | I-IV1 suspension | 180.21 | 275.80 | 4.09 | 1128.02 | 104.82 | 23.15 | 5.51 |
| filtration | CUNO filtrate | 340.70 | 522.00 | 2.11 | 1101.42 | 102.34 | 34.72 | 5.38 |
| PptG- | PptG precipitation | 2.59 | 3.96 | | | | | |
| precipitation | PptG supernatant | 442.20 | 677.32 | 0.0235 ELISA | 15.92 | 1.48 | 0.93 | 0.08 |

TABLE 20

IgA content of the upstream fractions formed during fractionation of plasma using an initial low pH (5.4), high alcohol (25% ethanol) precipitation reaction.

| | | weight kg | weight calc. kg | IgA ELISA | | | | |
|---|---|---|---|---|---|---|---|---|
| | | | | mg/ml | g | % | purity (%) | g/l plasma |
| | Cohn Pool | 204.60 | 204.60 | 1.18 | 241.43 | 100.00 | 2.41 | 1.18 |
| I-IV1- | I-IV1 prior EtOH addition | 206.46 | 206.81 | | | | | |
| precipitation | I-IV1 after EtOH addition | 266.56 | 267.14 | | | | | |
| | I-IV1 supernatant | 247.80 | 248.64 | 0.00251 | 0.62 | 0.26 | 0.01 | 0.0031 |
| | I-IV1 precipitate | 17.10 | 17.16 | | | | | |
| I-IV1 | I-IV1 precipitate used | 11.21 | 17.16 | | | | | |
| extraction a. | I-IV1 suspension | 180.21 | 275.80 | 0.861 | 237.46 | 98.36 | 4.87 | 1.16 |
| filtration | CUNO filtrate | 340.70 | 522.00 | 0.365 | 190.53 | 78.92 | 6.01 | 0.93 |
| PptG- | PptG precipitation | 2.59 | 3.96 | | | | | |
| precipitation | PptG supernatant | 442.20 | 677.32 | | | | | |

TABLE 21

IgM content of the upstream fractions formed during fractionation of plasma using an initial low pH (5.4), high alcohol (25% ethanol) precipitation reaction.

| | | weight kg | weight calc. kg | IgM ELISA | | | | |
|---|---|---|---|---|---|---|---|---|
| | | | | mg/ml | g | % | purity (%) | g/l plasma |
| | Cohn Pool | 204.60 | 204.60 | 0.451 | 92.27 | 100.00 | 0.92 | 0.45 |
| I-IV1- | I-IV1 prior EtOH addition | 206.46 | 206.81 | | | | | |
| precipitation | I-IV1 after EtOH addition | 266.56 | 267.14 | | | | | |
| | I-IV1 supernatant | 247.80 | 248.64 | 0.00021 | 0.052 | 0.0566 | <0.0011 | <0.00026 |
| | I-IV1 precipitate | 17.10 | 17.16 | | | | | |
| I-IV1 | I-IV1 precipitate used | 11.21 | 17.16 | | | | | |
| extraction a. | I-IV1 suspension | 180.21 | 275.80 | 0.353 | 97.36 | 105.51 | 2.00 | 0.48 |
| filtration | CUNO filtrate | 340.70 | 522.00 | 0.110 | 57.42 | 62.23 | 1.81 | 0.28 |
| PptG- | PptG precipitation | 2.59 | 3.96 | | | | | |
| precipitation | PptG supernatant | 442.20 | 677.32 | | | | | |

TABLE 22

IgG content of the downstream fractions formed during fractionation of plasma using an initial low pH (5.4), high alcohol (25% ethanol) precipitation reaction, and an ANX anion exchange loading concentration of 100 mg/mL ANX resin (P03010NG2).

| Sample | | Weight (kg) | Corr. Weight (kg) corr. | Protein (g) | IgG mg/ml | g | Yield (%) | Purity(%) | g/l Plasma | Step Yield % |
|---|---|---|---|---|---|---|---|---|---|---|
| PptG Suspension and Filtration | | | | | | | | | | |
| PptG Susp. | 10/2 | 8.36 | 8.36 | 644.59 | 55.7 | 465.47 | 100 | 72.2 | 4.99 | |
| PptG Filtrat. | 10/6 | 15.91 | 16.24 | 669.20 | 30 | 487.34 | 104.70 | 72.8 | 5.22 | |
| PptG Filtrat verd. | 10/7 | 32.50 | 33.43 | 658.56 | 13.7 | 458.05 | 98.41 | 69.6 | 4.91 | 100.00 |
| CM Sepharose | | | | | | | | | | |
| D | 12/12 A | 38.00 | 53.88 | 48.9 | 0.0937 | 5.048 | 1.085 | 10.325 | 0.054 | 1.10 |
| W | 12/12 B | 127.60 | 180.91 | 0.54 | <0.0712 | | | | | 0.00 |
| VL | 12/12 C | 2.41 | 3.41 | 0.04 | <0.0712 | | | | | 0.00 |
| Eluate | 12/12 D | 13.40 | 19.00 | 580.49 | 23.8 | 452.17 | 97.14 | 77.9 | 4.85 | 98.72 |
| NL | 12/12 E | 1.18 | 1.67 | 2.18 | 0.642 | 1.073 | 0.23 | 49.1 | 0.012 | 0.23 |
| 2M NaCl | 12/12 F | 15.01 | 21.28 | 9.69 | 0.163 | 3.47 | 0.75 | 35.8 | 0.037 | 0.76 |
| Sum | | | | | | | 99.20 | | 4.95 | 100.81 |
| Diluted Eluate | 12/13 | 4.3377 | 37.49 | 599.85 | 10.7 | 401.16 | 86.18 | 66.9 | 4.30 | 100.00 |
| ANX-Sepharose | | | | | | | | | | |
| D/N | 13/6 A | 7.83 | 53.94 | 419.63 | 8.27 | 446.05 | 95.83 | 106.3 | 4.78 | 111.19 |
| 2M NaCl | 13/6 B | 2.34 | 16.12 | 144.67 | 2.38 | 38.37 | 8.24 | 26.5 | 0.41 | 9.56 |
| Sum | | | | | | | 10.407 | | 5.19 | 120.76 |
| UF/DF | | | | | | | | | | |
| UF/DF Concentrate | 15/14A | 0.42 | 2.91 | 412.48 | 134 | 390.39 | 83.87 | 94.6 | 4.18 | 87.52 |
| Post-Wash 1 | 15/14B | 0.20 | 1.39 | 13.63 | 10.4 | 14.41 | 3.10 | 105.7 | 0.15 | 3.23 |
| Sum | | | | | | | | | | 100% UF/DF |
| Bulk | 16/1 | 0.53 | 3.97 | 415.03 | 101 | 400.71 | 86.09 | 96.55 | 4.30 | 102.64 |
| EB | 19/1 | 0.53 | 3.97 | 415.03 | 102 | 404.68 | 86.94 | 97.51 | 4.34 | 103.66 |

TABLE 23

IgG content of the downstream fractions formed during fractionation of plasma using an initial low pH (5.4), high alcohol (25% ethanol) precipitation reaction, and an ANX anion exchange loading concentration of 150 mg/mL ANX resin (P03110NG2).

| Sample | | Weight (kg) | Corr. Weight (kg) corr. | Protein (g) | IgG mg/ml | g | Yield (%) | Purity (%) | g/l Plasma | Step Yield % |
|---|---|---|---|---|---|---|---|---|---|---|
| PptG Suspension and Filtration | | | | | | | | | | |
| PptG Susp. | 10/2 | 8.36 | 8.36 | 644.59 | 56.7 | 465.47 | 100 | 72.2 | 4.99 | |
| PptG Filtrat. | 10/6 | 15.91 | 16.24 | 669.20 | 30 | 487.34 | 104.70 | 72.8 | 5.22 | |
| PptG Filtrat verd. | 10/7 | 32.50 | 33.43 | 658.56 | 13.7 | 458.05 | 98.41 | 69.6 | 4.91 | 100.00 |
| CM Sepharose | | | | | | | | | | |
| D | 12/12 A | 38.00 | 53.88 | 48.9 | 0.0037 | 5.05 | 1.08 | 10.3 | 0.054 | 1.10 |
| W | 12/12 B | 127.60 | 180.91 | 0.54 | <0.0712 | | | | | 0.00 |
| VL | 12/12 C | 2.41 | 3.41 | 0.04 | <0.0712 | | | | | 0.00 |
| Eluate | 12/12 D | 13.40 | 19.00 | 580.49 | 23.5 | 452.17 | 97.14 | 77.9 | 4.88 | 95.72 |
| NL | 12/12 E | 1.18 | 1.67 | 2.18 | 0.642 | 1.07 | 0.23 | 49.1 | 0.01 | 0.23 |
| 2M NaCl | 12/12 F | 15.01 | 21.28 | 9.69 | 0.163 | 3.47 | 0.75 | 35.8 | 0.04 | 0.76 |
| Sum | | | | | | | 99.20 | | 4.95 | 100.81 |
| Diluted Eluate | 12/13 | 4.3377 | 37.49 | 599.85 | 10.9 | 408.65 | 87.79 | 68.1 | 4.38 | 100.00 |

TABLE 23-continued

IgG content of the downstream fractions formed during fractionation of plasma using an initial low pH (5.4), high alcohol (25% ethanol) precipitation reaction, and an ANX anion exchange loading concentration of 150 mg/mL ANX resin (P03110NG2).

| Sample | | Weight (kg) | Corr. Weight (kg) corr. | Protein (g) | IgG mg/ml | g | Yield (%) | Purity (%) | g/l Plasma | Step Yield % |
|---|---|---|---|---|---|---|---|---|---|---|
| ANX-Sepharose | | | | | | | | | | |
| D/N | 13/6 A | 11.18 | 51.03 | 416.92 | 8.79 | 448.56 | 96.37 | 107.6 | 4.81 | 109.76 |
| 2M NaCl | 13/6 B | 2.37 | 10.83 | 144.25 | 3.11 | 33.68 | 7.24 | 23.3 | 0.36 | 8.24 |
| Sum | | | | | | | 103.60 | | 5.17 | 118.01 |
| UF/DF | | | | | | | | | | |
| UF/DF Concentrate | 15/14A | 0.57 | 2.61 | 425.26 | 150 | 391.90 | 84.19 | 92.2 | 4.20 | 87.37 |
| Post-Wash 1 | 15/14B | 0.55 | 2.51 | 13.46 | 5.87 | 14.76 | 3.17 | 109.7 | 0.16 | 3.29 |
| Sum | | | | | | | | | | 100% UF/DF |
| Bulk | 16/1 | 0.84 | 4.07 | 445.39 | 97 | 394.91 | 84.84 | 88.67 | 4.23 | 100.77 |
| EB | 19/1 | 0.84 | 4.07 | 445.39 | 99.1 | 403.45 | 85.68 | 90.59 | 4.32 | 102.95 |

TABLE 24

Biochemical characterization of the final IgG composition enriched from cryo-poor plasma using an initial low pH (5.4), high alcohol (25% ethanol) precipitation reaction, and an ANX anion exchange loading concentration of 100 mg/mL ANX resin (P03010NG2).

| Test | Unit | Result |
|---|---|---|
| Total Protein - Kjeldahl | mg/ml | 109.9996 |
| Purity (CAE) | Albumin % | 0 |
| | α/β globulin % | 0 |
| | γ-globulin % | 100 |
| | cenat. Protein % | 0 |
| Molecular size distribution | Monomer [%] | 94.8683 |
| | Dimer [%] | 4.9579 |
| | Polymer [%] | 0.0698 |
| | Fragments [%] | 0.104 |
| IgG neph | g/l | 91.3 |
| IgA (ELISA) | mg/ml | 0.05 |
| IgM (ELISA) | mg/dl | 0 |
| Fibrinogen (ELISA) | µg/ml | <0.17 |
| Plasminogen (ELISA) | µg/ml | 0.26 |
| C3 complement | mg/dl | <19.4 |

| Test | Subclass group | Result [mg/mL] |
|---|---|---|
| IgG-subclass distribution | IgG1 (mg/ml) | 47.897 |
| | IgG2 (mg/ml) | 25.8157 |
| | IgG3 (mg/ml) | 6.2317 |
| | IgG4 (mg/ml) | 2.0201 |

| Test | Unit | Result |
|---|---|---|
| IgGi Fc Function tion Hemaggl. | % | 109 |
| Amidolytic activity (PL-1) | nmol/ml min | <10 |
| Anticomple. Activity | % | 38 |
| PKA | % ref lot 3 | 1.399 |
| | IU/ml | 1 |
| | | 1.486 |
| | | 0.957 |
| | | <4 |
| NAPTT | mg | >10 |
| Appearance | | Satisfactory |
| pH | | 4.84 |
| Factor XIa | mIU/mL | <0.04 |
| SN13a | mU/ml | <0.375 |
| Osmolality | mosmol/kg | 266 |

TABLE 24-continued

Biochemical characterization of the final IgG composition enriched from cryo-poor plasma using an initial low pH (5.4), high alcohol (25% ethanol) precipitation reaction, and an ANX anion exchange loading concentration of 100 mg/mL ANX resin (P03010NG2).

| | | |
|---|---|---|
| Density | g/cm3 | 1.0346 |
| Thrombin generation assay | | 122.66 |
| Complement factor I | µg/ml | 69.1 |
| Amidolytic activity profit | S-2288 | <5 |
| | S-2266 | <5 |
| | S-2222 | <5 |
| | S-2251 | <5 |
| | S-2302 | <5 |
| SD reagents | | |
| Octoxynol 9 (Triton X100) | ppm | <0.1 |
| Polysorbate 80 | ppm | <26 |
| Tri(n-butyl)phosphate | ppm | 0.1178 |
| Antibodies | | |
| Anti D Antibodies | | Satisfactory |
| Anti A&AntiB Hemagglutinins | Anti A | 16 |
| | Anti B | 4 |

TABLE 25

Biochemical characterization of the final IgG composition enriched from cryo-poor plasma using an initial low pH (5.4), high alcohol (25% ethanol) precipitation reaction, and an ANX anion exchange loading concentration of 150 mg/mL ANX resin (P03110NG2).

| Test | Unit | Result |
|---|---|---|
| Total Protein - Kjeldahl | mg/ml | 108.3393 |
| Purity (CAE) | Albumin % | 0 |
| | α/β globulin % | 0 |
| | γ-globulin % | 100 |
| | denat. Protein % | 0 |
| Molecular size distribution | Monomer [%] | 94.9047 |
| | Dimer [%] | 4.9122 |
| | Polymer [%] | 0.0762 |
| | Fragments [%] | 0.1068 |
| IgG neph | g/l | 95.7 |
| IgA (ELISA) | mg/ml | 0.08 |
| IgM (ELISA) | mg/dl | 0 |
| Fibrinogen (ELISA) | µg/ml | 0.33 |

TABLE 25-continued

Biochemical characterization of the final IgG composition enriched from cryo-poor plasma using an initial low pH (5.4), high alcohol (25% ethanol) precipitation reaction, and an ANX anion exchange loading concentration of 150 mg/mL ANX resin (P03110NG2).

| | | |
|---|---|---|
| Plasminogen (ELISA) | μg/ml | 0.27 |
| C3 complement | mg/dl | <19.4 |

| Test | Subclassgroup | Result [mg/ML] |
|---|---|---|
| IgG-subclass distribution | IgG1 (mg/ml) | 54.0113 |
| | IgG2 (mg/ml) | 28.6462 |
| | IgG3 (mg/ml) | 6.0688 |
| | IgG4 (mg/ml) | 2.3599 |

| Test | Unit | Result |
|---|---|---|
| IgG Fc Function Hemaggl. | % | 91 |
| Amidolytic activity (PL-1) | nmcl/ml min | <10 |
| Anticomple. Activity | % | 36 |
| PKA | % ref lot 3 | 2.261 |
| | IU/ml | 1.8 |
| | | 1.864 |
| | | 0.763 |
| | | <4 |
| NAPTT | mg | >10 |
| Appearance | | Satisfactory |
| pH | | 4.853 |
| Factor XIa | mU/ml | <0.04 |
| SN13a | mU/ml | 31.3 |
| Osmolality | mosmol/kg | 266 |
| Thrombin generation assay | | 109.81 |
| Density | g/cm3 | 1.0344 |
| Complement factor I | μg/ml | 147 |
| Amidolytic activity profit | S-2288 | <5 |
| | S-2266 | <5 |
| | S-2222 | <5 |
| | S-2251 | <5 |
| | S-2302 | <5 |
| SD reagents | | |
| Octoxynol 9 (Triton X100) | ppm | <0.1 |
| Polysorbate 80 | ppm | <26 |
| Tri(n-butyl)phosphate | ppm | 0.1414 |
| Antibodies | | |
| Anti D Antibodies | | Satisfactory |
| Anti A&AntiB Hemagglutinins | Anti A | 16 |
| | Anti B | 4 |

Example 6—NG2C107B

The feasibility of extracting alpha-1-antitrypsin (A1PI) from the insoluble portion of a low pH, high alcohol precipitate used in the manufacture of IgG immunoglobulins was investigated. Briefly, two 500 kg samples (#1 and #3) of the insoluble filtercake formed during filtration of the extracted Fraction I-IV-1 precipitate were first suspended in 2.8 parts water (w/w) at 7±2° C. and the pH of the samples was adjusted to 5.5±0.1. The suspensions were filtered through a CUNO 10CP membrane, forming filtrates (1. Filtrat) and second filtercakes. The second filtercakes were then suspended in 5 parts water (w/w), the temperature of the suspensions was adjusted to 17±2° C., the pH of the samples adjusted to 8.8±0.2, and the samples were then stirred for 8 hours while maintaining the temperature and pH to extract A1PI from the insoluble material.

After the incubation, 10 mmol Tris and 150 mmol sodium chloride per kg suspension were added to the samples and the pH was adjusted to 8.0±0.1. 176 g of PEG 3350 per kg suspension was added to the samples, which were incubated at 17±2° C. for 1 hour. The suspensions were then filtered to remove the insoluble material from the supernatant (2. Filtrat) containing the extracted A1PI.

Crude A1PI was then precipitated from the second filtrate by the addition of either 0.35 g zinc chloride/kg filtrate (2.5 mM ZnCl; sample #1) or 0.54 g/kg zinc chloride/kg filtrate (4.0 mM ZnCl; sample #3), adjusting the pH to 7.5±0.2, and incubating the samples at 7±2° C. for 3 hours. The zinc chloride precipitate was recovered by centrifugation ($ZnCl_2$ cent). A1PI was extracted from the zinc chloride precipitate with 50 mM sodium EDTA (Zn-EDTA-conz).

The A1PI (a1A) content and activity was determined for each step in the enrichment process and is presented in Table 26. About 400 mg of active A1PI/L source plasma was recovered in the EDTA extraction step. Notably, when A1PI was extracted at 38±2° C. and a pH of about 9.2, approximately 600 mg of active A1PI/L source plasma was recovered.

TABLE 26 alpha-1-antitrypsin content of the downstream fractions formed during fractionation of plasma using an initial low pH (5.4), high alcohol (25% ethanol) precipitation reaction, and zinc precipitation.

| | | weight (g) | weight corr (g) | a1A ELISA | | | | a1A-Activity OC | | | |
|---|---|---|---|---|---|---|---|---|---|---|---|
| | | | | (mg/mL) | mg | mg/L plasma | purity (% of Biuret) | (mg/mL) | mg | mg/L plasma | % activity vs ELISA |
| 1 | Filtercake | 500.50 | | | | | | | | | |
| | Cake suspension | 1900.40 | 1900.40 | | | | | | | | |
| | Cake susp. cent | 32.71 | 1209.85 | 0.0964 | 117 | 32.32 | 7.69 | 0.02 | 24 | 6.71 | 20.7 |
| | 1. Filtrate | 3291.90 | 3380.85 | <0.0175 | <59 | <16.40 | <5.32 | 0.01 | 34 | 9.37 | 57.1 |
| | Extr. n.pH | 3956.90 | 4063.82 | | | | | | | | |
| | Extr. n.pH cent | 42.61 | 3385.99 | 0.636 | 2153 | 596.84 | 10.09 | 0.43 | 1456 | 403.52 | 67.6 |
| | 2. Filtrate | 7357.80 | 7653.33 | 0.295 | 2258 | 625.73 | 15.96 | 0.2 | 1531 | 424.22 | 67.8 |
| | $ZnCl_2$ cent | 7487.40 | 7841.42 | | | | | | | | |
| | $ZnCl_2$ cent excl. conc | 7305.73 | 7651.16 | 0.00646 | 49 | 13.70 | 1.13 | | | | |
| | Zn-EDTA-conc | 1150.58 | 1204.98 | 1.83 | 2205 | 611.15 | 23.41 | 1.13 | 1362 | 377.37 | 61.7 |

TABLE 26-continued alpha-1-antitrypsin content of the downstream fractions formed during
fractionation of plasma using an initial low pH (5.4), high alcohol (25% ethanol) precipitation
reaction, and zinc precipitation.

|   |   | weight (g) | weight corr (g) | a1A ELISA | | | | a1A-Activity OC | | | |
|---|---|---|---|---|---|---|---|---|---|---|---|
|   |   |   |   | (mg/mL) | mg | mg/L plasma | purity (% of Biuret) | (mg/mL) | mg | mg/L plasma | % activity vs ELISA |
| 3 | Filtercake | 506.5 |   |   |   |   |   |   |   |   |   |
|   | Cake suspension | 1926.30 | 1926.30 |   |   |   |   |   |   |   |   |
|   | Cake susp. cent | 32.50 | 1224.18 | 0.102 | 125 | 34.20 | 7.92 | 0.02 | 24 | 6.71 | 19.6 |
|   | 1. Filtrate | 3448.10 | 3539.99 | <0.0175 | <62 | <16.97 | <5.40 | 0.01 | 35 | 9.69 | 57.1 |
|   | Extr. n.pH | 4175.90 | 4287.18 |   |   |   |   |   |   |   |   |
|   | Extr. n.pH cent | 43.03 | 3611.54 | 0.589 | 2127 | 582.57 | 9.33 | 0.42 | 1517 | 415.41 | 71.3 |
|   | 2. Filtrate | 7860.20 | 8167.45 | 0.314 | 2565 | 702.35 | 17.97 | 0.15 | 1225 | 335.52 | 47.8 |
|   | ZnCl$_2$ cent | 8112.00 | 8483.06 |   |   |   |   |   |   |   |   |
|   | ZnCl$_2$ cent excl. conc | 7913.50 | 8275.48 | 0.00319 | 26 | 7.23 | 0.59 |   |   |   |   |
|   | Zn-EDTA-conz | 1485.86 | 1553.83 | 1.38 | 2144 | 587.25 | 22.87 | 0.86 | 1336 | 365.96 | 62.3 |

Example 7—P03410NG2A and B

The effect of pH on the recovery of IgG from a low pH, high alcohol precipitation of cryo poor plasma was investigated. Briefly, 100 L of cryo-poor plasma that had been treated to remove Factor IX, Factor VII, and antithrombin III (ATIII) by adsorption, was fractionated by precipitation using 25% ethanol at a pH of either 5.4 (Sample A; P03410NG2A) or 5.6 (Sample B; P03410NG2B). The samples were then processed to form a Precipitate G precipitate (PptG precipitate) and supernatant (PptG supernatant) as described in Example 2, except that 50 g SiO$_2$/kg precipitate I-IV-1 was admixed with the precipitate I-IV-1 suspension, rather than 40 g/kg precipitate.

The IgG, IgA, and IgM contents of the fractions formed were determined and are reported in Table 27, Table 28, and Table 29, respectively. Notably, about 90% of the IgG content of the source plasma is recovered in the Fraction I-IV-1 CUNO filtrate when the initial precipitation is performed at pH 5.4 (93.8%) or pH 5.6 (88.8%). Similarly, nearly all of the IgA and IgM content of the source plasma is recovered in the Fraction I-IV-1 suspension.

TABLE 27

IgG content of the upstream fractions formed during fractionation of plasma using a
low pH (A = 5.4; B = 5.6), high alcohol (25%) initial precipitation step.

|   |   |   | weight kg | weight calc. kg | IgG nephelometry IPC/ELISA | | | | |
|---|---|---|---|---|---|---|---|---|---|
|   |   |   |   |   | mg/ml | g | % | purity (%) | g/l plasma |
| A |   | Cohn Pool | 101.20 | 101.20 | 6.01 | 608.21 | 100.00 | 12.65 | 6.01 |
|   |   | Cohn Pool | 101.82 | 101.20 | 5.96 | 603.15 | 100.00 | 12.55 | 5.96 |
|   | I-IV-1 precipitation | I-IV1 prior EtOH addition | 101.82 | 102.28 |   |   |   |   |   |
|   |   | I-IV1 after EtOH addition | 131.62 | 132.21 |   |   |   |   |   |
|   |   | I-IV1 supernatant | 123.40 | 124.23 | 0.00427 | 0.53 | 0.09 | 0.02 | 0.01 |
|   |   | I-IV1 precipitate | 7.11 | 7.16 |   |   |   |   |   |
|   | I-IV-1 extraction a. filtration | I-IV1 precipitate used | 7.07 | 7.16 |   |   |   |   |   |
|   |   | I-IV1 suspesion | 113.87 | 115.33 | 4.47 | 515.52 | 84.76 | 24.20 | 5.09 |
|   |   | CUNO filtrate | 222.10 | 225.45 | 2.53 | 570.39 | 93.78 | 40.77 | 5.64 |
|   | PptG precipitation | PptG-precipitation | 2.40 | 2.44 |   |   |   |   |   |
|   |   | PptG supernatant | 288.20 | 292.81 | 0.0276 | 8.08 | 1.33 | 1.29 | 0.08 |
| B |   | Cohn Pool | 100.80 | 100.80 | 6.01 | 605.81 | 100.00 | 12.65 | 6.01 |
|   | I-IV-1 precipitation | I-IV1 prior EtOH addition | 101.43 | 101.53 |   |   |   |   |   |
|   |   | I-IV1 after EtOH addition | 131.43 | 131.56 |   |   |   |   |   |
|   |   | I-IV1 supernatant | 123.40 | 123.81 | 0.0113 | 1.40 | 0.23 | 0.05 | 0.01 |
|   |   | I-IV1 precipitate | 6.52 | 6.55 |   |   |   |   |   |
|   | I-IV-1 extraction a. filtration | I-IV1 precipitate used | 6.49 | 6.55 |   |   |   |   |   |
|   |   | I-IV1 suspension | 104.49 | 105.46 | 3.80 | 400.74 | 66.15 | 19.67 | 3.98 |
|   |   | CUNO filtrate | 201.60 | 203.86 | 2.64 | 538.19 | 88.84 | 46.74 | 5.34 |
|   | PptG-precipitation | PptG precipitation | 2.19 | 2.21 |   |   |   |   |   |
|   |   | PptG supernatant | 261.40 | 264.60 | 0.0200 | 5.29 | 0.87 | 1.25 | 0.05 |

ELISA
IgG neph PPD/PS

TABLE 28

IgA content of the upstream fractions formed during fractionation of plasma using a
low pH (A = 5.4; B = 5.6), high alcohol (25%) initial precipitation step.

| | | weight kg | weight calc. kg | IgA ELISA mg/ml | g | % | purity (%) | g/l plasma |
|---|---|---|---|---|---|---|---|---|
| A | Cohn Pool | 101.20 | 101.20 | 1.1187 | 113.21 | 100.00 | 2.36 | 1.12 |
| I-IV-1 precipitation | I-IV1 prior EtOH addition | 101.91 | 102.37 | | | | | |
| | I-IV1 after EtOH addition | 131.71 | 132.30 | | | | | |
| | I-IV1 supernatant | 123.40 | 124.23 | 0.0027 | 0.34 | 0.06 | 0.01 | 0.003 |
| | I-IV1 precipitate | 7.11 | 7.16 | | | | | |
| I-IV-1 extraction a. filtration | I-IV1 precipitate used | 7.07 | 7.16 | | | | | |
| | I-IV1 suspension | 113.87 | 115.33 | 1.03 | 118.79 | 19.53 | 5.58 | 1.17 |
| | CUNO filtrate | 222.10 | 225.45 | 0.41 | 93.09 | 15.31 | 6.65 | 0.92 |
| PptG-precipitation | PptG precipitation | 2.40 | 2.44 | | | | | |
| | PptG supernatant | 288.20 | 292.81 | | | | | |
| B | Cohn Pool | 100.80 | 100.80 | 1.1187 | 112.76 | 100.00 | 2.36 | 1.12 |
| I-IV-1 precipitation | I-IV1 prior EtOH addition | 101.43 | 101.53 | | | | | |
| | I-IV1 after EtOH addition | 131.43 | 131.56 | | | | | |
| | I-IV1 supernatant | 123.40 | 123.81 | 0.0073 | 0.90 | 0.15 | 0.03 | 0.009 |
| | I-IV1 precipitate | 6.52 | 6.55 | | | | | |
| I-IV-1 extraction a. filtration | I-IV1 precipitate used | 6.49 | 6.55 | | | | | |
| | I-IV1 suspension | 104.49 | 105.46 | 1.03 | 108.62 | 17.93 | 5.33 | 1.08 |
| | CUNO filtrate | 201.60 | 203.86 | 0.47 | 95.00 | 15.68 | 8.25 | 0.94 |
| PptG-precipitation | PptG precipitation | 2.19 | 2.21 | | | | | |
| | PptG supernatant | 261.40 | 264.60 | | | | | |

TABLE 29

IgM content of the upstream fractions formed during fractionation of plasma using a
low pH (A = 5.4; B = 5.6), high alcohol (25%) initial precipitation step.

| | | weight kg | weight calc. kg | IgM ELISA mg/ml | g | % | purity (%) | g/l plasma |
|---|---|---|---|---|---|---|---|---|
| A | Cohn Pool | 101.20 | 101.20 | 0.4381 | 44.34 | 100.00 | 0.92 | 0.44 |
| I-IV1-precipitation | I-IV1 prior EtOH addition | 101.91 | 102.37 | | | | | |
| | I-IV1 after EtOH addition | 131.71 | 132.30 | | | | | |
| | I-IV1 supernatant | 123.40 | 124.23 | 0.00014 | 0.02 | 0.00 | 0.00 | 0.0002 |
| | I-IV1 precipitate | 7.11 | 7.16 | | | | | |
| I-IV1 extraction a. filtration | I-IV1 precipitate used | 7.07 | 7.16 | | | | | |
| | I-IV1 suspension | 113.87 | 115.33 | 0.4042 | 46.62 | 7.66 | 2.19 | 0.46 |
| | CUNO filtrate | 222.10 | 225.45 | 0.1506 | 33.95 | 5.58 | 2.43 | 0.34 |
| PptG-precipitation | PptG precipitation | 2.40 | 2.44 | | | | | |
| | PptG supernatant | 288.20 | 292.81 | | | | | |
| B | Cohn Pool | 100.80 | 100.80 | 0.4381 | 44.16 | 100.00 | 0.92 | 0.44 |
| I-IV1-precipitation | I-IV1 prior EtOH addition | 101.43 | 101.53 | | | | | |
| | I-IV1 after EtOH addition | 131.43 | 131.56 | | | | | |
| | I-IV1 supernatant | 123.40 | 123.81 | 0.00029 | 0.04 | 0.01 | 0.00 | 0.0004 |
| | I-IV1 precipitate | 6.52 | 6.55 | | | | | |
| I-IV1 extraction a. filtration | I-IV1 precipitate used | 6.49 | 6.55 | | | | | |
| | I-IV1 suspension | 104.49 | 105.46 | 0.4323 | 45.59 | 7.53 | 2.24 | 0.45 |
| | CUNO filtrate | 201.60 | 203.86 | 0.1360 | 27.73 | 4.58 | 2.41 | 0.28 |
| PptG-precipitation | PptG precipitation | 2.19 | 2.21 | | | | | |
| | PptG supernatant | 261.40 | 264.60 | | | | | |

To further characterize the fractionation scheme, the contents of fibrinogen (Table 30), A1PI (Table 31), Alpha-2-Macroglobulin (Table 32), albumin (Table 33), Transferrin (Table 34), and C3 (Table 35) were determined for various upstream fractions.

TABLE 30 fibrinogen content of the upstream fractions formed during fractionation of plasma using a low pH (A = 5.4; B = 5.6), high alcohol (25%) initial precipitation step.

| | | weight kg | calc. kg | Fibrinogen ELISA mg/ml | g | % | purity (%) | g/l plasma |
|---|---|---|---|---|---|---|---|---|
| A | | | | | | | | |
| | Cohn Pool | 101.20 | 101.20 | 1.698 | 171.84 | 100.00 | 3.57 | 1.70 |
| I-IV1-precipitation | I-IV1 prior EtOH addition | 101.91 | 102.37 | | | | | |
| | I-IV1 after EtOH addition | 131.71 | 132.30 | | | | | |
| | I-IV1 supernatant | 123.40 | 124.23 | <0.0001 | 0.01 | 0.00 | 0.00 | 0.00 |
| | I-IV1 precipitate | 7.11 | 7.16 | | | | | |
| I-IV1 extraction a. filtration | I-IV1 precipitate used | 7.07 | 7.16 | | | | | |
| | I-IV1 suspension | 113.87 | 115.33 | 1.14 | 131.01 | 21.54 | 6.15 | 1.29 |
| | CUNO filtrate | 222.10 | 225.45 | 0.03 | 6.52 | 1.07 | 0.47 | 0.06 |
| PptG-precipitation | PptG precipitation | 2.40 | 2.44 | | | | | |
| | PptG supernatant | 288.20 | 292.81 | | | | | |
| B | | | | | | | | |
| | Cohn Pool | 100.80 | 100.80 | 1.698 | 171.16 | 100.00 | 3.57 | 1.70 |
| I-IV1-precipitation | I-IV1 prior EtOH addition | 101.43 | 101.53 | | | | | |
| | I-IV1 after EtOH addition | 131.43 | 131.56 | | | | | |
| | I-IV1 supernatant | 123.40 | 123.81 | 0.00087 | 0.11 | 0.02 | 0.00 | 0.00 |
| | I-IV1 precipitate | 6.52 | 6.55 | | | | | |
| I-IV1 extraction a. filtration | I-IV1 precipitate used | 6.49 | 6.55 | | | | | |
| | I-IV1 suspension | 104.49 | 105.46 | 1.58 | 166.52 | 27.49 | 8.17 | 1.65 |
| | CUNO filtrate | 201.60 | 203.86 | 0.02 | 4.65 | 0.77 | 0.40 | 0.05 |
| PptG-precipitation | PptG precipitation | 2.19 | 2.21 | | | | | |
| | PptG supernatant | 261.40 | 264.60 | | | | | |

TABLE 31 alpha-1-antitrypsin content of the upstream fractions formed during fractionation of plasma using a low pH (A = 5.4; B = 5.6), high alcohol (25%) initial precipitation step.

| | | weight kg | calc. kg | alpha 1 antitrypsin ELISA mg/ml | g | % | purity (%) | g/l plasma |
|---|---|---|---|---|---|---|---|---|
| A | | | | | | | | |
| | Cohn Pool | 101.20 | 101.20 | 1.15 | 116.38 | 100.00 | 2.42 | 1.15 |
| I-IV1-precipitation | I-IV1 prior EtOH addition | 101.91 | 102.37 | | | | | |
| | I-IV1 after EtOH addition | 131.71 | 132.30 | | | | | |
| | I-IV1 supernatant | 123.40 | 124.23 | 0.0097 | 1.21 | 0.20 | 0.05 | 0.01 |
| | I-IV1 precipitate | 7.11 | 7.16 | | | | | |
| I-IV1 extraction a. filtration | I-IV1 precipitate used | 7.07 | 7.16 | | | | | |
| | I-IV1 suspension | 113.87 | 115.33 | 0.257 | 29.64 | 4.87 | 1.39 | 0.29 |
| | CUNO filtrate | 222.10 | 225.45 | 0.0502 | 11.32 | 1.86 | 0.81 | 0.11 |
| PptG-precipitation | PptG precipitation | 2.40 | 2.44 | | | | | |
| | PptG supernatant | 288.20 | 292.81 | 0.0267 | 7.82 | 1.29 | 1.25 | 0.08 |
| B | | | | | | | | |
| | Cohn Pool | 100.80 | 100.80 | 1.15 | 115.92 | 100.00 | 2.42 | 1.15 |
| I-IV1-precipitation | I-IV1 prior EtOH addition | 101.43 | 101.53 | | | | | |
| | I-IV1 after EtOH addition | 131.43 | 131.56 | | | | | |
| | I-IV1 supernatant | 123.40 | 123.81 | 0.0221 | 2.74 | 0.45 | 0.10 | 0.03 |
| | I-IV1 precipitate | 6.52 | 6.55 | | | | | |

TABLE 31-continued alpha-1-antitrypsin content of the upstream fractions formed during fractionation of plasma using a low pH (A = 5.4; B = 5.6), high alcohol (25%) initial precipitation step.

| | | weight kg | calc. kg | \multicolumn{4}{c}{alpha 1 antitrypsin ELISA} | g/l plasma |
| | | | | mg/ml | g | % | purity (%) | |
|---|---|---|---|---|---|---|---|---|
| I-IV1 extraction a. filtration | I-IV1 precipitate used | 6.49 | 6.55 | | | | | |
| | I-IV1 suspension | 104.49 | 105.46 | 0.365 | 38.49 | 6.35 | 1.89 | 0.38 |
| | CUNO filtrate | 201.60 | 203.86 | 0.0597 | 12.17 | 2.01 | 1.06 | 0.12 |
| PptG-precipitation | PptG precipitation | 2.19 | 2.21 | | | | | |
| | PptG supernatant | 261.40 | 264.60 | 0.0300 | 7.94 | 1.31 | 1.88 | 0.08 |

TABLE 32

Alpha-2-Macroglobulin content of the upstream fractions formed during fractionation of plasma using a low pH (A = 5.4; B = 5.6), high alcohol (25%) initial precipitation step.

| | | | weight kg | calc. kg | \multicolumn{4}{c}{alpha 2 macroglobulin ELISA} | g/l plasma |
| | | | | | mg/ml | g | % | purity (%) | |
|---|---|---|---|---|---|---|---|---|---|
| A | | Cohn Pool | 101.20 | 101.20 | 1.08 | 109.30 | 100.00 | 2.27 | 1.08 |
| | I-IV1-precipitation | I-IV1 prior EtOH addition | 101.91 | 102.37 | | | | | |
| | | I-IV1 after EtOH addition | 131.71 | 132.30 | | | | | |
| | | I-IV1 supernatant | 123.40 | 124.23 | 0.00041 | 0.05 | 0.01 | 0.002 | 0.001 |
| | | I-IV1 precipitate | 7.11 | 7.16 | | | | | |
| | I-IV1 extraction a. filtration | I-IV1 precipitate used | 7.07 | 7.16 | | | | | |
| | | I-IV1 suspension | 113.87 | 115.33 | 0.945 | 108.99 | 17.92 | 5.12 | 1.08 |
| | | CUNO filtrate | 222.10 | 225.45 | 0.533 | 120.17 | 19.76 | 8.59 | 1.19 |
| | PptG-precipitation | PptG precipitation | 2.40 | 2.44 | | | | | |
| | | PptG supernatant | 288.20 | 292.81 | 0.158 | 46.26 | 7.61 | 7.38 | 0.46 |
| B | | Cohn Pool | 100.80 | 100.80 | 1.08 | 108.86 | 100.00 | 2.27 | 1.08 |
| | I-IV1-precipitation | I-IV1 prior EtOH addition | 101.43 | 101.53 | | | | | |
| | | I-IV1 after EtOH addition | 131.43 | 131.56 | | | | | |
| | | I-IV1 supernatant | 123.40 | 123.81 | 0.00105 | 0.13 | 0.02 | 0.005 | 0.001 |
| | | I-IV1 precipitate | 6.52 | 6.55 | | | | | |
| | I-IV1 extraction a. filtration | I-IV1 precipitate used | 6.49 | 6.55 | | | | | |
| | | I-IV1 suspension | 104.49 | 105.46 | 1.06 | 111.78 | 18.45 | 5.49 | 1.11 |
| | | CUNO filtrate | 201.60 | 203.86 | 0.559 | 113.96 | 18.81 | 9.90 | 1.13 |
| | PptG-precipitation | PptG precipitation | 2.19 | 2.21 | | | | | |
| | | PptG supernatant | 261.40 | 264.60 | 0.142 | 37.57 | 6.20 | 8.88 | 0.37 |

TABLE 33 albumin content of the upstream fractions formed during fractionation of plasma using a low pH (A = 5.4; B = 5.6), high alcohol (25%) initial precipitation step.

| | | | weight kg | calc. kg | \multicolumn{4}{c}{Albumin ELISA} | g/l plasma |
| | | | | | mg/ml | g | % | purity (%) | |
|---|---|---|---|---|---|---|---|---|---|
| A | | Cohn Pool | 101.20 | 101.20 | 25.1 | 2540.12 | 100.00 | 52.84 | 25.10 |
| | I-IV1-precipitation | I-IV1 prior EtOH addition | 101.91 | 102.37 | | | | | |
| | | I-IV1 after EtOH addition | 131.71 | 132.30 | | | | | |

TABLE 33-continued albumin content of the upstream fractions formed during fractionation of
plasma using a low pH (A = 5.4; B = 5.6), high alcohol (25%) initial precipitation step.

|   |   |   | weight kg | weight calc. kg | Albumin ELISA mg/ml | g | % | purity (%) | g/l plasma |
|---|---|---|---|---|---|---|---|---|---|
|   |   | I-IV1 supernatant | 123.40 | 124.23 | 18.5 | 2298.33 | 377.88 | 92.24 | 22.71 |
|   |   | I-IV1 precipitate | 7.11 | 7.16 |   |   |   |   |   |
|   | I-IV1 extraction a. filtration | I-IV1 precipitate used | 7.07 | 7.16 |   |   |   |   |   |
|   |   | I-IV1 suspension | 113.87 | 115.33 | 2.33 | 268.72 | 44.18 | 12.61 | 2.66 |
|   |   | CUNO filtrate | 222.10 | 225.45 | 1.19 | 268.29 | 44.11 | 19.18 | 2.65 |
|   | PptG-precipitation | PptG precipitation | 2.40 | 2.44 |   |   |   |   |   |
|   |   | PptG supernatant | 288.20 | 292.81 | 0.866 | 253.57 | 41.69 | 40.43 | 2.51 |
| B |   | Cohn Pool | 100.80 | 100.80 | 25.1 | 2530.08 | 100.00 | 52.84 | 25.10 |
|   | I-IV1-precipitation | I-IV1 prior EtOH addition | 101.43 | 101.53 |   |   |   |   |   |
|   |   | I-IV1 after EtOH addition | 131.43 | 131.56 |   |   |   |   |   |
|   |   | I-IV1 supernatant | 123.40 | 123.81 | 19.9 | 2463.72 | 406.68 | 91.43 | 24.44 |
|   |   | I-IV1 precipitate | 6.52 | 6.55 |   |   |   |   |   |
|   | I-IV1 extraction a. filtration | I-IV1 precipitate used | 6.49 | 6.55 |   |   |   |   |   |
|   |   | I-IV1 suspension | 104.49 | 105.46 | 1.57 | 165.57 | 27.33 | 8.13 | 1.64 |
|   |   | CUNO filtrate | 201.60 | 203.86 | 0.693 | 141.28 | 23.32 | 12.27 | 1.40 |
|   | PptG-precipitation | PptG precipitation | 2.19 | 2.21 |   |   |   |   |   |
|   |   | PptG supernatant | 261.40 | 264.60 | 0.543 | 143.68 | 23.72 | 33.96 | 1.43 |

TABLE 34

Transferrin content of the upstream fractions formed during fractionation of
plasma using a low pH (A = 5.4; B = 5.6), high alcohol (25%) initial precipitation step.

|   |   |   | weight kg | weight calc. kg | Transferrin ELISA mg/ml | g | % | purity (%) | g/l plasma |
|---|---|---|---|---|---|---|---|---|---|
| A |   | Cohn Pool | 101.20 | 101.20 | 1.95 | 197.34 | 100.00 | 4.11 | 1.95 |
|   | I-IV1-precipitation | I-IV1 prior EtOH addition | 101.91 | 102.37 |   |   |   |   |   |
|   |   | I-IV1 after EtOH addition | 131.71 | 132.30 |   |   |   |   |   |
|   |   | I-IV1 supernatant | 123.40 | 124.23 | 0.343 | 42.61 | 7.01 | 1.71 | 0.42 |
|   |   | I-IV1 precipitate | 7.11 | 7.16 |   |   |   |   |   |
|   | I-IV1 extraction a. filtration | I-IV1 precipitate used | 7.07 | 7.16 |   |   |   |   |   |
|   |   | I-IV1 suspension | 113.87 | 115.33 | 1.38 | 159.16 | 26.17 | 7.47 | 1.57 |
|   |   | CUNO filtrate | 222.10 | 225.45 | 0.655 | 147.67 | 24.28 | 10.56 | 1.46 |
|   | PptG-precipitation | PptG precipitation | 2.40 | 2.44 |   |   |   |   |   |
|   |   | PptG supernatant | 288.20 | 292.81 | 0.541 | 158.41 | 26.05 | 25.26 | 1.57 |
| B |   | Cohn Pool | 100.80 | 100.80 | 1.95 | 196.56 | 100.00 | 4.11 | 1.95 |
|   | I-IV1-precipitation | I-IV1 prior EtOH addition | 101.43 | 101.53 |   |   |   |   |   |
|   |   | I-IV1 after EtOH addition | 131.43 | 131.56 |   |   |   |   |   |
|   |   | I-IV1 supernatant | 123.40 | 123.81 | 0.825 | 102.14 | 16.86 | 3.79 | 1.01 |
|   |   | I-IV1 precipitate | 6.52 | 6.55 |   |   |   |   |   |
|   | I-IV1 extraction a. filtration | I-IV1 precipitate used | 6.49 | 6.55 |   |   |   |   |   |
|   |   | I-IV1 suspension | 104.49 | 105.46 | 1.13 | 119.17 | 19.67 | 5.85 | 1.18 |
|   |   | CUNO filtrate | 201.60 | 203.86 | 0.527 | 107.44 | 17.73 | 9.33 | 1.07 |
|   | PptG-precipitation | PptG precipitation | 2.19 | 2.21 |   |   |   |   |   |
|   |   | PptG supernatant | 261.40 | 264.60 | 0.383 | 101.34 | 16.73 | 23.95 | 1.01 |

TABLE 35

Complement Component 3 (C3) content of the upstream fractions formed
during fractionation of plasma using a low pH (A = 5.4; B = 5.6), high alcohol (25%) initial
precipitation step.

|   |   |   | weight | weight calc. | | C3 ELISA | | | |
|---|---|---|---|---|---|---|---|---|---|
|   |   |   | weight kg | calc. kg | mg/ml | g | % | purity (%) | g/l plasma |
| A | I-IV1-precipitation | Cohn Pool | 101.20 | 101.20 | 0.0648 | 6.56 | 100.00 | 0.14 | 0.06 |
|   |   | I-IV1 prior EtOH addition | 101.91 | 102.37 | | | | | |
|   |   | I-IV1 after EtOH addition | 131.71 | 132.30 | | | | | |
|   |   | I-IV1 supernatant | 123.40 | 124.23 | <0.00006 | <0.007 | <0.001 | <0.0003 | <0.0001 |
|   |   | I-IV1 precipitate | 7.11 | 7.16 | | | | | |
|   | I-IV1 extraction a. filtration | I-IV1 precipitate used | 7.07 | 7.16 | | | | | |
|   |   | I-IV1 suspension | 113.87 | 115.33 | 0.673 | 77.62 | 12.76 | 3.64 | 0.77 |
|   |   | CUNO filtrate | 222.10 | 225.45 | 0.0476 | 10.73 | 1.76 | 0.77 | 0.11 |
|   | PptG-precipitation | PptG precipitation | 2.40 | 2.44 | | | | | |
|   |   | PptG supernatant | 288.20 | 292.81 | | | | | |
| B | I-IV1-precipitation | Cohn Pool | 100.80 | 100.80 | 0.0648 | 6.53 | 100.00 | 0.14 | 0.06 |
|   |   | I-IV1 prior EtOH addition | 101.43 | 101.53 | | | | | |
|   |   | I-IV1 after EtOH addition | 131.43 | 131.56 | | | | | |
|   |   | I-IV1 supernatant | 123.40 | 123.81 | <0.00006 | <0.007 | <0.001 | <0.0003 | <0.0001 |
|   |   | I-IV1 precipitate | 6.52 | 6.55 | | | | | |
|   | I-IV1 extraction a. filtration | I-IV1 precipitate used | 6.49 | 6.55 | | | | | |
|   |   | I-IV1 suspension | 104.49 | 105.46 | 0.570 | 60.11 | 9.92 | 2.95 | 0.60 |
|   |   | CUNO filtrate | 201.60 | 203.86 | 0.0487 | 9.93 | 1.64 | 0.86 | 0.10 |
|   | PptG-precipitation | PptG precipitation | 2.19 | 2.21 | | | | | |
|   |   | PptG supernatant | 261.40 | 264.60 | | | | | |

Example 8—P03510NG2 and P03610NG2

The effect of passing the CM cation exchange eluate over an ANX anion exchange column at loading concentrations of 100 g protein/mL ANX resin and 150 g protein/mL ANX resin during the downstream processing of a PptG precipitate formed using an initial low pH, high alcohol precipitation step was further investigated. Briefly, 2 kg of P03410NG2A PptG precipitate was processed as described in Example 4, with a first sample (P03510NG2) loaded onto the ANX anion exchange resin at a concentration of 157 mg protein/mL ANX resin and a second sample (P03610NG2) loaded onto the ANX anion exchange resin at a concentration of 106 mg protein/mL ANX resin.

The IgG contents of each downstream step of the purifications were determined and the results are provided in Table 22 and Table 23. As compared to the average IgG yield for the GAMMAGARD LIQUID® manufacturing process (3.7 g IgG/L source plasma), the purification methods used in this example results in a significantly higher yields of 4.72 g IgG and 4.67 g IgG per L source plasma. This represents greater than a 25% increase in the IgG yield. Biochemical characterization of the final IgG compositions are reported in Table 38 and Table 39. As seen in the tables, the final IgG compositions have greater than 99% purity and the IgG monomer/dimer content is greater than 99.8%. The final container contains only traces of impurities, the levels of which are within regulatory standards.

TABLE 36

IgG content of the upstream fractions formed during fractionation of plasma using an
initial low pH (5.4), high alcohol (25%) initial precipitation step and an anion exchange loading
concentration of 157 mg/mL ANX resin (P03510NG2).

| Sample | | Weight (kg) | Corr. Weight (kg) corr. | Protein (g) | IgG mg/ml | g | Yield (%) | Purity (%) | g/l Plasma | Step Yield % |
|---|---|---|---|---|---|---|---|---|---|---|
| PptG Suspension and Filtration | | | | | | | | | | |
| PptG Suspension | 10/2 | 9.63 | 9.63 | 683.69 | 46.4 | 446.62 | 100 | 65.3 | 5.37 | |
| PptG Filtrate | 10/6 | 18.80 | 19.15 | 646.26 | 25 | 482.54 | 108.04 | 74.7 | 5.81 | |
| PptG Filtrate verd. | 10/7 | 31.46 | 32.24 | 643.35 | 14.8 | 477.17 | 106.84 | 74.2 | 5.74 | 100.00 |
| CM Sepharose | | | | | | | | | | |
| D | 12/12 A | 36.40 | 47.57 | 73.2 | 0.188 | 8.942 | 2.002 | 12.212 | 0.108 | 1.87 |
| W | 12/12 B | 109.60 | 143.22 | 3.72 | <0.0712 | | | | | 0.00 |

TABLE 36-continued

IgG content of the upstream fractions formed during fractionation of plasma using an initial low pH (5.4), high alcohol (25%) initial precipitation step and an anion exchange loading concentration of 157 mg/mL ANX resin (P03510NG2).

| Sample | | Weight (kg) | Corr. Weight (kg) corr. | Protein (g) | IgG mg/ml | g | Yield (%) | Purity (%) | g/l Plasma | Step Yield % |
|---|---|---|---|---|---|---|---|---|---|---|
| VL | 12/12 C | 2.41 | 3.15 | 0.00 | <0.0712 | | | | | 0.00 |
| Eluate | 12/12 D | 13.40 | 17.51 | 532.56 | 23.1 | 404.49 | 90.57 | 76.0 | 4.87 | 84.77 |
| NL | 12/12 E | 1.41 | 1.84 | 2.36 | 0.544 | 0.999 | 0.22 | 42.3 | 0.012 | 0.21 |
| 2M NaCl | 12/12 F | 14.81 | 19.35 | 10.44 | 0.196 | 3.79 | 0.85 | 36.3 | 0.046 | 0.79 |
| Sum | | | | | | | 93.64 | | 5.03 | 87.65 |
| Diluted Eluate | 12/13 | 4.3377 | 34.55 | 535.67 | 11.6 | 400.83 | 89.75 | 74.8 | 4.82 | 100.00 |
| ANX-Sepharose | | | | | | | | | | |
| D/N | 13/6 A | 15.60 | 41.90 | 373.70 | 9.73 | 407.64 | 91.27 | 109.1 | 4.91 | 101.70 |
| 2M NaCl | 13/6 B | 3.76 | 10.10 | 120.56 | 3.32 | 33.54 | 7.51 | 27.8 | 0.40 | 8.37 |
| Sum | | | | | | | 98.78 | | 5.31 | 110.07 |
| VR06 Filtrate | 14/2 | 17.15 | 46.30 | 373.66 | | | | | | |
| Asahi 35 nm Filtrate | 14/5 | 18.82 | 50.84 | 371.10 | 8.19 | 416.35 | 93.22 | 112.2 | 5.01 | 103.87 |
| UF/DF | | | | | | | | | | |
| UF/DF Concentrate | 15/14 A | 1.02 | 2.74 | 391.05 | 133 | 364.39 | 81.59 | 93.2 | 4.39 | 89.39 |
| Post-Wash 1 | 15/14 B | 0.74 | 2.00 | 6.94 | 3.53 | 7.08 | 1.58 | 102.0 | 0.09 | 1.74 |
| Sum | | | | | | | | | | 100% UF/DF |
| Bulk | 16/1 | 1.38 | 3.85 | 375.89 | 96.5 | 371.96 | 83.28 | 98.95 | 4.48 | 102.08 |
| EB | 19/1 | 1.21 | 3.81 | 378.80 | 103 | 392.60 | 87.90 | 103.64 | 4.72 | 107.74 |

TABLE 37

IgG content of the upstream fractions formed during fractionation of plasma using an initial low pH (5.4), high alcohol (25%) initial precipitation step and an anion exchange loading concentration of 106 mg/mL ANX resin (P03610NG2).

| Sample | | Weight (kg) | Corr. Weight (kg) corr. | Protein (g) | IgG mg/ml | g | Yield (%) | Purity(%) | g/l Plasma | Step Yield % |
|---|---|---|---|---|---|---|---|---|---|---|
| PptG Suspension and Filtration | | | | | | | | | | |
| PptG Suspension | 10/2 | 9.63 | 9.63 | 683.69 | 46.4 | 446.62 | 100 | 65.3 | 5.37 | |
| PptG Filtrate | 10/6 | 18.80 | 19.15 | 646.26 | 25 | 482.54 | 108.04 | 74.7 | 5.81 | |
| PptG Filtrate verd. | 10/7 | 31.46 | 32.24 | 643.35 | 14.8 | 477.17 | 106.84 | 74.2 | 5.74 | 100.00 |
| CM Sepharose | | | | | | | | | | |
| D | 12/12 A | 36.40 | 47.57 | 73.2 | 0.188 | 8.942 | 2.002 | 12.212 | 0.108 | 1.87 |
| W | 12/12 B | 109.60 | 143.22 | 3.72 | <0.0712 | | | | | 0.00 |
| VL | 12/12 C | 2.41 | 3.15 | 0.00 | <0.0712 | | | | | 0.00 |
| Eluate | 12/12 D | 13.40 | 17.51 | 532.56 | 23.1 | 404.49 | 90.57 | 76.0 | 4.87 | 84.77 |
| NL | 12/12 E | 1.41 | 1.84 | 2.36 | 0.544 | 0.999 | 0.22 | 42.3 | 0.012 | 0.21 |
| 2M NaCl | 12/12 F | 14.81 | 19.35 | 10.44 | 0.196 | 3.79 | 0.85 | 36.3 | 0.046 | 0.79 |
| Sum | | | | | | | 93.64 | | 5.03 | 87.65 |
| Diluted Eluate | 12/13 | 4.3377 | 34.55 | 535.67 | 11.6 | 400.83 | 89.75 | 74.8 | 4.82 | 100.00 |
| ANX-Sepharose | | | | | | | | | | |
| D/N | 13/6 A | 11.80 | 46.90 | 384.12 | 8.46 | 396.78 | 88.84 | 103.3 | 4.77 | 98.99 |
| 2M NaCl | 13/6 B | 3.72 | 14.79 | 123.43 | 2.23 | 32.98 | 7.38 | 26.7 | 0.40 | 8.23 |
| Sum | | | | | | | 96.23 | | 5.17 | 107.22 |
| VR06 Filtrate | 14/2 | 12.88 | 51.53 | 381.83 | | | | | | |
| Asahi 35 nm Filtrate | 14/5 | 14.10 | 56.47 | 378.34 | 6.93 | 391.33 | 87.62 | 103.4 | 4.71 | 97.63 |

TABLE 37-continued

IgG content of the upstream fractions formed during fractionation of plasma using an initial low pH (5.4), high alcohol (25%) initial precipitation step and an anion exchange loading concentration of 106 mg/mL ANX resin (P03610NG2).

| Sample | | Weight (kg) | Corr. Weight (kg) corr. | Protein (g) | IgG mg/ml | g | Yield (%) | Purity(%) | g/l Plasma | Step Yield % |
|---|---|---|---|---|---|---|---|---|---|---|
| UF/DF | | | | | | | | | | |
| UF/DF Concentrate | 15/14A | 0.69 | 2.77 | 385.58 | 125 | 346.49 | 77.58 | 89.9 | 4.17 | 87.33 |
| Post-Wash 1 | 15/14B | 0.78 | 3.12 | 9.96 | 3.4 | 10.62 | 2.38 | 106.6 | 0.13 | 2.68 |
| Sum | | | | | | | | | | 100% UF/DF |
| Bulk | 16/1 | 0.89 | 3.73 | 376.90 | 93.8 | 350.10 | 78.39 | 92.89 | 4.21 | 101.04 |
| EB | 19/1 | 0.89 | 3.73 | 376.90 | 104 | 388.17 | 86.91 | 102.99 | 4.67 | 112.03 |

TABLE 38

Biochemical characterization of the final IgG composition enriched from cryo-poor plasma using an initial low pH (5.4), high alcohol (25%) initial precipitation step and an anion exchange loading concentration of 157 mg/mL ANX resin (P03510NG2).

| Test | Unit | Result |
|---|---|---|
| Total Protein - Kjeldahl | mg/ml | 100.5061 |
| Purity (CAE) | Albumin % | 0 |
| | α/β globulin % | 0 |
| | γ-globulin % | 100 |
| | denat. Protein % | 0 |
| Molecular size distribution | Monomer [%] | 93.1042 |
| | Dimer [%] | 6.7664 |
| | Polymer [%] | 0.0499 |
| | Fragments [%] | 0.0795 |
| IgG neph | g/l | 92.4 |
| IgA (ELISA) | mg/ml | 0.07 |
| IgM (ELISA) | mg/dl | <0.95 |
| Fibrinogen (ELISA) | µg/ml | <0.17 |
| Plasminogen (ELISA) | µg/ml | 0.32 |
| C3 complement | mg/dl | <19.4 |

| Test | Subclassgroup | Result [mg/mL] |
|---|---|---|
| IgG-subclass distribution | IgG1 (mg/ml) | 54.4779 |
| | IgG2 (mg/ml) | 33.6428 |
| | IgG3 (mg/ml) | 6.3377 |
| | IgG4 (mg/ml) | 1.9745 |

| Test | Unit | Result |
|---|---|---|
| IgG Fc Function Hemaggl. | % | 84 |
| Amidolytic activity (PL-1) | nmol/ml min | 14.8 |
| | | 1.37 |
| Anticomple. Activity | % | 35 |
| PKA | % ref lot 3 | 0.741 |
| | IU/ml | 0.6 |
| | | 1.700 |
| | | 2.036 |
| | | <4 |
| NAPTT | mg | >10 |
| Appearance | | Satisfactory |
| pH | | 4.7 |
| Factor XIa | mIU/mL | 0.15 |
| SN13a | mU/ml | 21.9 |
| Thrombin generation assay | | 142.23 |
| Osmolality | mosmol/kg | 259 |
| Density | g/cm3 | 1.0326 |
| Complement factor I | µg/ml | 107 |
| Amidolytic activity profil | S-2288 | 26.9 |
| | S-2266 | 18.8 |
| | S-2222 | <5 |
| | S-2251 | <5 |
| | S-2302 | 55.2 |

TABLE 38-continued

Biochemical characterization of the final IgG composition enriched from cryo-poor plasma using an initial low pH (5.4), high alcohol (25%) initial precipitation step and an anion exchange loading concentration of 157 mg/mL ANX resin (P03510NG2).

| SD reagents | | |
|---|---|---|
| Octoxynol 9 (Triton X100) | ppm | <0.1 |
| Polysorbate 80 | ppm | <26 |
| Tri(n-butyl)phosphate | ppm | <0.2 |
| Antibodies | | |
| Anti D Antibodies | | Satisfactory |
| Anti A&AntiB Hemagglutinins | Anti A | 8 |
| | Anti B | 8 |

TABLE 39

Biochemical characterization of the final IgG composition enriched from cryo-poor plasma using an initial low pH (5.4), high alcohol (25%) initial precipitation step and an anion exchange loading concentration of 106 mg/mL ANX resin (P03610NG2).

| Test | Unit | Result |
|---|---|---|
| Total Protein - Kjeldahl | mg/ml | 103.5231 |
| Purity (CAE) | Albumin % | 0 |
| | α/β globulin % | 0 |
| | γ-globulin % | 100 |
| | denat. Protein % | 0 |
| Molecular size distribution | Monomer [%] | 92.9679 |
| | Dimer [%] | 6.9018 |
| | Polymer [%] | 0.0526 |
| | Fragments [%] | 0.0778 |
| IgG neph | g/l | 95 |
| IgA (ELISA) | mg/ml | 0.07 |
| IgM (ELISA) | mg/dl | <0.95 |
| Fibrinogen (ELISA) | µg/ml | 0.20 |
| Plasminogen (ELISA) | µg/ml | 0.29 |
| C3 complement | mg/dl | <19.4 |

| Test | Subclassgroup | Result [mg/mL] |
|---|---|---|
| IgG-subclass distribution | IgG1 (mg/ml) | 59.3788 |
| | IgG2 (mg/ml) | 34.8724 |
| | IgG3 (mg/ml) | 6.7758 |
| | IgG4 (mg/ml) | 2.1446 |

| Test | Unit | Result |
|---|---|---|
| IgG Fc Function Hemaggl. | % | 101 |
| Amidolytic activity (PL-1) | nmol/ml min | <10 |
| | | 0.951 |

TABLE 39-continued

Biochemical characterization of the final IgG composition enriched from cryo-poor plasma using an initial low pH (5.4), high alcohol (25%) initial precipitation step and an anion exchange loading concentration of 106 mg/mL ANX resin (P03610NG2).

| | | |
|---|---|---|
| Anticomple. Activity | % | 39 |
| PKA | % ref lot 3 | <1 |
| | IU/ml | 0 |
| | | <4 |
| NAPTT | mg | >10 |
| Appearance | | Satisfactory |
| pH | | 4.7 |
| Factor XIa | mIU/mL | 0.06 |
| SN13a | mU/ml | 14.9 |
| Thrombin generation assay | | 123.96 |
| Osmolality | mosmol/kg | 260 |
| Density | g/cm3 | 1.0333 |
| Complement factor I | µg/ml | 80.0 |
| Amidolytic activity profil | S-2288 | 20.3 |
| | S-2266 | 17.2 |
| | S-2222 | <5 |
| | S-2251 | <5 |
| | S-2302 | 38.9 |
| SD reagents | | |
| Octoxynol 9 (Triton X100) | ppm | <0.1 |
| Polysorbate 80 | ppm | <26 |
| Tri(n-butyl)phosphate | ppm | <0.2 |
| Antibodies | | |
| Anti D Antibodies | | Satisfactory |
| Anti A&AntiB Hemagglutinins | Anti A | 16 |
| | Anti B | 8 |

Example 9—Additional Characterization of Fractionation Products

The immunoglobulin G yield and purity achieved using purification methods that include an initial low pH, high alcohol precipitation were compared to those achieved using traditional Cohn precipitation I and precipitation II+III intermediates.

The yield and purity of three large scale IgG purifications employing an initial low pH, high alcohol precipitation—lot 3010, as described in Example 5 ("P03010NG2"); lot 3610 as described in Example 8 ("P03610NG2"); and a third lot 1111, prepared similarly to lots 3010 and 3610, was compared to the average yield for GAMMAGARD LIQUID (10% Immune Globulin Infusion (Human), Baxter International) prepared at a single manufacturing plant in 2010. The GAMMAGARD LIQUID purification process was substantially similar to the processes used to prepare lots 3010, 3610, and 1111, except that the GAMMAGARD LIQUID process proceeded through Cohn Fraction I and Cohn Fraction II+III intermediates, rather than an initial low pH, high alcohol precipitation. Characterization of the precipitate G products formed during the preparation of the experimental lots and averaged for GAMMAGARD LIQUID is shown in Table 40.

TABLE 40

Biochemical characterization of the precipitate G (Ppt G) intermediate formed during preparation of experimental IgG lots 3010, 3610, and 1111, proceeding through an initial low pH, high alcohol precipitation step, and averaged for GAMMAGARD LIQUID preparation as a single manufacturing plant in the year 2010, proceeding through Cohn Fraction I and II + III precipitation steps.

| | | Lot Number | | | GAMMAGARD |
|---|---|---|---|---|---|
| | | 3010 | 3610 | 1111 | LIQUID |
| IgG in Cohn Pool | g/L plasma (PPD/PS-test) | 5.26 | 6.01 | 6.91 | 5.82 (Avg) |
| Characterization of Precipitate G | | | | | |
| IgG | g/L plasma (PPD/PS-test) | 4.99 | 5.81 | 6.14 | 82.9 (Avg) |
| IgG | % of Cohn Pool | 94.9 | 96.6 | 88.9 | 82.9 |
| C3 | % of protein | 0.4 | 1.8 | 1.5 | 0.1-0.6 (mean = 0.2) |
| Fibrinogen | % of protein | 0.12 | 0.68 | 1.02 | 0.01-1.0 (mean = 0.13) |

As seen in Table 40, use of an initial low pH, high alcohol precipitation step resulted in a significant increase in the IgG recovery at the precipitate G intermediate step as compared to the GAMMAGARD LIQUID purification method proceeding through Cohn Fraction I and II+III precipitation steps (88.9-96.6% IgG recovery for initial high alcohol, low pH precipitation step vs. 82.9% for Cohn Fraction I and II+III precipitation steps).

The IgG precipitate G intermediates formed in experimental lots 3010, 3610, and 1111 have slightly lower purity than does the average GAMMAGARD LIQUID precipitate G intermediate, as evidenced by the higher levels of complement component 3 (C3) and fibrinogen, although the fibrinogen content of these intermediates is still within the range of values seen for the GAMMAGARD LIQUID manufacturing. However, when the experimental lots were further processed as described above, the final IgG product met all manufacturing specifications tested, as shown in Table 41.

TABLE 41

Biochemical characterization of final pooled human IgG compositions for experimental lots 3010, 3610, and 1111, proceeding through an initial low pH, high alcohol precipitation step.

| | | Lot number | | |
|---|---|---|---|---|
| Lot | | 3010 | 3610 | 1111 |
| Protein | g/L plasma | 4.45 | 4.54 | 4.82 |
| IgA | % | 0.05 | 0.07 | 0.04 |
| IgM | mg/dL | <1.6 | <1.6 | <1.6 |
| Fibrinogen | µg/mL | <0.17 | 0.2 | <0.17 |
| C3 | mg/mL | <0.194 | <0.194 | <0.194 |
| Fc Function | % | 109 | 101 | 78 |
| HP-SEC | % monomers and dimers | 99.8 | 99.4 | 99.8 |
| CAE | % g-globulin | 100 | 100 | 100 |
| ACA | % | 38 | 39 | 46 |
| PKA | IU/mL | 1 | 0 | 1 |
| PL-1 | nmol/ml min (QC) | <10 | <10 | <10 |
| NAPTT | mg | >10 | >10 | >10 |
| TGA | % of normal plasma control @5% | 123 | 124 | 112 |
| Specific F-XIa | mU/mL | <0.04 | 0.06 | <0.2 |

Example 10—Characterization of Albumin Compositions

To further validate that the new immunoglobulin G manufacturing processes described herein (e.g., those proceeding through an initial low pH, high alcohol precipitation step) could support the manufacture of plasma protein by-products, albumin was purified from a low pH, high alcohol supernatant.

Methods for purifying albumin from Cohn Fraction IV-1 and IV-4 supernatants are well known in the art. Typically, the Cohn Fraction IV-1 and IV-4 supernatants are formed in a process that proceeds through intermediate alcohol precipitations steps, such as Cohn Fraction I and Cohn Fraction II+III precipitations. In the present Example, albumin was prepared according to standard methods, except that the supernatant from an initial low pH, high alcohol precipitation was used in place of a Fraction IV-1 supernatant. As shown in Table 42, the purification from a low pH, high alcohol supernatant resulted in a high yield of albumin (18.92 g/L plasma), which met all quality control requirements tested.

TABLE 42

Biochemical characterization of an albumin composition prepared from a large-scale low pH, high alcohol precipitation supernatant, as described above.

| Test | Unit | AUF00111NG2 Final container |
|---|---|---|
| Protein yield | g/L plasma | 18.92 |
| Albumin (CAE) | (%) | 97.3 |
| | (%) after 2 weeks at 30° C. | 97.8 |
| HPLC | (% monomers) | 98.1 |
| Citrate | μmol/mL | <0.05 |
| PKA | IE/mL | <4 |
| Visual inspection | Vials rejected (e.g., due to particles) | None |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for manufacturing an enriched immunoglobulin composition, the method comprising the steps of:
   (a) co-precipitating immunoglobulins and alpha-1-antitrypsin (A1PI) from a Cohn pool in a first alcohol precipitation step by adding ethanol to the Cohn pool to a final ethanol concentration of from 20% to 30% (v/v) at a pH of from 5.0 to 6.0, thereby forming a first precipitate comprising the precipitated A1PI and the precipitated immunoglobins and a first supernatant, wherein the first precipitate contains at least 85% of the A1PI content of the Cohn pool;
   (b) separating the first precipitate from the first supernatant;
   (c) solubilizing immunoglobulins in the separated first precipitate, thereby forming a first suspension having a soluble portion comprising the solubilized immunoglobulins and an insoluble portion comprising insolubilized A1PI; and
   (d) separating the soluble portion of the first suspension from the insoluble portion of the first suspension thereby forming an enriched immunoglobulin composition,
   wherein the Cohn pool is not contacted with ethanol prior to step (a).

2. The method of claim 1, wherein the final ethanol concentration is 25±4%.

3. The method of claim 1, wherein the final ethanol concentration is 25±3%.

4. The method of claim 1, wherein the final ethanol concentration is 25±2%.

5. The method of claim 1, wherein the final ethanol concentration is 25±1%.

6. The method of claim 5, wherein the final ethanol concentration is 25%.

7. The method of claim 1, wherein the pH is 5.5±0.4.

8. The method of claim 7, wherein the pH is 5.5±0.3.

9. The method of claim 7, wherein the pH is 5.5±0.2.

10. The method of claim 7, wherein the pH is 5.5±0.1.

11. The method of claim 7, wherein the pH is 5.5.

12. The method of claim 1, wherein the pH is maintained for the duration of the first alcohol precipitation step.

13. The method of claim 1, wherein the first alcohol precipitation step comprises adding the alcohol by diffuse addition.

14. The method of claim 13, wherein the diffuse addition comprises spraying.

15. The method of claim 1, wherein the first alcohol precipitation step comprises adding the alcohol at a site adjacent to an impeller.

16. The method of claim 1, wherein the first alcohol precipitation step is performed at a temperature of from −3° C. to −10° C.

17. The method of claim 16, wherein the first alcohol precipitation step is performed at a temperature of from −5° C. to −9° C.

18. The method of claim 1, wherein the first precipitate is suspended with from 4 L to 60 L of buffer per kg precipitate.

19. The method of claim 18, wherein the first precipitate is suspended with from 8 L to 15 L of buffer per kg precipitate.

20. The method of claim 1, wherein the first suspension has a pH of from 4.0 to 5.4.

21. The method of claim 1, wherein the first suspension has a pH of from 4.7 to 5.1.

22. The method of claim 1, wherein the first suspension has a conductivity of from 0 mS/cm to 4 mS/cm.

23. The method of claim 1, wherein the first suspension has a conductivity of from 0.5 mS/cm to 2 mS/cm.

24. The method of claim 1, wherein the first precipitate is suspended in a buffer comprising acetate and/or phosphate.

25. The method of claim 1, wherein the soluble portion of the first suspension is separated from the insoluble portion of the first suspension by centrifugation or filtration.

26. The method of claim 1, wherein the step of separating the soluble portion of the first suspension from the insoluble portion of the first suspension comprises:
   mixing finely divided silicon dioxide ($SiO_2$) with the first suspension, thereby forming a treated suspension; and separating the $SiO_2$ from the treated suspension.

27. The method of claim 26, wherein the finely divided silicon dioxide ($SiO_2$) has an average surface area of from 350 $m^2/g$ to 410 $m^2/g$.

28. The method of claim 26, wherein the finely divided silicon dioxide (SiO$_2$) is added to the first suspension at a final concentration of from 15 g/kg first precipitate to 80 g/kg first precipitate.

29. The method of claim 1, wherein the method comprises the steps of:
(a) co-precipitating immunoglobulins and A1PI from the Cohn pool in the first precipitation step by adding ethanol to the Cohn pool to a final ethanol concentration of from 24% to 26% at a pH of from 5.3 to 5.7 and temperature of between −6° C. and −8° C., thereby forming the first precipitate comprising the precipitated A1PI and the precipitated immunoglobulins and the first supernatant;
(b) separating the first precipitate from the first supernatant;
(c) solubilizing the immunoglobulins in the separated first precipitate, thereby forming the first suspension having a soluble portion comprising the solubilized immunoglobulins and an insoluble portion comprising insolubilized A1PI,
(d) treating the first suspension with finely divided silicon dioxide (SiO$_2$), thereby forming a treated suspension;
(e) separating the soluble fraction of the treated suspension from the insoluble fraction of the treated suspension and SiO$_2$, thereby forming an enriched immunoglobulin composition.

30. The method of claim 1, wherein the enriched immunoglobulin composition contains at least 90% of the immunoglobulin content of at least one immunoglobulin class present in the Cohn pool used in step (a).

31. The method of claim 30, wherein the enriched immunoglobulin composition contains at least 95% of the immunoglobulin content of at least one immunoglobulin class present in the Cohn pool used in step (a).

32. The method of claim 30, wherein the immunoglobulin class is IgG.

33. The method of claim 1, wherein the method further comprises the steps of:
(f) precipitating immunoglobulins from the enriched immunoglobulin composition in a second precipitation step, thereby forming a second precipitate and a second supernatant;
(g) suspending the second precipitate to form a second suspension having a soluble portion comprising immunoglobulins and an insoluble portion; and
(h) recovering the soluble fraction of the second suspension, thereby forming a further enriched immunoglobulin composition.

34. The method of claim 33, wherein the second precipitation step is an alcohol precipitation step.

35. The method of claim 34, wherein the alcohol precipitation step comprises adding ethanol to the enriched immunoglobulin composition to a final concentration of between 22% and 28% ethanol at a pH between 6.5 and 7.5.

36. The method of claim 34, wherein the second precipitation step comprises adding the alcohol by diffuse addition.

37. The method of claim 36, wherein the diffuse addition comprises spraying.

38. The method of claim 34, wherein the second precipitation step comprises adding the alcohol at a site adjacent to an impeller.

39. The method of claim 34, wherein the second precipitation step is performed at a temperature between −3° C. and −10° C.

40. The method of claim 33, wherein the enriched immunoglobulin composition contains at least 90% of the immunoglobulin G content present in the Cohn pool used in step (a).

41. The method of claim 40, wherein the enriched immunoglobulin composition contains at least 95% of the immunoglobulin G content present in the Cohn pool used in step (a).

42. The method of claim 1, wherein the method further comprises a cation exchange chromatography enrichment step.

43. The method of claim 1, wherein the method further comprises an anion exchange chromatography enrichment step.

44. The method of claim 1, wherein the method further comprises a viral inactivation and/or removal step.

45. The method of claim 44, wherein the method comprises a solvent/detergent (S/D) viral inactivation step.

46. The method of claim 44, wherein the method comprises a nanofiltration step.

47. The method of claim 44, wherein the method comprises a step of incubating the composition at a pH from 4.0 to 5.0 and temperature from 20° C. to 40° C. for at least one week.

48. The method of claim 1, comprising further enrichment of immunoglobulins in the enriched immunoglobulin composition, thereby forming a final enriched IgG composition comprising at least 98% IgG.

49. The method of claim 48, wherein the final enriched IgG composition comprises at least 99% IgG.

50. The method of claim 1, wherein the method yields at least 4 g of IgG per L of Cohn pool used in step (a).

51. The method of claim 50, wherein the method yields at least 4.25 g of IgG per L of Cohn pool used in step (a).

52. The method of claim 50, wherein the method yields at least 4.5 g of IgG per L of Cohn pool used in step (a).

53. The method of claim 1, wherein alpha-1-antitrypsin (A1PI) is further purified from the insoluble fraction of the first suspension.

54. The method of claim 1, wherein fibrinogen is further purified from the insoluble fraction of the first suspension.

55. The method of claim 1, wherein Factor H is further purified from the insoluble fraction of the first suspension.

56. The method of claim 1, wherein an Inter-alpha-Trypsin Inhibitor protein (IaIp) is further purified from the insoluble fraction of the first suspension.

57. The method of claim 53, wherein the insoluble fraction of the first suspension is treated with finely divided silicon dioxide (SiO$_2$).

58. The method of claim 1, wherein albumin is further purified from the first supernatant.

59. The method of claim 1, wherein the Cohn pool is cryo-poor plasma.

60. The method of claim 1, wherein the first precipitate contains at least 90% of the A1PI content of the Cohn pool.

61. The method of claim 1, the first precipitate contains at least 95% of the A1PI content of the Cohn pool.

\* \* \* \* \*